(12) United States Patent
Salvemini et al.

(10) Patent No.: US 8,217,166 B2
(45) Date of Patent: Jul. 10, 2012

(54) POLYETHYLENE GLYCOLATED SUPEROXIDE DISMUTASE MIMETICS

(75) Inventors: Daniela Salvemini, Chesterfield, MO (US); William L. Neumann, St. Louis, MO (US); Samuel Tremont, St. Louis, MO (US); Kishore Udipi, Santa Rosa, CA (US); Amruta Reddy Poreddy, St. Louis, MO (US)

(73) Assignee: Galera Therapeutics, LLC, St. Louis, MO (US)

( * ) Notice: Subject to any disclaimer, the term of this patent is extended or adjusted under 35 U.S.C. 154(b) by 1169 days.

(21) Appl. No.: 11/766,221

(22) Filed: Jun. 21, 2007

(65) Prior Publication Data

US 2008/0318917 A1 Dec. 25, 2008

(51) Int. Cl.
*C07B 47/00* (2006.01)
*C07D 487/22* (2006.01)
(52) U.S. Cl. ...................................... 540/145
(58) Field of Classification Search ................... 540/140, 540/145; 514/145, 186, 154
See application file for complete search history.

(56) References Cited

U.S. PATENT DOCUMENTS

| | | | |
|---|---|---|---|
| 5,610,293 A | 3/1997 | Riley et al. | |
| 5,637,578 A | 6/1997 | Riley et al. | |
| 5,874,421 A | 2/1999 | Riley et al. | |
| 5,976,498 A | 11/1999 | Neumann et al. | |
| 6,084,093 A | 7/2000 | Riley et al. | |
| 6,180,620 B1 | 1/2001 | Salvemini et al. | |
| 6,204,259 B1 | 3/2001 | Riley et al. | |
| 6,214,817 B1 * | 4/2001 | Riley et al. | 514/186 |
| 6,395,725 B1 | 5/2002 | Salvemini et al. | |
| 6,525,041 B1 | 2/2003 | Neumann et al. | |
| 2004/0137638 A1 | 7/2004 | Slomczynska et al. | |

OTHER PUBLICATIONS

Riley, Stopped Flow Kinetic Analysis for Monitoring Superoxide Decay in Aqueous Systems, Anal. Biochem, 196: 344-349, 1991.
Roberts et al, Effect of PEGylation on pharmaceuticals, Adv. Drug Delivery Rev. 54:459 576, 2002.
Salvemini et al, Amelioration of joint disease in a rat model of collagen-induced arthritis by M40403, a superoxide dismutase mimetic, Arthritis & Rheumatism 44:2909-2921, 2001.
Salvemini et al., A nonpeptidyl mimic of superoxide dismutase with therapeutic activity in rats, Science 286:304-306, 1999.
Veronese et al, Polyethylene glycol-superoxide dismutase, a conjugate in search of exploitation, Adv. Drug Deilv. Rev. 54:587-606, 2002.

* cited by examiner

*Primary Examiner* — Paul V. Ward
(74) *Attorney, Agent, or Firm* — SNR Denton US LLP

(57) ABSTRACT

Compounds and methods for utilizing compounds comprising a superoxide dismutase mimetic covalently linked to polyethylene glycol. Methods are also provided for preparing a superoxide dismutase mimetic covalently linked to a polyethylene glycol, the methods comprising reacting an activated polyethylene glycol with a superoxide dismutase mimetic, or alternatively, reacting a superoxide dismutase mimetic with an activated polyethylene glycol. A method is also provided for preventing or treating a disease or disorder in which superoxide anions are implicated, comprising administering to a subject in need thereof, a therapeutically effective amount of a compound comprising a superoxide dismutase mimetic covalently linked to a polyethylene glycol. Methods of determining the safety and efficacy of the compounds ere also provided. Methods for determining the safety and efficacy can include methods in lab animals and humans.

92 Claims, 3 Drawing Sheets

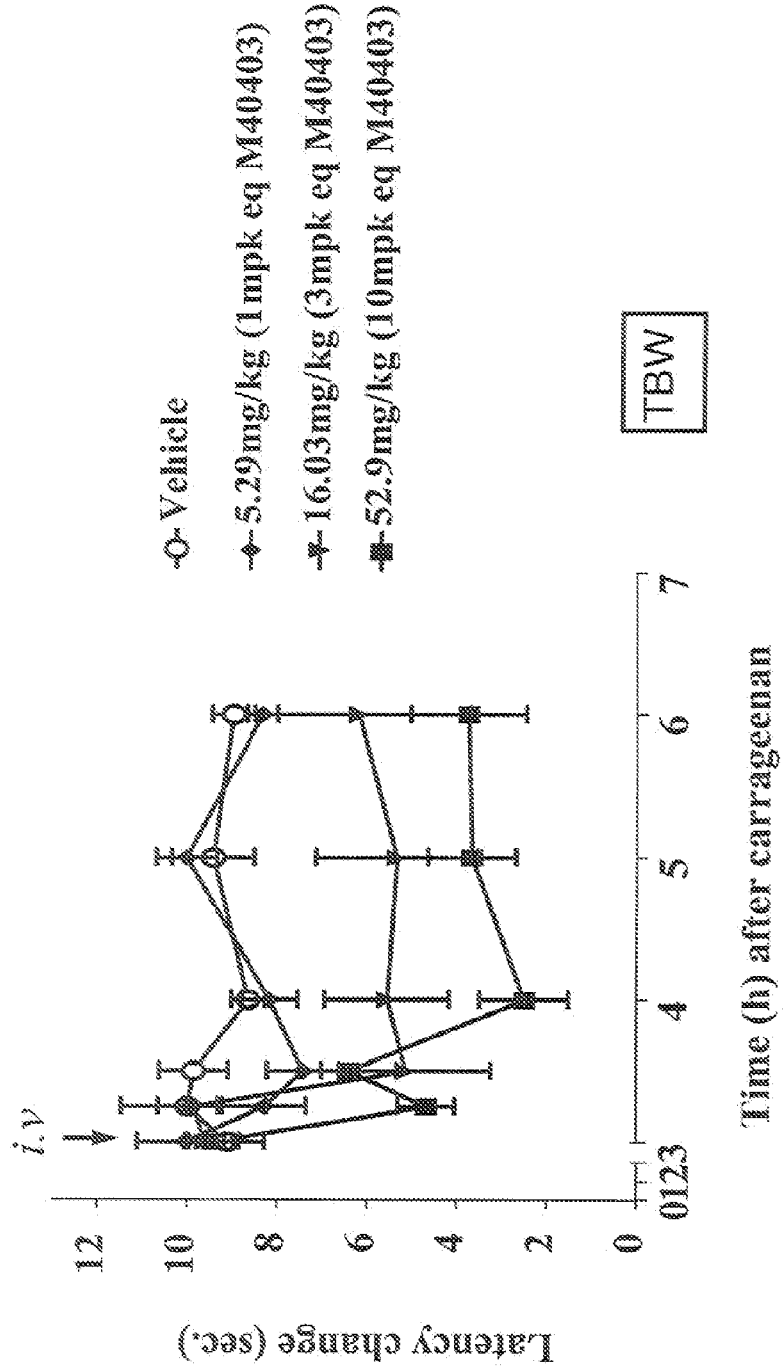
FIG. 1 Inhibition of Carrageenan-Induced Hyperalgesia by M40618

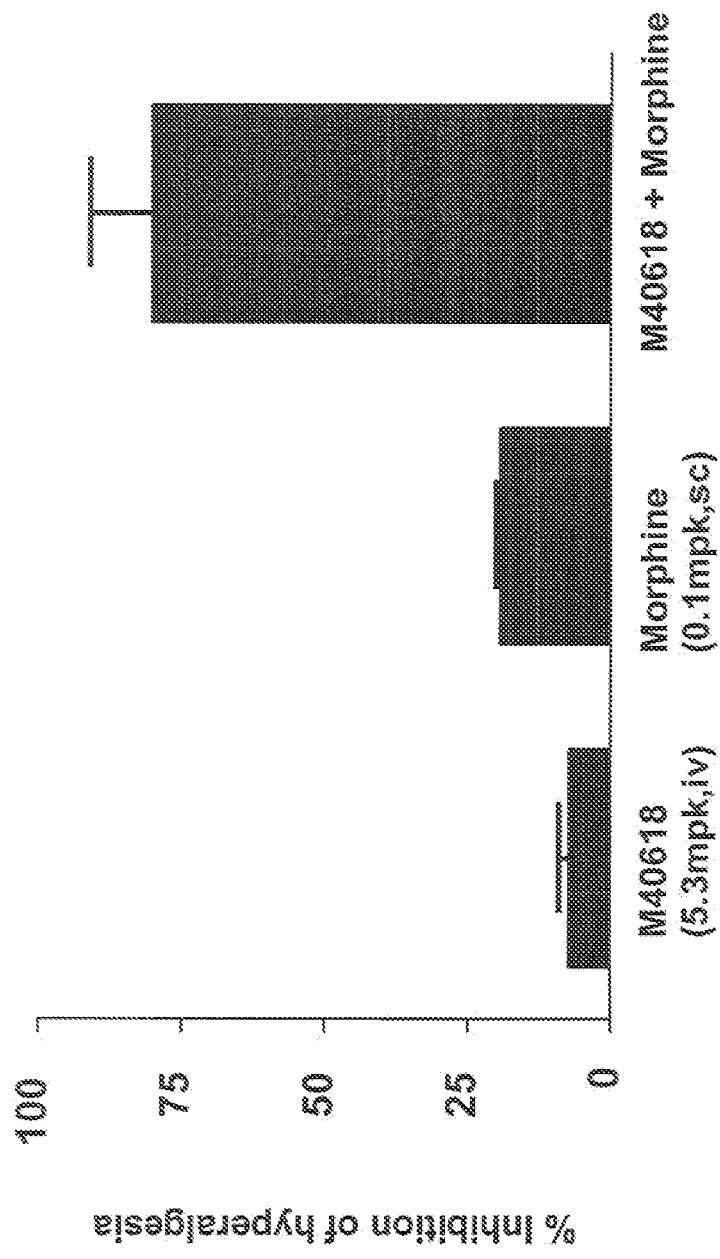
FIG. 2 M40618 enhances the analgesic activity of morphine
Carrageenan-induced hyperalgesia model in rats, therapeutic administration.

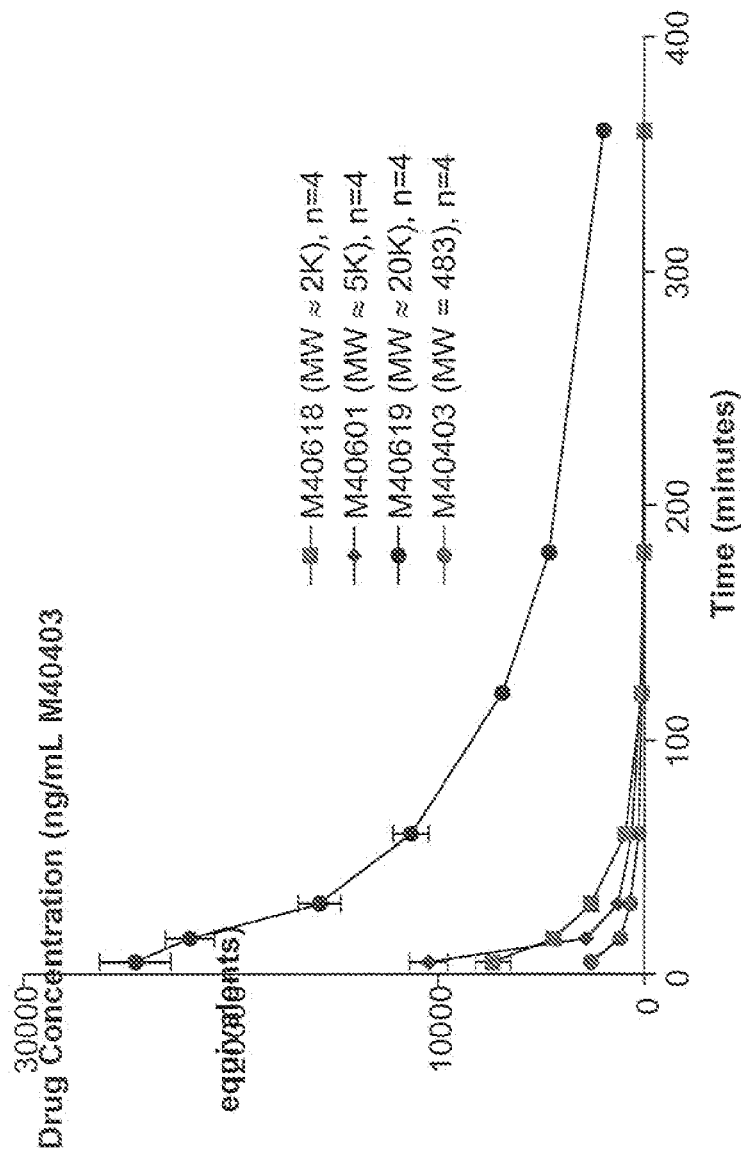
FIG. 3 Pharmacokinetic profile of PEG SODm Compounds

POLYETHYLENE GLYCOLATED SUPEROXIDE DISMUTASE MIMETICS

STATEMENT REGARDING FEDERALLY SPONSORED RESEARCH OR DEVELOPMENT

Not Applicable.

INCORPORATION-BY-REFERENCE OF MATERIAL SUBMITTED ON A COMPACT DISC

Not Applicable.

BACKGROUND OF THE INVENTION

1. Field of the Invention

This invention relates generally to compounds which are effective as catalysts for dissimulation of superoxide.

2. Description of Related Art

Superoxide dismutase is an enzyme that catalyzes the conversion of superoxide into molecular oxygen and hydrogen peroxide to provide a first line of defense against superoxide and reactive oxygen metabolites derived from superoxide. Such reactive oxygen metabolites are known to contribute to the numerous tissue pathologies including those involved in inflammatory diseases and disorders. Recently, the nonpeptidyl mimetics of superoxide dismutase have been identified (see for example, U.S. Pat. No. 8,214,817 to Riley et al.). These superoxide dismutase mimetics have been shown to be effective in various diseases including inflammation (Salvemini et al., Science 286:304-306, 1999; Salvemini et al., Arthritis & Rheumatism 44:2909-2921, 2001).

The natural occurring superoxide dismutase protein has been conjugated to various substances and, in particular, to polyethylene glycol (for review see Veronese et al., Adv. Drug Deliv. Rev. 54:587-606, 2002). Nevertheless, conjugation of superoxide dismutase mimetics with polymeric substances having molecular weights tower than those in the million Da range have not been heretofore disclosed.

BRIEF SUMMARY OF THE INVENTION

Accordingly, the inventors herein have succeeded in discovering that superoxide dismutase mimetics can be conjugated with polyethylene glycols. Such conjugates retain in vitro catalytic activity and in vivo efficacy while exhibiting increased plasma levels and half-life. The inventors have also shown that these PEGylated superoxide dismutase mimetics have lower toxicity than their unPEGylated counterparts.

Thus, in various embodiments, the present invention is directed to compounds and compositions comprising a superoxide dismutase mimetic covalently linked to a polyethylene glycol.

Methods are also provided for preparing a superoxide dismutase mimetic covalently linked to a polyethylene glycol, the methods comprising reacting an activated polyethylene glycol with a superoxide dismutase mimetic, or alternatively, reacting a superoxide dismutase mimetic with an activated polyethylene glycol.

A method is also provided for preventing or treating a disease or disorder in which superoxide anions are implicated, comprising administering to a subject in need thereof, a therapeutically effective amount of a compound comprising a superoxide dismutase mimetic covalently linked to a polyethylene glycol.

Methods of determining the safety and efficacy of the compounds are also provided. Methods for determining the safety and efficacy can include methods in lab animals and humans.

These and other features, aspects and advantages of the present invention will become better understood with reference to the following description, examples and appended claims.

BRIEF DESCRIPTION OF THE SEVERAL VIEWS OF THE DRAWINGS

FIG. 1 illustrates the inhibition of carrageenan-induced hyperalgesia by increasing concentrations of compound VIII.

FIG. 2 illustrates the percent inhibition of hyperalgesia produced by compound VIII administered intravenously at 5.3 mg/kg; morphine administered subcutaneously at 0.1 mg/kg or the combination of VIII (5.3 mg/kg, i.v.) and morphine (0.1 microgram/kg s.c.).

FIG. 3 illustrates the time course of plasma concentrations equivalents following intravenous administration of three superoxide dismutase mimetic-PEG conjugates compared to the corresponding superoxide dismutase mimetic.

DETAILED DESCRIPTION OF THE INVENTION

Abbreviations and Definitions

To facilitate understanding of the invention, a number of terms and abbreviations as used herein are defined below as follows:

As utilized herein, the term "SOD mimetic" or "superoxide dismutase mimetic" means a low-molecular-weight catalyst for the conversion of superoxide anions into hydrogen peroxide and molecular oxygen. These catalysts consist of an organic ligand having a pentaazacyclopentadecane portion and a chelated transition metal ion, which includes but is not limited to, for example, manganese, iron, nickel, copper, and vanadium. The term may include catalysts containing short-chain polypeptides (under 15 amino acids), or macrocyclic structures derived from amino acids, as the organic ligand. The term explicitly excludes a superoxide dismutase enzyme obtained from any natural sources.

The term "precursor ligand" means the organic ligand of a SOD mimetic without the chelated transition metal cation and charge neutralizing anions.

The term "substituted" means that the described moeity has one or more substituents comprising at least 1 carbon or heteroatom, and further comprising from 0 to 22 carbon atoms or from 1 to 15 carbon atoms, and comprising from 0 to 22 or from 0 to 15 heteroatoms selected from the group consisting of: O, S, N, P, Si, B, F, Cl, Br, and I. These atoms may be arranged in a number of configurations, creating substituent groups which are unsaturated, saturated, or aromatic. Examples of such substituents include branched or unbranched alkyl, alkenyl, or alkynyl, cyclic, heterocyclic, aryl, heteroaryl, allyl, polycycloalkyl, polycycloaryl, polycycloheteroaryl, imines, aminoalkyl, hydroxyalkyl, hydroxyalkyl, phenol, amine oxides, thioalkyl, carboalkoxyalkyl, carboxylic acids and their derivatives, keto, ether, aldehyde, amine, amide, nitrile, halo, thiol, sulfoxide, sulfone, sulfonic acid, sulfide, disulfide, phosphonic acid, phosphinic acid, acrylic acid, sulphonamides, amino acids, peptides, proteins, carbohydrates, nucleic acids, fatty acids, lipids, nitro, hydroxylamines, hydroxamic acids, thiocarbonyls, thiocarbonyls, borates, boranes, boraza, silyl, silaza, siloxy, and combinations thereof.

The term "alkyl", alone or in combination, means a straight-chain or branched-chain alkyl containing from 1 to about 22 carbon atoms, from about 1 to about 18 carbon atoms or from about 1 to about 12 carbon atoms. Examples of such carbon compounds include, but are not limited to, methyl, ethyl, n-propyl, isopropyl, n-butyl, isobutyl, sec-butyl, tert-butyl, pentyl, iso-amyl, hexyl, octyl, nonyl, decyl, dodecyl, tetradecyl, hexadecyl, octadecyl and eicosyl.

The term "alkenyl", alone or in combination, means an alkyl having one or more double bonds. Examples of such alkenyls include, but are not limited to, ethenyl, propenyl, 1-butenyl cis-2-butenyl, trans-2-butenyl, iso-butylenyl, cis-2-pentenyl, trans-2-pentenyl, 3-methyl-1-butenyl, 2,3-dimethyl-2-butenyl, 1-pentenyl, 1-hexenyl, 1-octenyl, decenyl, dodecenyl, tetradecenyl, hexadecenyl, cis- and trans-9-octadecenyl, 1,3-pentadienyl, 2,4-pentadienyl, 2,3-pentadienyl, 1,3-hexadienyl, 2,4-hexadienyl, 5,8,11,14-eicosatetraenyl, and 9,12,15-octadecatrienyl.

The term "alkynyl", alone or in combination, means an alkyl having one or more triple bonds. Examples of such alkynyl groups include, but are not limited to, ethynyl, propynyl (propargyl), 1-butynyl, 1-octynyl, 9-octadecynyl, 1,3-pentadiynyl, 2,4-pentadiynyl, 1,3-hexadiynyl, and 2,4-hexadiynyl.

The term "cycloalkyl", alone or in combination means a cycloalkyl containing from 3 to about 10, preferably from 3 to about 8, and most preferably from 3 to about 6, carbon atoms. Examples of such cycloalkyl include, but are not limited to, cyclopropyl, cyclobutyl, cyclopentyl, cyclohexyl, cycloheptyl, cyclooctyl, and perhydronaphthyl.

The term "cycloalkylalkyl" means an alkyl as defined above which is substituted by a cycloalkyl as defined above. Examples of cycloalkylalkyl s include, but are not limited to, cyclohexylmethyl, cyclopentylmethyl, (4-isopropylcyclohexyl)methyl, (4-t-butyl-cyclohexyl)methyl, 3-cyclohexylpropyl, 2-cyclohexylmethylpentyl, 3-cyclopentylmethylhexyl, 1-(4-neopentylcyclohexyl)methylhexyl, and 1-(4-isopropylcyclohexyl)methylheptyl.

The term "cycloalkylcycloalkyl" means a cycloalkyl as defined above which is substituted by another cycloalkyl as defined above. Examples of cycloalkylcycloalkyl s include, but are not limited to, cyclohexylcyclopentyl and cyclohexylcyclohexyl.

The term "cycloalkenyl", alone or in combination, means a cycloalkyl having one or more double bonds. Examples of aycloalkenyl s include, but are not limited to, cyclopentenyl, cyclohexenyl, cyclooctenyl, cyclopentadienyl, cyclohexadienyl and cyclooctadienyl.

The term "cycloalkenylalkyl" means an alkyl as defined above which is substituted by a cycloalkenyl as defined above. Examples of cycloalkenylalkyl s include, but are not limited to, 2-cyclohexen-1-ylmethyl, 1-cyclopenten-1-ylmethyl, 2-(1-cyclohexen-1-yl)ethyl, 3-(1-cyclopenten-1-yl) propyl, 1-(1-cyclohexen-1-ylmethyl)pentyl, 1-(1-cyclopenten-1-yl)hexyl, 6-(1-cyclohexen-1-yl)hexyl, 1-(1-cyclopenten-1-yl)nonyl and 1-(1-cyclohexen-1-yl)nonyl.

The terms "alkylcycloalkyl" and "alkenylcycloalkyl" mean a cycloalkyl as defined above which is substituted by an alkyl or alkenyl as defined above. Examples of alkylcycloalkyl and alkenylcycloalkyl s include, but are not limited to, 2-ethylcyclobutyl, 1-methylcyclopentyl, 1-hexylcyclopentyl, 1-methylcyclohexyl, 1-(9-octadecenyl)cyclopentyl and 1-(9-octadecenyl)cyclohexyl.

The terms "alkylcycloalkenyl" and "alkenylcycloalkenyl" means a cycloalkenyl as defined above which is substituted by an alkyl or alkenyl as defined above. Examples of alkyloycloalkenyl and alkenylcycloalkenyl s include, but are not limited to, 1-methyl-2-cyclopentyl, 1-hexyl-2-cyclopentenyl, 1-ethyl-2-cyclohexenyl, 1-butyl-2-cyclohexenyl, 1-(9-octadecenyl)-2-cyclohexenyl and 1-(2-pentenyl)-2-cyclohexenyl.

The term "aryl", alone or in combination, means a phenyl or naphthyl which optionally carries one or more substituents selected from alkyl, cycloalkyl, cycloalkenyl, aryl, heterocycle, alkoxyaryl, alkaryl, alkoxy, halogen, hydroxy, amine, cyano, nitro, alkylthio, phenoxy, ether, trifluoromethyl and the like, such as phenyl p-tolyl, 4-methoxyphenyl, 4-(tert-butoxy)phenyl, 4-fluorophenyl, 4-chlorophenyl, 4-hydroxyphenyl, 1-naphthyl, 2-naphthyl, and the like.

The term "aralkyl", alone or in combination, means an alkyl or cycloalkyl as defined above in which one hydrogen atom is replaced by an aryl as defined above, such as benzyl, 2-phenylethyl, and the like.

The term "heterocyclic" means ring structures containing at least one other kind of atom, in addition to carbon, in the ring. The most common of the other kinds of atoms include nitrogen, oxygen and sulfur. Examples of heterocyclics include, but are not limited to, pyrrolidinyl, piperidyl, imidazolidinyl, tetrahydrofuryl, tetrahydrothienyl, furyl, thienyl, pyridyl, quinolyl, isoquinolyl, pyridazinyl, pyrazinyl, indolyl, imidazolyl, oxazolyl, thiazolyl, pyrazolyl, pyridinyl, benzoxadiazolyl, benzothiadiazolyl, triazolyl and tetrazolyl groups.

The term "saturated, partially saturated or unsaturated cyclic" means fused ring structures in which one carbons of the ring are also part of the fifteen-membered macrocyclic ligand. The ring structure can contain from about 3 to about 20 carbon atoms or from about 5 to about 10 carbon atoms, and can also contain one or more other kinds of atoms in addition to carbon. The most common of the other kinds of atoms include nitrogen, oxygen and sulfur. The ring structure can also contain more than one ring.

The term "saturated, partially saturated or unsaturated ring structure" means a ring structure in which one carbon of the ring is also part of the fifteen-membered macrocyclic ligand. The ring structure can contain from about 3 to about 20 or from about 5 to about 10, carbon atoms and can also contain nitrogen, oxygen and/or sulfur atoms.

The term "nitrogen containing heterocycle" means ring structures in which 2 carbons and a nitrogen of the ring are also part of the fifteen-membered macrocyclic ligand. The ring structure can contain from about 2 to about 20 or from about 4 to about 10, carbon atoms, can be substituted or unsubstituted, partially or fully unsaturated or saturated, and can also contain nitrogen, oxygen and/or sulfur atoms in the portion of the ring which is not also part of the fifteen-membered macrocyclic ligand.

A "linking moeity" as described herein can be any bond, or atoms, which are covalently linked so as to create a covalent linkage. For example, the can be a single bond connecting a superoxide dismutase mimetic to a PEG, or a series of atoms of any arrangement or length, including C, N, O, P, or S and any combination thereof.

Reference to disease states and disorders in which superoxide anions are implicated is intended to mean any disease state or disorder in which superoxide anions, or the products of reactions involving superoxide anions (such as peroxonitrite), are known or suspected to be a factor in the progression of the disease state or disorder. Examples of such disease states and disorders are inflammation and ischemic reperfusion injury.

The term "organic acid anion" refers to carboxylic acid anions having from about 1 to about 18 carbon atoms.

The term "halide" means chloride, fluoride, iodide, or bromide.

As used herein, "R" groups means all of the R groups attached to the carbon atoms of the macrocycle, i.e., $R_1$, $R'_1$, $R_2$, $R'_2$, $R_3$, $R'_3$, $R_4$, $R'_4$, $R_5$, $R'_5$, $R_6$, $R'_6$, $R_7$, $R'_7$, $R_8$, $R'_8$, $R_9$, $R'_9$, $R_{10}$, and $R'_{10}$.

The term polyethylene glycol ("PEG") as used herein is intended to mean a polymer of ethylene oxide having repeat units of —($CH_2CH_2$—O)— and the general formula of HO—($CH_2CH_2$—O)$_n$—H. The term "activated polyethylene glycol" refers to a derivative of polyethylene glycol in which one or both of the terminal —OH groups is replaced with a functionalized moiety capable of reacting with a target molecule which can be proteinaceous or non-proteinaceous to form a covalent bond between the polymer and the target.

The term polyethylene glycol ("mPEG") as used herein is intended to mean a polymer of ethylene oxide having repeat units of —($CH_2CH_2$—O)— and the general formula of $CH_3$O—($CH_2CH_2$—O)$_n$—H, for example, a polyethylene glycol capped at one end with a methoxy group.

The term "PEGylation" is intended to refer to a process by which a polyethylene glycol molecule is chemically attached to a target molecule which can be proteinaceous or non-proteinaceous. The polyethylene glycol can be, for example, an activated polyethylene glycol A "PEGylated" compound is a compound formed by a PEGylation reaction.

As used herein, the term "controlled-release component" refers to an agent that facilitates the controlled-release of a compound including, but not limited to, polymers, polymer matrices, gels, permeable membranes, liposomes, microspheres, or the like, or any combination thereof. Methods for producing compounds in combination with controlled-release components are known to those of skill in the art.

As used herein, the term "pharmaceutically acceptable" means approved by a regulatory agency of the Federal or a state government or listed in the U.S. Pharmacopoeia or other generally recognized pharmacopoeia for use in animals, and more particularly in humans.

As used herein, the term "pharmaceutically acceptable carrier" refers to a diluent, adjuvant, excipient, or vehicle with which a compound is administered. Such carriers can be sterile liquids, such as water and oils, including those of petroleum, animal, vegetable or synthetic origin, such as peanut oil, soybean oil, mineral oil, sesame oil and the like, polyethylene glycols, glycerine, propylene glycol or other synthetic solvents. Water is a preferred carrier when a compound is administered intravenously. Saline solutions and aqueous dextrose and glycerol solutions can also be employed as liquid carriers, particularly for injectable solutions. Suitable excipients include starch, glucose, lactose, sucrose, gelatin, malt, rice, flour, chalk, silica get sodium stearate, glycerol monostearate, talc, sodium chloride, dried skim milk, glycerol, propylene, glycol, water, ethanol and the like. A compound, if desired, can also combine minor amounts of wetting or emulsifying agents, or pH buffering agents such as acetates, citrates or phosphates. Antibacterial agents such as benzyl alcohol or methyl parabens; antioxidants such as ascorbic acid or sodium bisulfite; chelating agents such as ethylenediaminetetraacetic acid; and agents for the adjustment of tonicity such as sodium chloride or dextrose may also be a carrier. Methods for producing compounds in combination with carriers are known to those of skill in the art.

As used herein, the term "pharmaceutically acceptable salt" includes those salts of a pharmaceutically acceptable compound formed with free amino groups such as those derived from hydrochloric, phosphoric, acetic, oxalic, tartaric acids, and those formed with free carboxyl groups such as those derived from sodium, potassium, ammonium, calcium, ferric hydroxides, isopropylamine, triethylamine, 2-ethylamino ethanol, histidine, and procaine. If the compound is basic, salts may be prepared from pharmaceutically acceptable non-toxic acids including inorganic and organic acids. Such acids include acetic, benzene-sulfonic (besylate), benzoic, camphorsulfonic, citric, ethenesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric acid, p-toluenesulfonic, and the like. Particularly preferred are besylate, hydrobromic, hydrochloric, phosphoric and sulfuric acids. If the compound is acidic, salts may be prepared from pharmaceutically acceptable organic and inorganic bases. Suitable organic bases include, but are not limited to, lysine, N,N'-dibenzylethylenediamine, chloroprocaine, choline, diethanolamine, ethylenediamine, meglumine (N-methylglucamine) and procaine. Suitable inorganic bases include, but are not limited to, alkaline and earth-alkaline metals such as aluminum, calcium, lithium, magnesium, potassium, sodium and zinc. Methods for synthesizing such salts are known to those of skill in the art.

As used herein, the term "pro-drug" refers to any compound which releases an active drug in vivo when such a compound is administered to a mammalian subject. Pro-drugs can be prepared, for example, by functional group modification of an active drug. The functional group may be cleaved in vivo to release the active drug compound. Pro-drugs include, for example, compounds in which a group that may be cleaved in vivo is attached to a hydroxy, amino or carboxyl group in the active drug. Examples of pro-drugs include, but are not limited to esters (e.g., acetate, methyl, ethyl, formate, and benzoate derivatives), carbamates, amides and ethers. Methods for synthesizing such pro-drugs are known to those of skill in the art.

As used herein, the term "therapeutically effective amount" refers to those amounts that, when administered to a particular subject in view of the nature and severity of that subject's disease or condition, will have a desired therapeutic effect, e.g., an amount which will cure, prevent, inhibit, or at least partially arrest or partially prevent a target disease or condition. More specific embodiments are included in the Pharmaceutical Preparations and Methods of Administration section below.

Superoxide Dismutase Mimetics

The present invention is directed, in one aspect, to superoxide dismutase mimetics covalently linked to polyethylene glycols. Such conjugates retain catalytic activity and in vivo efficacy while exhibiting increased plasma levels and half-fife, and decreased toxicity.

The compounds of the present invention comprise superoxide dismutase mimetics covalently linked to a polyethylene glycol. The superoxide dismutase mimetic can be, for example, a pentaaza macrocycle. The superoxide dismutase mimetic portion of the conjugate can include, generally, those superoxide dismutase mimetics (superoxide dismutase mimetic) disclosed in U.S. Pat. Nos. 5,610,293, 5,637,578, 5,874,421, 5,976,498, 6,084,093, 6,180,620, 6,204,259, 6,214,817, 6,395,725, 6,525,041, and published U.S. Patent Application 2004/0137,638, each of which is incorporated herein by reference in its entirety.

Compounds wherein a PEG is covalently linked to a superoxide dismutase mimetic are linked via a linking moiety. The linking moiety can be any bond, or atoms, which are covalently linked so as to create a covalent attachment between to species. For example, the linking moiety can be a single bond connecting a superoxide dismutase mimetic to a PEG, or a series of atoms of any arrangement or length, including C, N, O, H, or S in any combination. These linking moieties are not limited and can contain any compound which includes esters, ethers, carboxyls, amines, amides, ureas, and all other groups. In various embodiments, such compounds can be characterized by the following formulas and descriptions.

A PEGylated superoxide dismutase mimetic can have a formula:

$$G_A\text{-}G_B\text{-}G_C$$

wherein (a) $G_A$ is a pentaaza macrocycle having formula I:

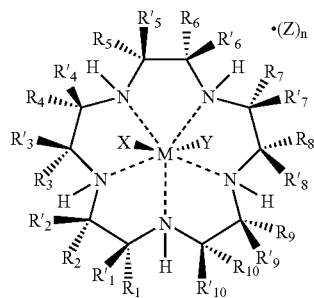

which comprises:

(i) one or more of $R_1$, $R'_1$, $R_2$, $R'_2$, $R_3$, $R'_3$, $R_4$, $R'_4$, $R_5$, $R'_5$, $R_6$, $R'_6$, $R_7$, $R'_7$, $R_8$, $R'_8$, $R_9$, $R'_9$, $R_{10}$, and $R'_{10}$ are independently:

($i^a$) hydrogen; or ($i^b$) a bond; or ($i^c$) a moeity independently selected from the group consisting of alkenyl, alkenylcycloalkenyl, alkenylcycloalkyl, alkyl, alkylaycloalkenyl, alkylcycloalkyl, alkynyl, aralkyl, aryl cycloalkenyl, cycloalkyl, cycloalkylalkyl, cycloalkylcycloalkyl, cycloalkenylalkyl, and heterocyclyl; or ($i^d$) a moiety independently selected from the group consisting of —$OR_{11}$, —$NR_{11}R_{12}$, —$COR_{11}$, —$CO_2R_{11}$, —$CONR_{11}R_{12}$, —$SR_{11}$, $SOR_{11}$, —$SO_2R_{11}$, —$SO_2NR_{11}R_{12}$, —$N(OR_{11})(R_{11})$, —$P(O)(OR_{11})(OR_{12})$, —$P(O)(OR_{11})(R_{12})$, —$OP(O)(OR_{11})(OR_{12})$, $R_{11}NC(O)R_{12}$, —$R_{11}NC(O)R_{12}$ and substituents attached to the α-carbon of α-amino acids, wherein $R_{11}$ and $R_{12}$ are independently hydrogen or alkyl; or (ii) one or more of $R_1$ or $R'_1$ and $R_2$ or $R'_2$, $R_3$ or $R'_3$ and $R_4$ or $R'_4$, $R_5$ or $R'_5$ and $R_6$ or $R'_6$, $R_7$ or $R'_7$ and $R_8$ or $R'_8$, and $R_9$ or $R'_9$ and $R_{10}$ or $R'_{10}$ together with the carbon atoms to which they are attached independently form a cycle or heterocycle which ($ii^a$) are substituted or unsubstituted; ($ii^b$) are saturated, partially saturated or unsaturated; and ($ii^c$) comprise 3 to 20 carbon atoms; and any of $R_1$, $R'_1$, $R_2$, $R'_2$, $R_3$, $R'_3$, $R_4$, $R'_4$, $R_5$, $R'_5$, $R_6$, $R'_6$, $R_7$, $R'_7$, $R_8$, $R'_8$, $R_9$, $R'_9$, $R_{10}$, and $R'_{10}$ not forming said cycle or heterocycle are defined as above: or (iii) one or more of $R_1$ and $R'_1$, $R_2$ and $R'_2$, $R_3$ and $R'_3$, $R_4$ and $R'_4$, $R_5$ and $R'_5$, $R_6$ and $R'_6$, $R_7$ and $R'_7$, $R_8$ and $R'_8$, $R_9$ and $R'_9$, and $R_{10}$ and $R'_{10}$, together with the carbon atom to which they are attached independently form a cycle or heterocycle which (iiia) is substituted or unsubstituted; (iiib) saturated, partially saturated or unsaturated; and (iiic) comprise 3 to 20 carbon atoms; and any of $R_1$, $R'_1$, $R_2$, $R'_2$, $R_3$, $R'_3$, $R_4$, $R'_4$, $R_5$, $R'_5$, $R_6$, $R'_6$, $R_7$, $R'_7$, $R_8$, $R'_8$, $R_9$, $R'_9$, $R_{10}$, and $R'_{10}$ not forming said cycle or heterocycle are defined as above: or (iv) one or more of $R_{10}$ or $R'_{10}$ and $R_1$ or $R'_1$, $R_2$ or $R'_2$ and $R_3$ or $R'_3$, $R_4$ or $R'_4$ and $R_5$ or $R'_5$, $R_6$ or $R'_6$ and $R_7$ or $R'_7$, or $R_8$ or $R'_8$ and $R_9$ or $R'_9$ together with the carbon atoms to which they are attached independently form a nitrogen-containing heterocycle which ($iv^a$) is substituted or unsubstituted; ($iv^b$) is saturated, partially saturated or unsaturated, in which case the hydrogen attached to the nitrogen which is both part of the unsaturated heterocycle and the pentaaza macrocycle and the R groups attached to the carbon atoms which are both past of the heterocycle and the macrocycle are absent; and ($iv^c$) comprises 3 to 20 carbon atoms; and any of $R_1$, $R'_1$, $R_2$, $R'_2$, $R_3$, $R'_3$, $R_4$, $R'_4$, $R_5$, $R'_5$, $R_6$, $R'_6$, $R_7$, $R'_7$, $R_8$, $R'_8$, $R_9$, $R'_9$, $R_{10}$, and $R'_{10}$ not forming said heterocycle are defined as above; or (v) one or more of $R_1$, $R'_1$, $R_2$, $R'_2$, $R_3$, $R'_3$, $R_4$, $R'_4$, $R_5$, $R'_5$, $R_6$, $R'_6$, $R_7$, $R'_7$, $R_8$, $R'_8$, $R_9$, $R'_9$, $R_{10}$, and $R'_{10}$, together with a different one of $R_1$, $R'_1$, $R_2$, $R'_2$, $R_3$, $R'_3$, $R_4$, $R'_4$, $R_5$, $R'_5$, $R_6$, $R'_6$, $R_7$, $R'_7$, $R_8$, $R'_8$, $R_9$, $R'_9$, $R_{10}$, and $R'_{10}$, which is attached to an atom in the pentaaza macrocycle is bound by a strap, to form a cycle or heterocycle, said strap represented by the formula:

$$-(C)_I\text{-}Q_A\text{-}(C)_J\text{-}Q_B\text{-}(C)_K\text{-}Q_C\text{-}(C)_L-$$

wherein

C is saturated, partially saturated or unsaturated; I, J, K and L are independently integers from 0 to 10; $G_A$, $Q_B$ and $Q_C$ are independently selected from the group consisting of alkenyl, alkenylcycloalkenyl, alkenylcycloalkyl, alkyl, alkylcycloalkenyl, alkylcycloalkyl, alkynyl, aralkyl, aryl, cycloalkenyl, cycloalkyl, cycloalkylalkyl, cycloalkylcycloalkyl, cycloalkenylalkyl, and heterocyclyl, wherein said heterocycyl is unsubstituted or substituted with aza, amide, ammonium, oxa, thia, sulfonyl, sulfinyl, sulfonamide, phosphoryl, phosphinyl, phosphino, phosphonium, keto, ester, alcohol, carbamate, urea, thiocarbonyl, borates, boranes, boraza, silyl, siloxy, silaza, halogens and any combination thereof; and any of $R_1$, $R'_1$, $R_2$, $R'_2$, $R_3$, $R'_3$, $R'_4$, $R_5$, $R'_5$, $R'_5$, $R_6$, $R'_6$, $R_7$, $R'_7$, $R_8$, $R'_8$, $R_9$, $R'_9$, $R_{10}$, and $R'_{10}$ not forming said cycle or heterocycle are defined as above; or (vi) combinations of any of (i) through (v) above; and wherein M is a transition metal;

X, Y and Z are independently selected from the group consisting of halide, oxo, aquo, hydroxo, alcohol, phenol, dioxygen, peroxo, hydroperoxo, alkylperoxo, arylperoxo, ammonia, alkylamino, arylamino, heterocycloalkyl amino, heterocycloaryl amino, amine oxides, hydrazine, alkyl hydrazine, aryl hydrazine, nitric oxide, cyanide, cyanate, thiocyanate, isocyanate, isothiocyanate, alkyl nitrile, aryl nitrile, alkyl isonitrile, aryl isonitrile, nitrate, nitrite, azido, alkyl sulfonic acid, aryl sulfonic acid, alkyl sulfoxide, aryl sulfoxide, alkyl aryl sulfoxide, alkyl sulfonic acid, aryl sulfenic acid, alkyl sulfinic acid, aryl sulfinic acid, alkyl thiol carboxylic acid, aryl thiol carboxylic acid, alkyl thiol thiocarboxylic acid, aryl thiol thiocarboxylic acid, alkyl carboxylic acid, aryl carboxylic acid, urea, alkyl urea, aryl urea, alkyl aryl urea, thiourea, alkyl thiourea, aryl thiourea, alkyl aryl thiourea, sulfate, sulfite, bisulfate, bisulfite, thiosulfate, thiosulfite, hydrosulfite, alkyl phosphine, aryl phosphine, alkyl phosphine oxide, aryl phosphine oxide, alkyl aryl phosphine oxide, alkyl phosphine sulfide, aryl phosphine sulfide, alkyl aryl phosphine sulfide, alkyl phosphonic acid, aryl phosphoric acid, alkyl phosphinic acid, aryl phosphinic acid, alkyl phosphinous acid, aryl phosphinous acid, phosphate, thiophosphate, phosphite, pyrophosphite, triphosphate, hydrogen phosphate, dihydrogen phosphate, alkyl guanidino, aryl guanidino, alkyl aryl guanidino, alkyl carbamate, aryl carbamate, alkyl aryl carbamate, alkyl thiocarbamate, aryl thiocarbamate, alkylaryl thiocarbamate, alkyl dithiocarbamate, aryl dithiocarbamate, alkylaryl dithiocarbamate, bicarbonate, carbonate, perchlorate, chlorate, chlorite, hypochlorite, perbromate, bromate, bromite, hypobromite, tetrahalomanganate, tetrafluoroborate, hexafluoroantimonate, hypophosphite, iodate, periodate, metaborate, tetraaryl borate, tetra alkyl borate, tartrate, salicylate, succinate, citrate, ascorbate, saccharinate, amino acid, hydroxamic acid, thiotosylate, and anions of ion exchange resins, or the corresponding anions thereof; or X, Y and Z are independently selected from the group consisting of charge—neutralizing anions which are derived from any monodentate or polydentate coordinating ligand and a ligand system and the corresponding anion thereof; or X, Y and Z are independently attached to one or more of $R_1$, $R'_1$, $R_2$, $R'_2$, $R_3$, $R'_3$, $R_4$, $R'_4$, $R_5$, $R'_5$, $R_6$, $R'_6$, $R_7$, $R'_7$, $R_8$, $R'_8$, $R_9$, $R'_9$, $R_{10}$, and $R'_{10}$; and n is an integer from 0 to 3; and at least one of said bond of ($i^b$), said moeity of said moeity of ($i^c$), said cycle or heterocycle of (ii), said cycle or heterocycle of (iii), said heterocycle of (iv) or said cycle or heterocycle of (v) independently forms a link from $G_A$ to $G_5$; and (b) $G_5$ is a bond or a linking moiety, wherein said linking moiety comprises an atom selected from the group consisting of S, O, N, P, C and any combination thereof; and (c) $G_C$ is a moeity having formula —(OCH$_2$CH$_2$)—R$_{13}$, —(CH$_2$CH$_2$O)$_f$—R$_{13}$, or —CH$_3$O—(CH$_2$CH$_2$O)$_f$—R$_{13}$, of combinations thereof, wherein f is an integer from 7 to about 1,000 and $R_{13}$ is a bond or is selected from the group consisting of H, alkenyl, alkenylcycloalkenyl, alkenylcycloalkyl alkyl, alkylcycloalkenyl, alkylcycloalkyl alkynyl, aralkyl, aryl, cycloalkenyl, cycloalkyl, cycloalkylalkyl, cycloalkylcycloalkyl, cycloalkenylalkyl, heterocyclyl, —OR$_{11}$, —NR$_{11}$R$_{12}$, —COR$_{11}$, —CO$_2$R$_{11}$, —CONR$_{11}$R$_{12}$, —SR$_{11}$, —SOR$_{11}$, —SO$_2$R$_{11}$, —SO$_2$NR$_{11}$R$_{12}$, —N(OR$_{11}$)(R$_{12}$), —P(O)(OR$_{11}$)(OR$_{12}$), —P(O)(OR$_{11}$(R$_{12}$), —OP(O)(OR$_{11}$)(OR$_{12}$), $R_{14}$—(CH$_2$)$_2$—H, (CH$_2$)$_g$—H, $G_A$, (CH$_2$)$_g$—R$_{14}$-$G_A$, and O—C—ONH(CH$_2$)$_g$—R$_{14}$-$G_A$, wherein $G_A$, $R_{11}$ and $R_{12}$ are as defined above, wherein g is an integer from 0 to about 500, and wherein $R_{14}$ is selected from the group consisting of S, N, O, P, and C.

In another aspect, a PEGylated superoxide dismutase mimetic wherein $G_A$ is of Formula II:

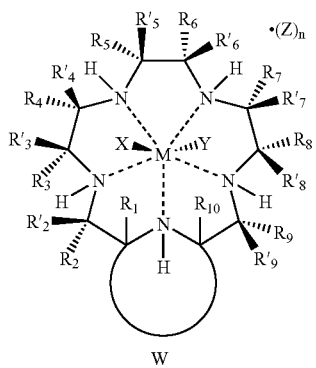

wherein a nitrogen of the pentaaza macrocycle and two adjacent carbon atoms to which the nitrogen is attached independently form a nitrogen-containing heterocycle W which (a) is substituted or unsubstituted; (b) is saturated, partially saturated or unsaturated, in which case the hydrogen attached to the nitrogen which is both part of the unsaturated heterocycle and the pentaaza macrocycle and the R groups attached to the carbon atoms which are both pad of the heterocycle and the macrocycle are absent; and (c) comprises 2 to 20 carbon atoms.

A compound as above, wherein one or more of $R_1$, $R_2$, $R'_2$, $R_3$, $R'_3$, $R_4$, $R'_4$, $R_5$, $R'_5$, $R_6$, $R'_6$, $R_7$, $R'_7$, $R_8$, $R'_8$, $R_9$, $R'_9$, and $R_{10}$ together with an atom of the heterocycle W are independently bound by a strap to form a cycle or heterocycle, said strap represented by the formula:

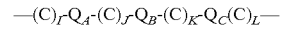

wherein

C is saturated, partially saturated or unsaturated; I, J, K and L are independently integers from 0 to 10; $Q_A$, $Q_B$ and $Q_C$ are independently selected from the group consisting of alkenyl, alkenylcycloalkenyl, alkenylcycloalkyl, alkyl, alkylcycloalkenyl, alkylcycloalkyl, alkynyl, aralkyl, aryl, cycloalkenyl, cycloalkyl, cycloalkylalkyl, cycloalkylcycloalkyl, cycloalkenylalkyl, and heterocyclyl, wherein said heterocyclyl is unsubstituted or substituted with aza, amide, ammonium, oxa, thia, sulfonyl, sulfinyl, sulfonamide, phosphoryl, phosphinyl, phosphino, phosphonium, keto, ester, alcohol, carbamate, urea, thiocarbonyl, borates, boranes, boraza, silyl, siloxy, silaza, halogens and any combination thereof.

A PEGylated superoxide dismutase mimetic wherein $G_A$ is of Formula III:

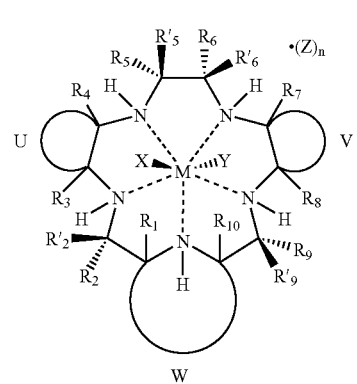

wherein two sets of two adjacent carbon atoms of the macrocycle independently form cycles or heterocycles U and V which (a) are substituted or unsubstituted, (b) are saturated, partially saturated or unsaturated, and (c) comprise 3 to 20 carbon atoms.

A compound as above wherein one or more of $R_1$, $R_2$, $R'_2$, $R_3$, $R'_3$, $R_4$, $R'_4$, $R_5$, $R'_5$, $R_6$, $R'_6$, $R_7$, $R_8$, $R_9$, $R'_9$, and $R_{10}$ together with an atom of the heterocycle W, cycle or heterocycle U, and cycle or heterocycle V are independently bound by a strap to form a cycle or heterocycle, said strap represented by the formula:

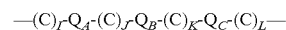

wherein

C is saturated, partially saturated or unsaturated; I, J, K and L are independently integers from 0 to 10; $Q_A$, $Q_B$ and $Q_C$ are independently selected from the group consisting of alkenyl, alkenylcycloalkenyl, alkenylcycloalkyl, alkyl, alkylcycloalkenyl, alkylcycloalkyl, alkenyl, aralkyl, aryl, cycloalkenyl, cycloalkyl, cycloalkylalkyl, cycloalkylcycloalkyl, cycloalkenylalkyl, and heterocyclyl, wherein said heterocyclyl is unsubstituted or substituted with aza, amide, ammonium, oxa, thia, sulfonyl, sulfinyl, sulfonamide, phosphoryl, phosphinyl, phosphino, phosphonium, keto, ester, alcohol, carbamate, urea, thiocarbonyl, borates, boranes, boraza, silyl, siloxy, silaza, halogens and any combination thereof.

A linking moeity ($G_B$) covalently attaching at least a polyethylene glycol to at least a superoxide dismutase moeity is contemplated. This moeity can be a bond or any compound, as described above, and is not limited to these following moeities. Examples of possible moeities include, but are not limited to those described in Table 1:

TABLE 1

Moeities for $G_B$

—O—CO—NH—
—NH—
—O—CO—CH$_2$—CH$_2$—CO—NH—
—O—CH$_2$—CO—NH—NH—CO—
—O—CO—O—

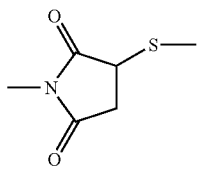

—S—S—
—S—
—S—CH$_2$—CH$_2$—NH—CO—O—
—S—CH$_2$—CH$_2$—
—O—CO—NH—CH$_2$—CH$_2$ S—
—S—CH$_2$—CH$_2$—NH—CO—CH$_2$—CH$_2$—
—S—CH$_2$—CH$_2$—NH—CH$_2$—CH$_2$—CH$_2$—CH$_2$—
—CO—NH—

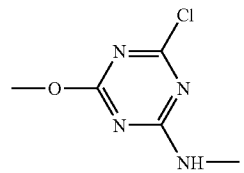

—O—
—O—CO—CH$_2$—CH$_2$—CH$_2$—CO—NH—
—O—CH$_2$—CH(OH)—CH$_2$—O—
—NH—CO—O—
—SO$_2$—CH$_2$—CH$_2$—S—
—NH—CO—CH$_2$—S—
—CH$_2$—CH$_2$—S—
—CO—NH—CH$_2$—CH$_2$—S—
—S—CH$_2$—CH$_2$ NH—CO—
—S—CH$_2$—CH$_2$ NH—CO—NH—CH$_2$—CH$_2$—
—S—CH$_2$—CH$_2$—NH—CO—CH$_2$—CH$_2$—CH$_2$—O—
—S—CH$_2$—CH$_2$—NH—CO $G_B$ is not limited to these moieties, and should be construed broadly, the above examples are meant only to be representative of a much broader class, which is defined above. Other examples of classes of compounds include a compounds as above wherein $G_B$ is a moiety independently selected from the group consisting of —OR$_{11}$, —NR$_{11}$R$_{12}$, —COR$_{11}$, —CO$_2$R$_{11}$, —CONR$_{11}$R$_{12}$, —SR$_{11}$, —SOR$_{11}$, —SO$_2$R$_{11}$, —SO$_2$NR$_{11}$R$_{12}$, —N(OR$_{11}$)(R$_{12}$), —P(O)(OR$_{11}$)(OR$_{12}$), —P(O)(OR$_{11}$)(R$_{12}$), —OP(O)(OR$_{11}$)(OR$_{12}$), R$_{11}$NC(O)R$_{12}$, R$_{11}$NC(O)R$_{12}$ and substituents attached to the α-carbon of α-amino adds, wherein R$_{11}$ and R$_{12}$ are independently hydrogen or alkyl.

Further examples of PEGylated superoxide dismutase mimetics include compounds having more than one $G_B$ and $G_C$, for example a formula selected from Table 2:

TABLE 2

Compounds which include a $G_A$ and at least one $G_B$ and $G_C$.

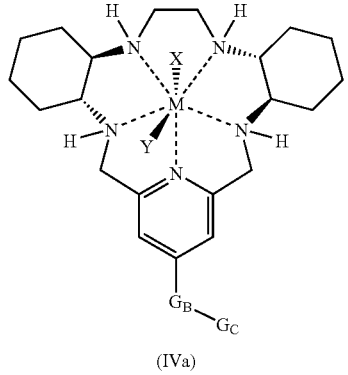

(IVa)

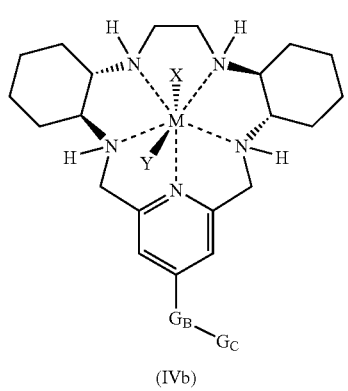

(IVb)

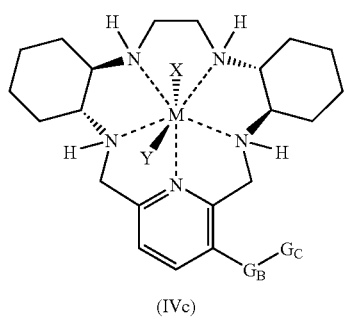

(IVc)

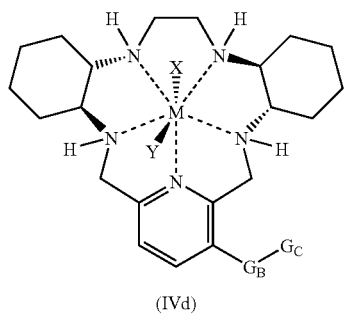

(IVd)

TABLE 2-continued

Compounds which include a $G_A$ and at least one $G_B$ and $G_C$.

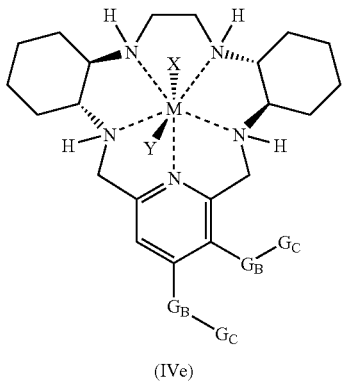

(IVe)

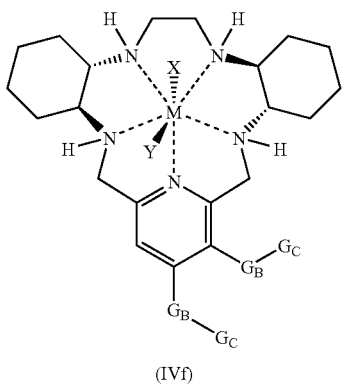

(IVf)

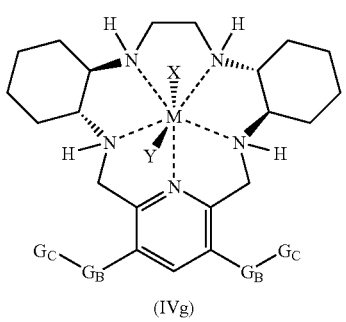

(IVg)

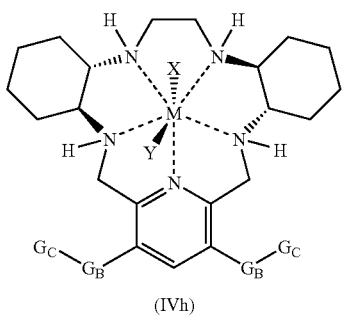

(IVh)

A PEGylated superoxide dismutase mimetic wherein $G_C$ of IVa, IVb, IVc, and IVd comprises, for example, from 7 to about 1,000 ethylene glycol monomers, from about 10 to about 500 ethylene glycol monomers, from about 15 to about 250 ethylene glycol monomers, from about 20 to about 100 ethylene glycol monomers, from about 25 to about 50 ethylene glycol monomers.

A PEGylated superoxide dismutase mimetic wherein each $G_C$ of IVe, IVf, IVg, and IVh independently comprises from 7 to about 1,000 ethylene glycol monomers, from about 10 to about 500 ethylene glycol monomers, from about 15 to about 250 ethylene glycol monomers, from about 20 to about 100 ethylene glycol monomers, from about 25 to about 50 ethylene glycol monomers.

A PEGylated superoxide dismutase mimetic ($G_A$) having a chelated ion (M), wherein the ion is Mn, Fe, Ni, Cu and V. These compounds can, for example, chelate a magnesium ion and create a compound from Table 3.

TABLE 3

Compounds of $G_A$ which can be PEGylated

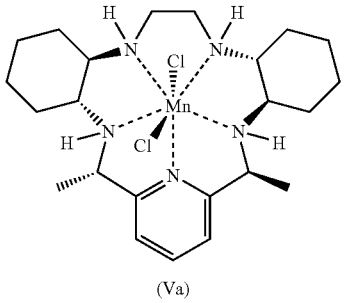

(Va)

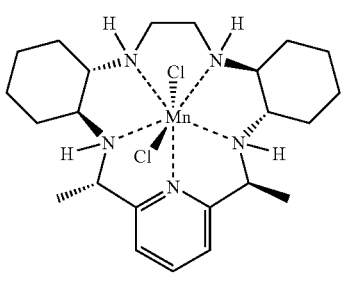

(Vb)

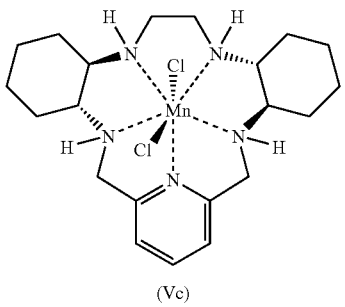

(Vc)

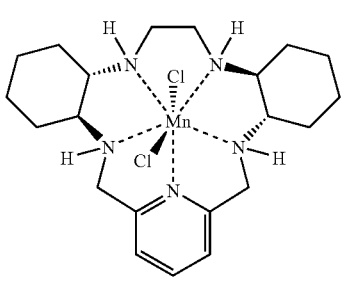

(Vd)

A PEGylated superoxide dismutase mimetic as above can, for example, be of a formula represented in Table 4.

TABLE 4
$G_A$ and $G_C$ containing compounds
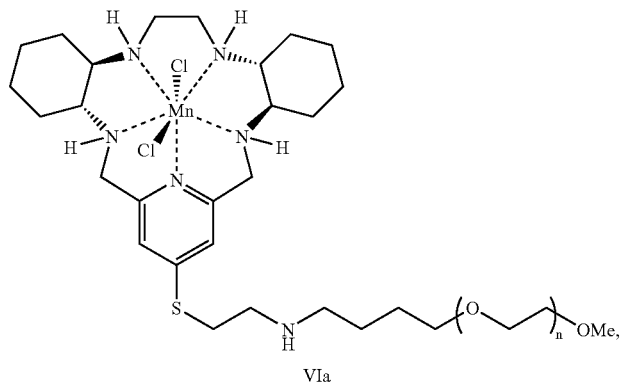
VIa
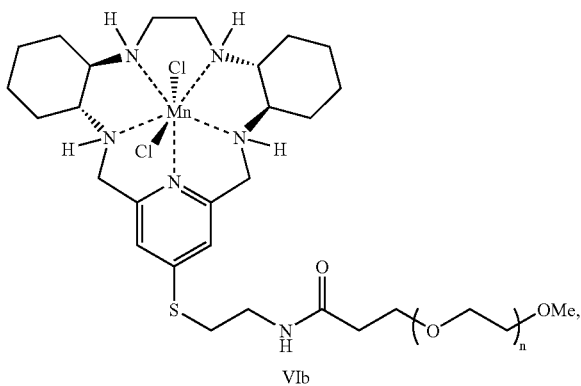
VIb
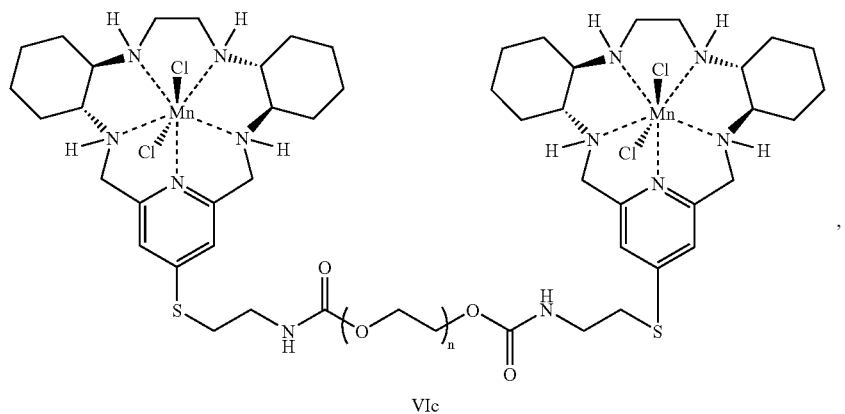
VIc
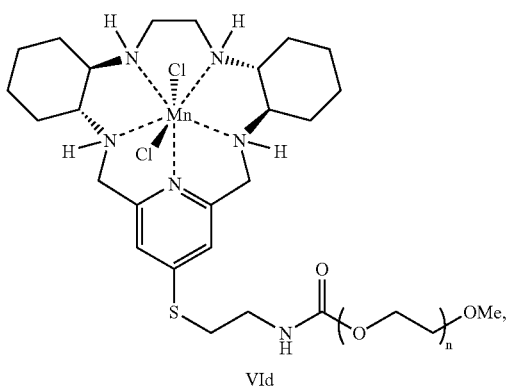
VId TABLE 4-continued
G_A and G_C containing compounds
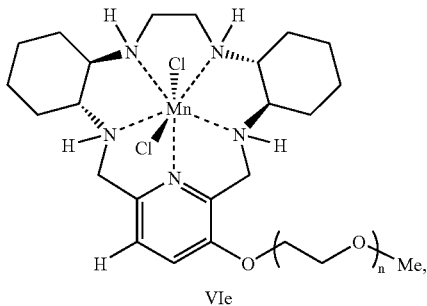
VIe
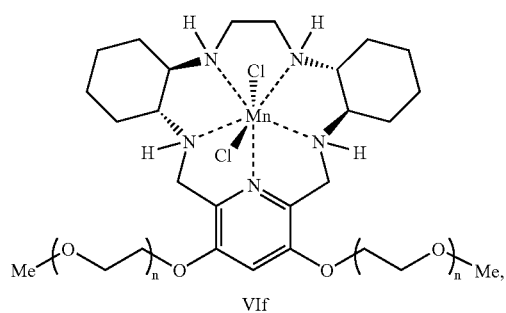
VIf
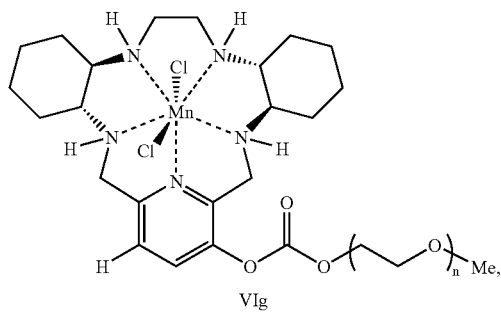
VIg
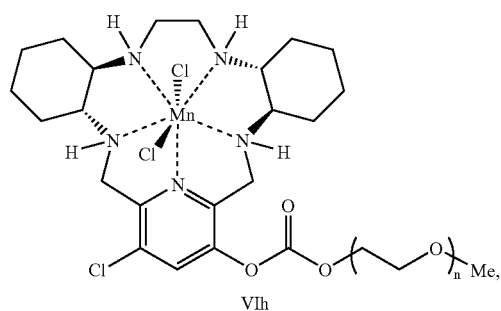
VIh
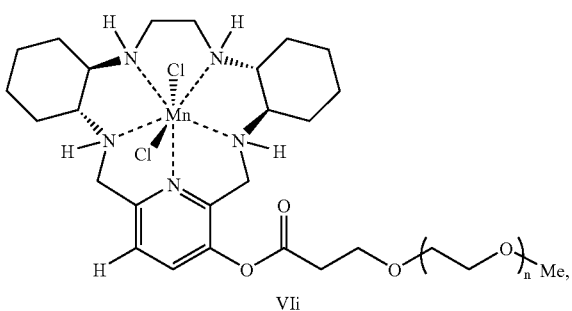
VIi TABLE 4-continued
$G_A$ and $G_C$ containing compounds
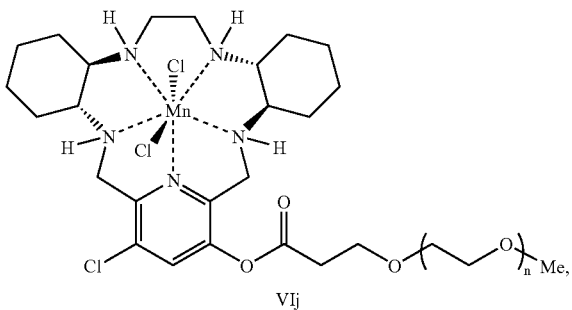
VIj
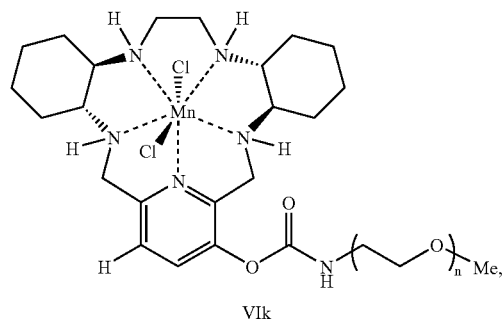
VIk
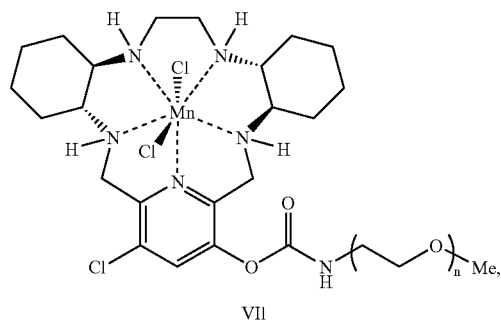
VIl
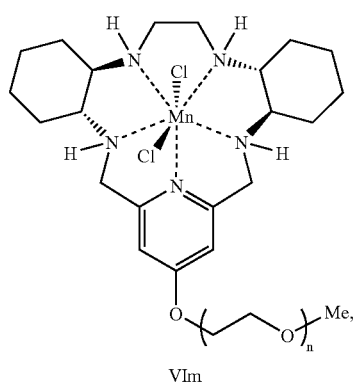
VIm TABLE 4-continued
G$_A$ and G$_C$ containing compounds
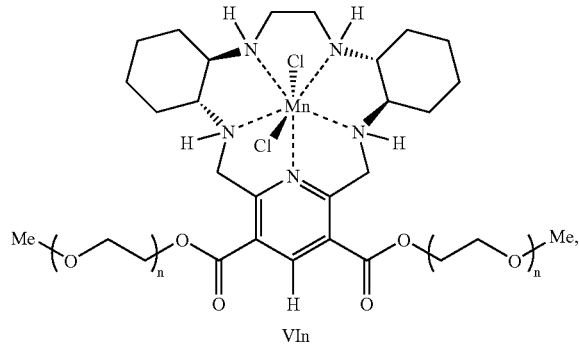
VIn
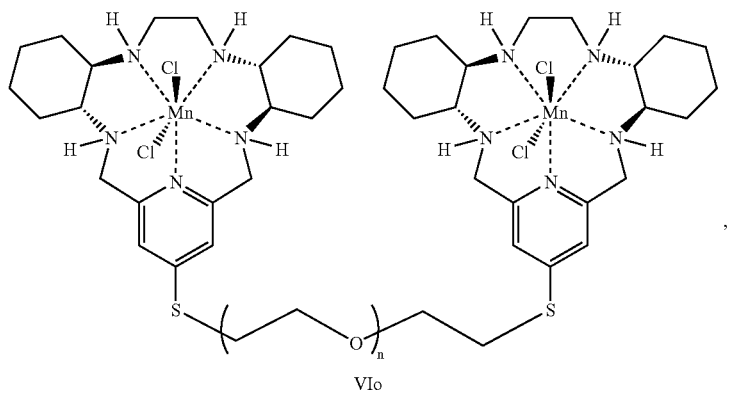
VIo
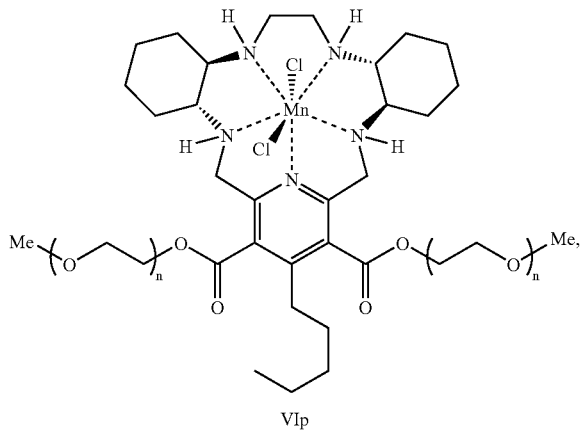
VIp
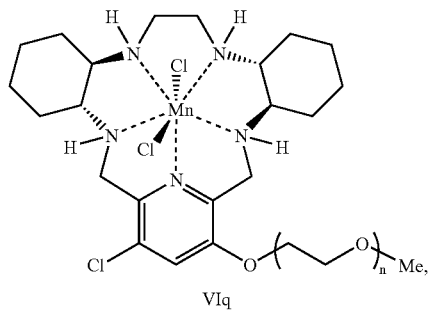
VIq TABLE 4-continued
G$_A$ and G$_C$ containing compounds
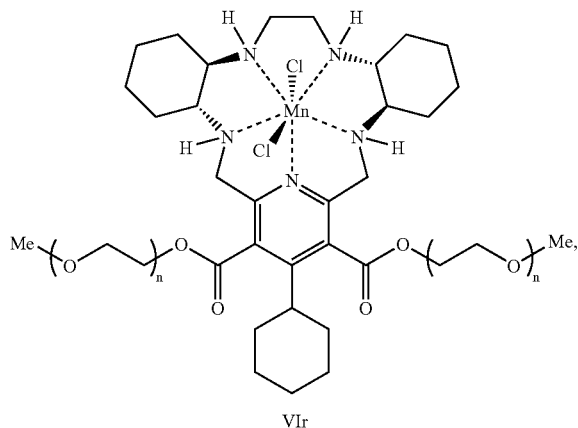
VIr
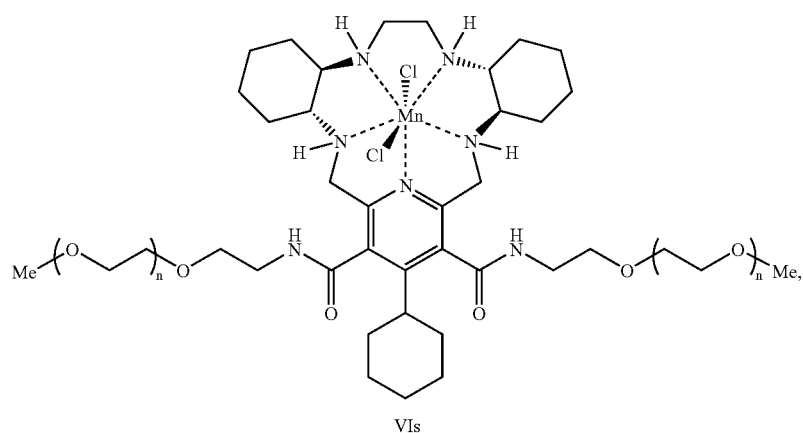
VIs
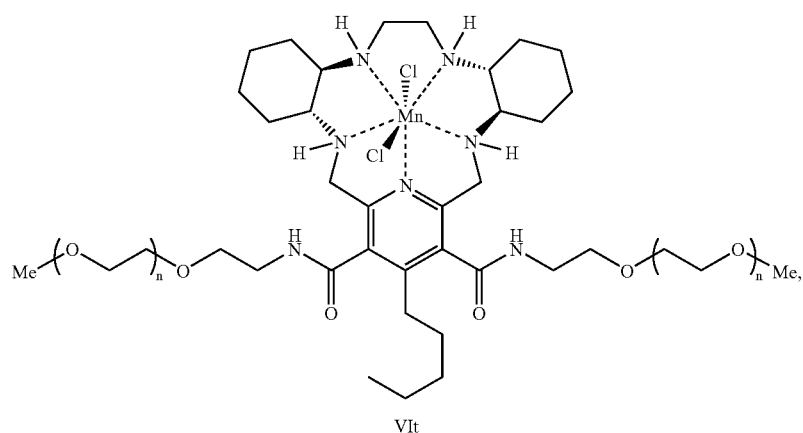
VIt TABLE 4-continued
$G_A$ and $G_C$ containing compounds
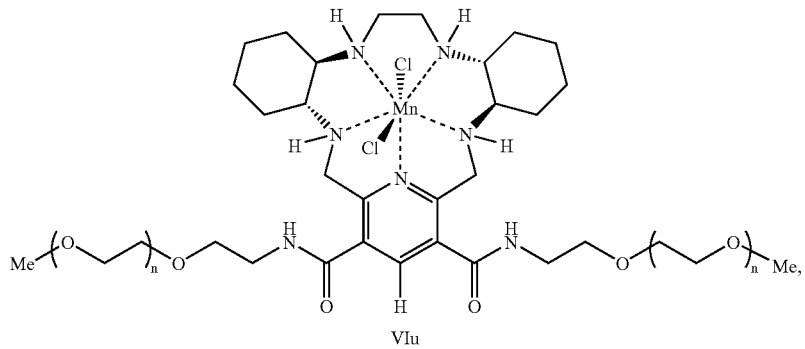
VIu
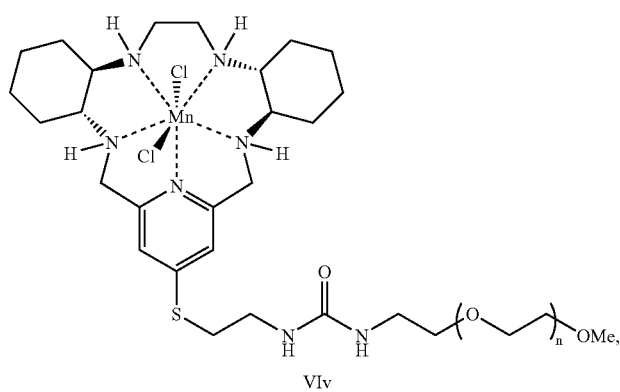
VIv
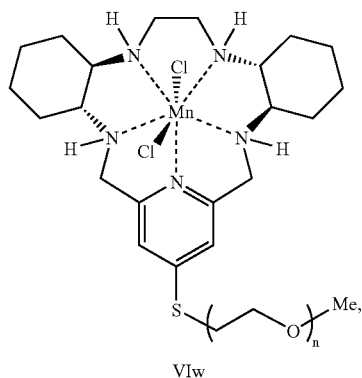
VIw
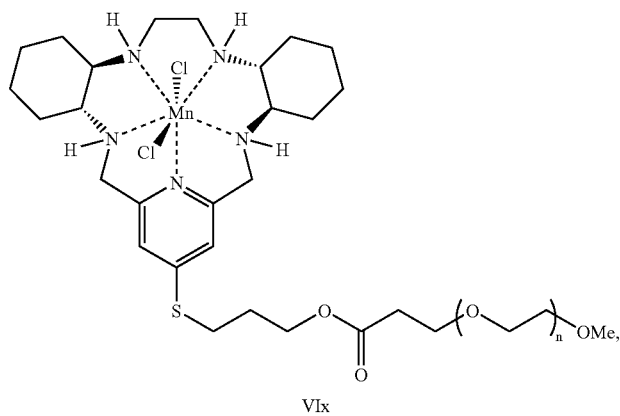
VIx TABLE 4-continued
$G_A$ and $G_C$ containing compounds
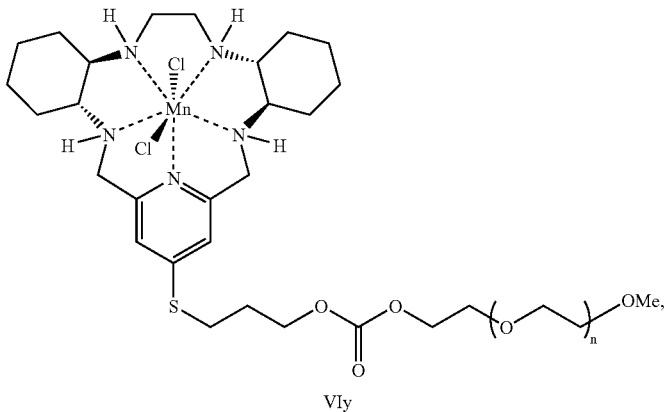
VIy
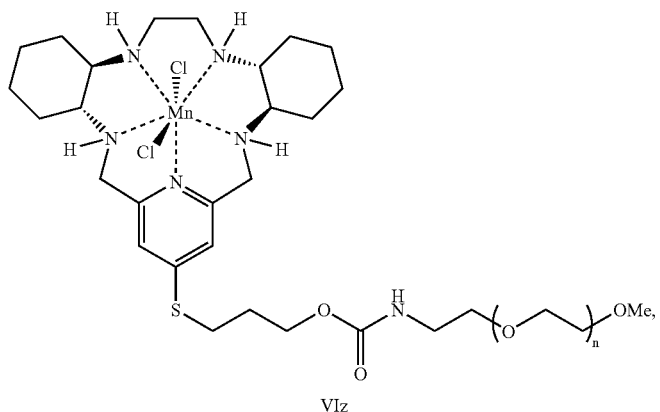
VIz
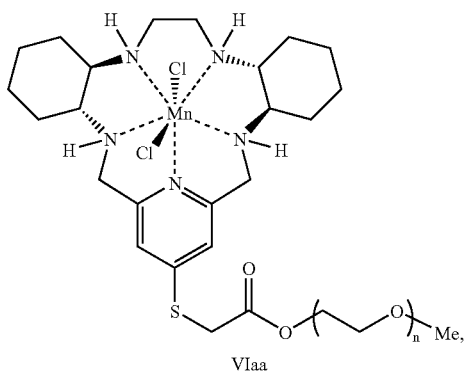
and
VIaa
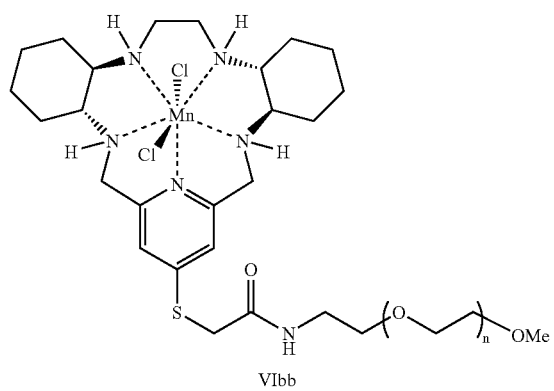
VIbb The polyethylene glycol ($G_C$) can be, for example, any length or molecular weight, but can also be, for example, a molecule wherein n is an integer, for example, from about 7 to about 1,000, from about 10 to about 500, from about 15 to about 250, from about 20 to about 100, from about 25 to about 50, wherein n is about 23, wherein n is about 45, wherein n is about 114, or wherein n is about 455.

A compound as above, wherein the polyethylene glycol has a molecular weight from about 200 Da to about 44 kDa, from about 2500 Da to about 40 kDa, from about 1 kDa to about 35 kDa, from about 5 kDa to about 25 kDa, from about 800 Da to about 1200 Da, from about 1800 Da to about 2200 Da, from about 4800 Da to about 5200 Da, from about 9800 Da to about 10,200 Da, or from about 1900 Da to about 2100 Da.

The molecular weight distribution can be characterized by the polydispersity index of the polymer composition. The polydispersity index can be calculated as the ratio of the weight average molecular weight to the number average molecular weight and the values for the polymer.

A PEGylated superoxide dismutase mimetic having the formula is specifically provided:

VII

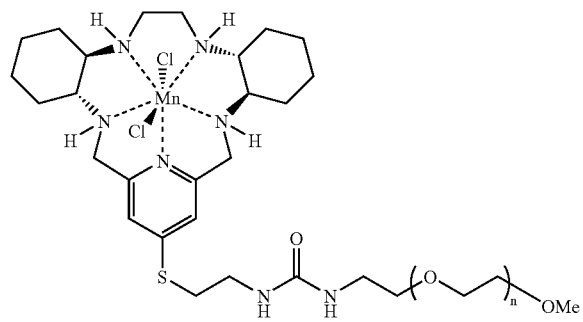

wherein n is an integer, for example, from about 7 to about 1,000, from about 10 to about 500, from about 15 to about 250, from about 20 to about 100, from about 25 to about 50, wherein n is about 23, wherein n is about 45, wherein n is about 114, or wherein n is about 455.

A compound as above, wherein the polyethylene glycol has a molecular weight from about 200 Da to about 44 kDa, from about 2500 Da to about 40 kDa, from about 1 kDa to about 35 kDa, from about 5 kDa to about 25 kDa, from about 800 Da to about 1200 Da, from about 1800 Da to about 2200 Da, from about 4800 Da to about 5200 Da, from about 9800 Da to about 10,200 Da, or from about 1900 Da to about 2100 Da.

A PEGylated superoxide dismutase mimetic as above, can, for example, have a formula:

VIII

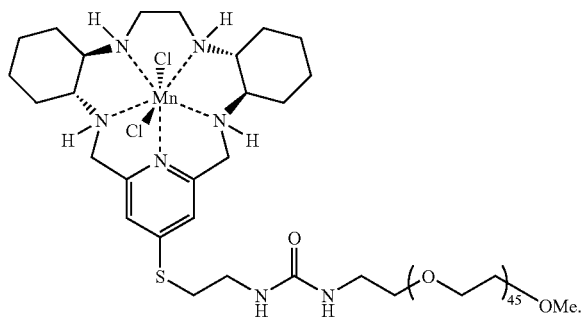

Also provided is a PEGylated superoxide dismutase mimetic having a formula:

$$G_A\text{-}(G_B\text{-}G_C)_h$$

comprising one A moeity having a plurality of $G_B$-$G_C$ moieties attached thereto, wherein $G_A$, $G_B$ and $G_C$ are independently as defined above, and h is an integer from 1 to about 1,000.

A compound as above, further comprising one or more $G_A$ or $G_C$ moieties attached to each $G_B$ moeity, said compound having a formula:

$$G_A\text{-}(G_B\text{-}(P)_d)_m$$

wherein each P is independently $G_C$ or $G_A$, d is an integer from 1 to about 100, and m is an integer from 1 to about 20.

A compound according as above, further comprising at least one $G_B$-$G_A$ moiety attached to one or more of said $G_C$ moiety, and having a formula:

$$G_A\text{-}(G_B\text{-}G_C\text{-}(G_B\text{-}G_A)_m)_p$$

wherein m is an integer from 1 to about 1,000 and p is an integer from 1 to about 1,000.

A compound as above, further comprising at least one $G_B$-$G_A$ moiety attached to one or more of said $G_C$ moiety, and having a formula:

$$(G_B\text{-}G_C)_e\text{-}(G_B\text{-}G_A)_n)_p$$

wherein n is an integer from 1 to about 1,000, p is an integer from 1 to about 100 and e is an integer from 1 to about 1,000.

A compound as above further comprising at least one $G_B$-$G_A$ moiety attached to one or more $G_A$, $G_B$, and/or $G_C$ moiety.

A compound as above, wherein at least one $G_B$-$G_A$ moiety is attached to one or more $G_A$, $G_B$, and/or $G_C$ moeities.

The compounds above are examples of many possible compounds which contain $G_A$, $G_B$, and $G_C$ and are not meant to be limiting. Any and all compounds comprising these constituents are contemplated. These include, for example, a branched chain molecule in which $G_A$, $G_B$, and $G_C$ are combined to create a novel compound. This branched compound can comprise many arms extending from a central $G_A$, $G_B$, or $G_C$. Each branch can contain $G_A$, $G_B$, and $G_C$ alone or in combination. The compound can also, for example, be in the form of a multi-armed, multi-branched linking moiety whereby any number of $G_A$ and $G_C$ can be linked. The compound can be a superoxide dismutase mimetic linked to at least one polyethylene glycol, wherein at least one of said polyethylene glycol comprises seven or more ethylene glycol monomers.

A PEGylated superoxide dismutase mimetic wherein $G_B$ is a multi-arm linking moeity, linking at least one $G_A$ moeity and at least one $G_C$ moeity.

A compound as above wherein $G_B$ is a pentaerythritol based multi-arm linking moeity linking from 1 to 4 $G_A$ and $G_C$ moieties. Pentaaerythritol is a tatrahydric neopentyl alcohol.

A compound as above wherein the multi-arm linking moeity ($G_B$) is a sorbitol-based multi-arm linking moiety linking from 1 to 6 $G_A$ and $G_C$ moieties. Sorbitol is a polyol (sugar alcohol).

In a further aspect, a superoxide dismutase mimetic is provided wherein $G_A$ is linked to $G_B$, wherein $G_A$ is a superoxide dismutase mimetic, and may be a pentaaza macrocycle and $G_B$ is selected from the group consisting of Table 1 above.

Mixtures Including Superoxide Dismutase Mimetics

Mixtures including $G_A$, $G_B$, and $G_C$ are aspects of the current invention. These mixtures encompass, but are not limited to, placing the products together in a condition to allow a chemical reaction to take place, for instance creating a compound which includes $G_A$, $G_B$ and $G_C$.

In another aspect, a mixture comprising $G_A$, $G_B$, and $G_C$, wherein $G_A$ is a reaction product of an addition, elimination, or replacement reaction or any combination thereof, of at least one atom of the pentaaza macrocycle, wherein said pentaaza macrocycle is of a formula represented in Table 5;

TABLE 5

Representative compounds which include $G_A$

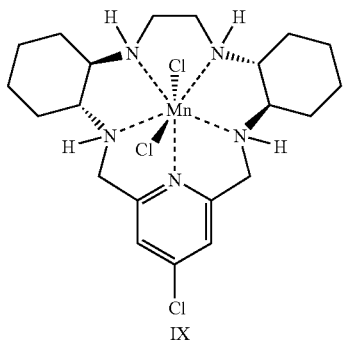

IX

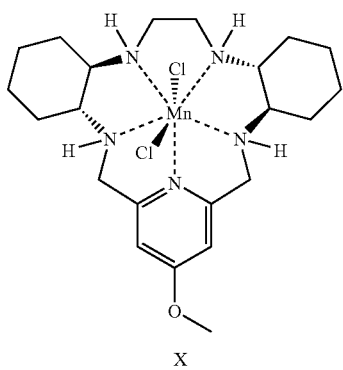

X

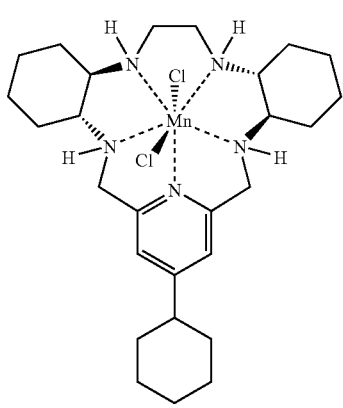

XI

TABLE 5-continued

Representative compounds which include $G_A$

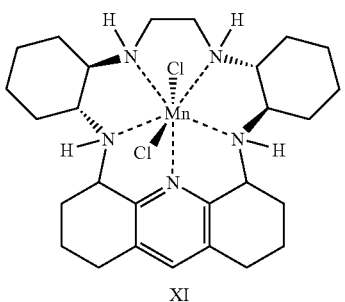

XI

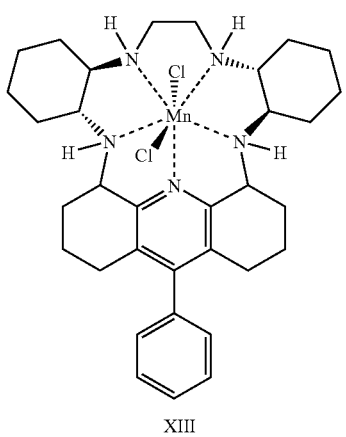

XIII

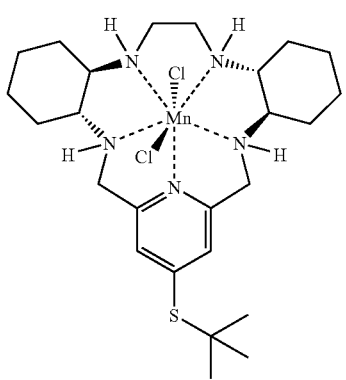

XIV

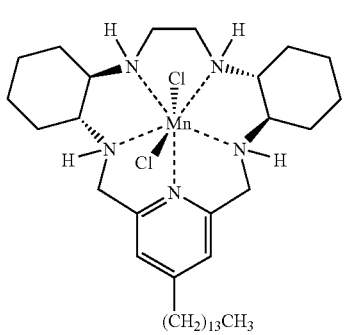

XV

TABLE 5-continued
Representative compounds which include $G_A$
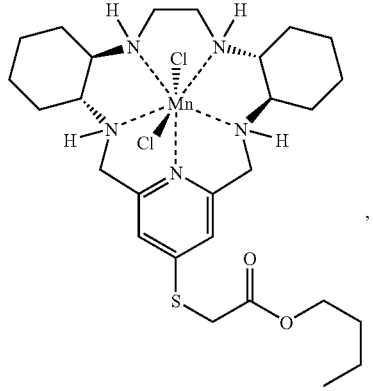
XVI
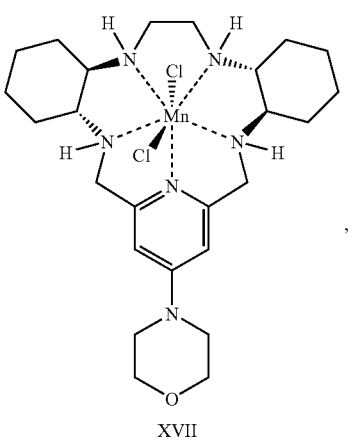
XVII
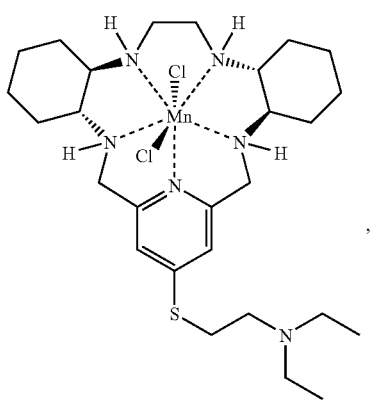
XVIII
TABLE 5-continued
Representative compounds which include $G_A$
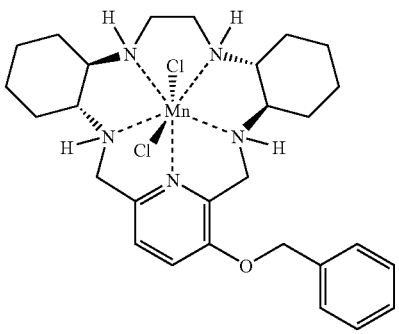
XIX
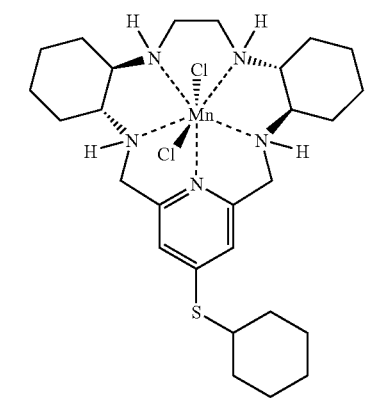
XX
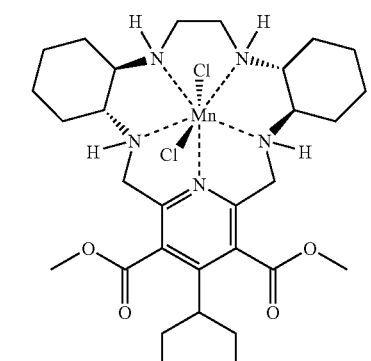
XXI
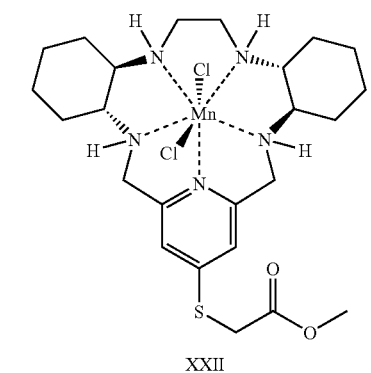
XXII TABLE 5-continued
Representative compounds which include $G_A$
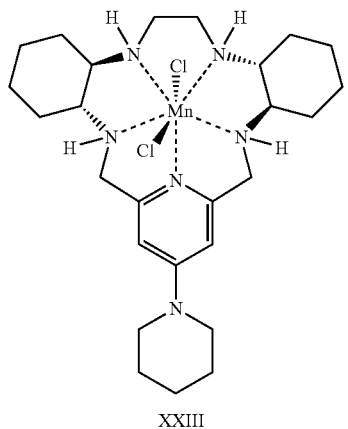
XXIII
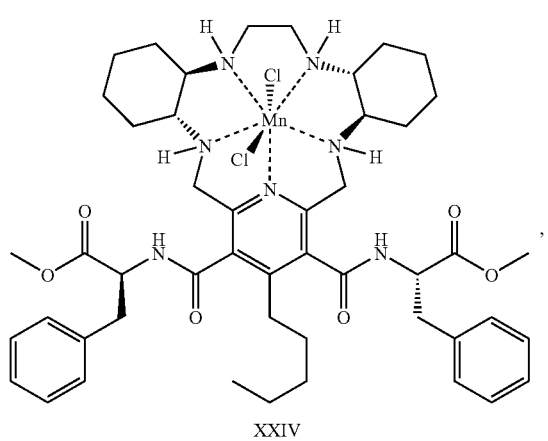
XXIV
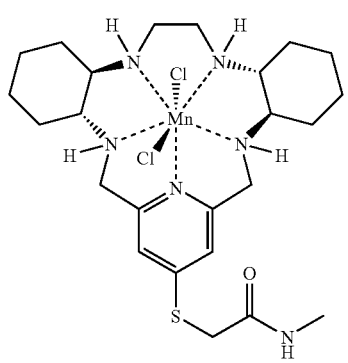
XXV
TABLE 5-continued
Representative compounds which include $G_A$
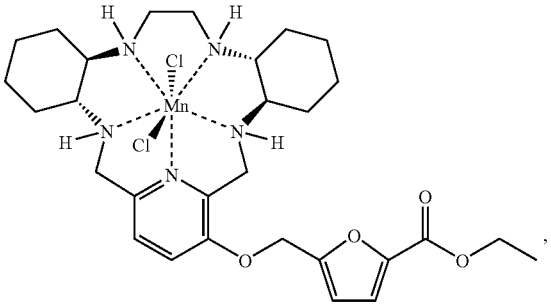
XXVI
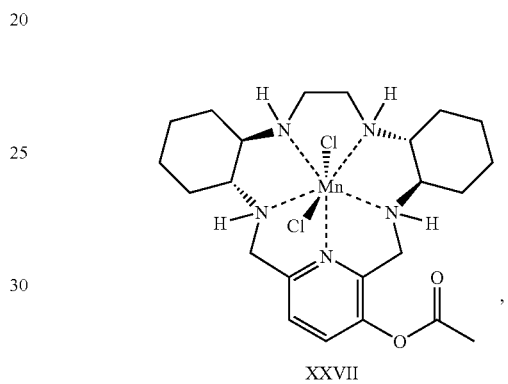
XXVII
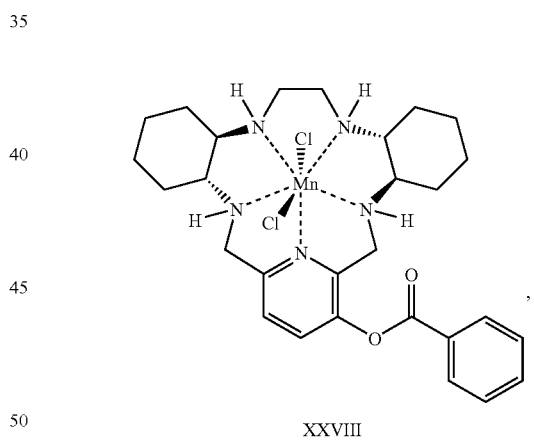
XXVIII
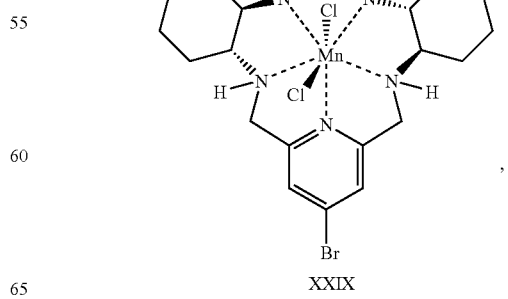
XXIX TABLE 5-continued
Representative compounds which include $G_A$
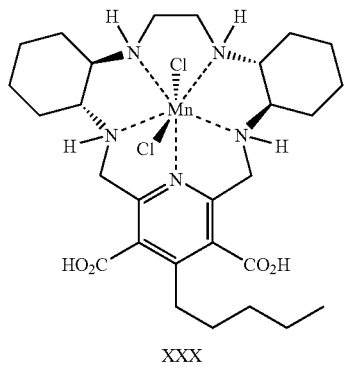
XXX
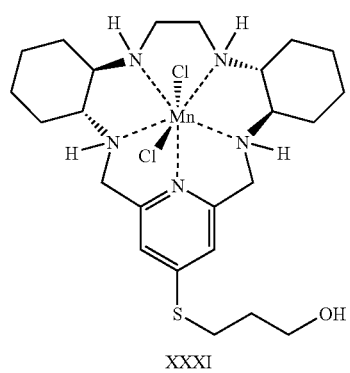
XXXI
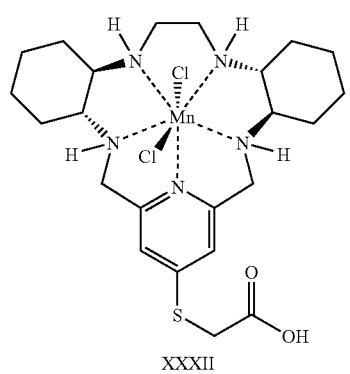
XXXII
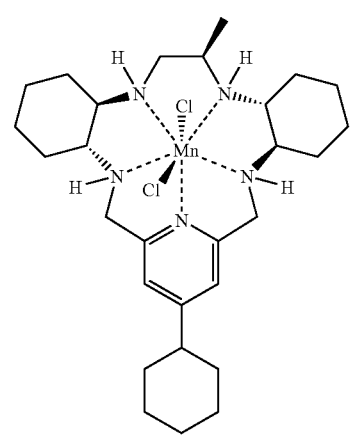
XXXIII
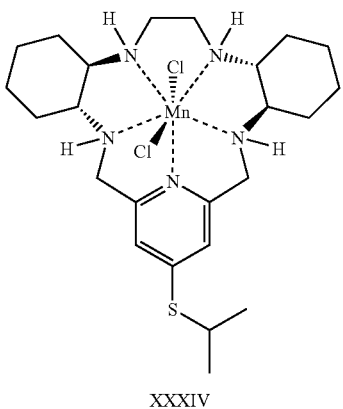
XXXIV
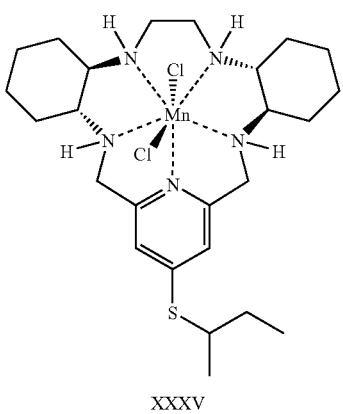
XXXV
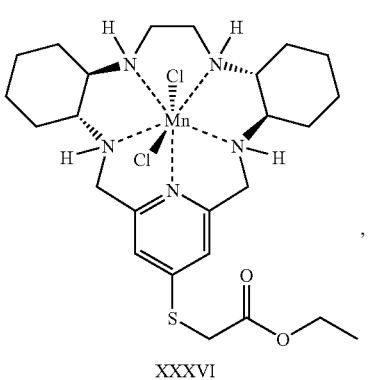
XXXVI TABLE 5-continued
Representative compounds which include $G_A$
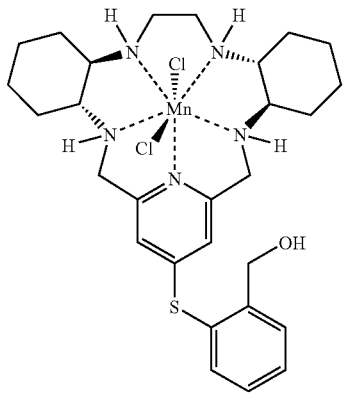
XXXVII
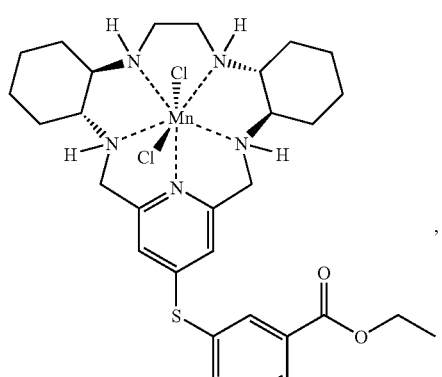
XXXVIII
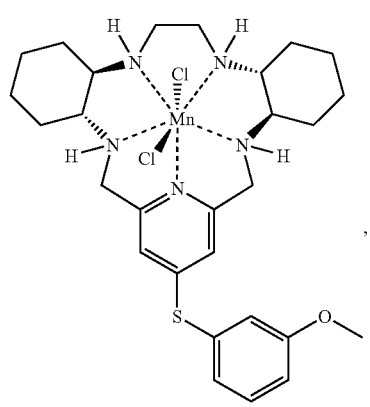
XXXIX
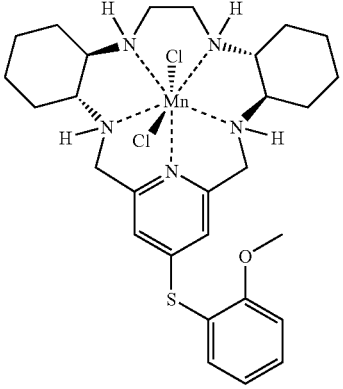
XL
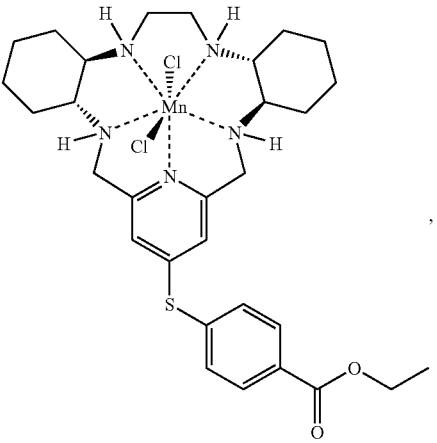
XLI
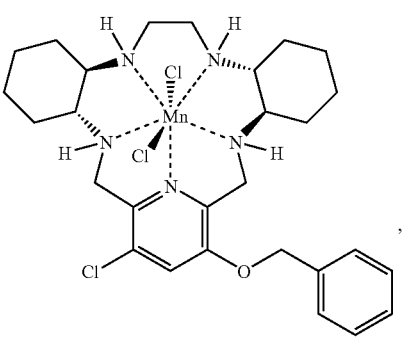
XLII TABLE 5-continued
Representative compounds which include $G_A$
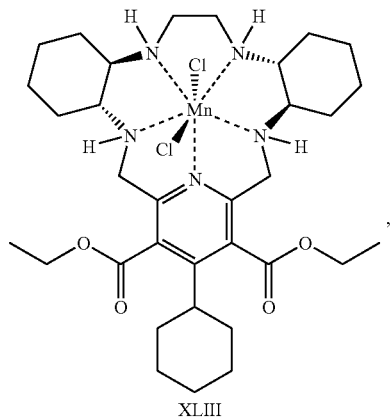
XLIII
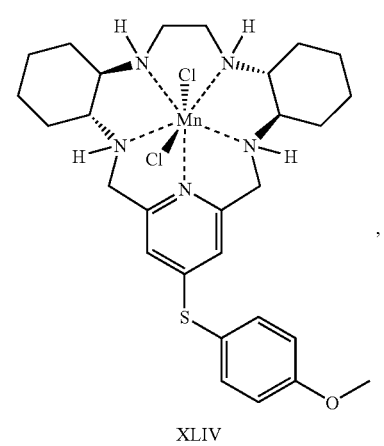
XLIV
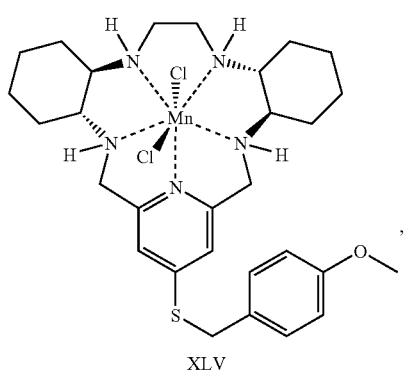
XLV
TABLE 5-continued
Representative compounds which include $G_A$
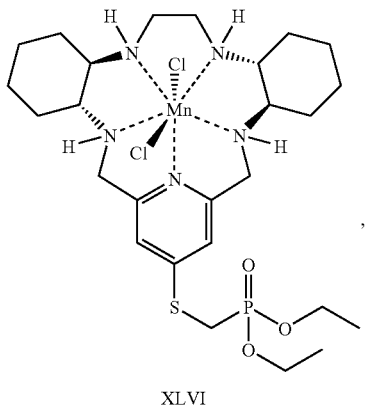
XLVI
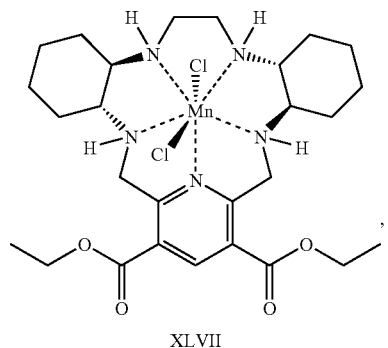
XLVII
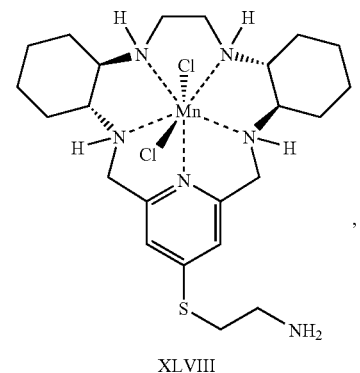
XLVIII
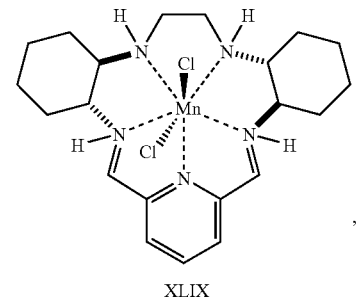
XLIX

TABLE 5-continued

Representative compounds which include $G_A$

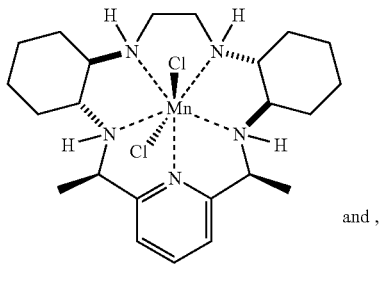

L

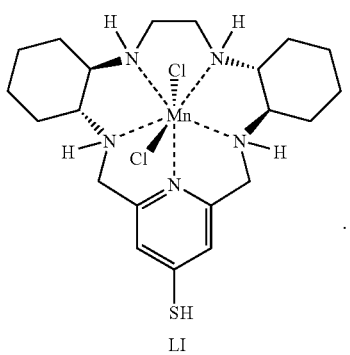

LI

Examples of above addition, elimination, replacement and combination reactions include, but are not limited to, direct conjugation, hydrolysis, nucleophilic attack and catalytic hydrogenation. One non-limiting example of combination reaction includes a reduction, which is both an addition and elimination reaction.

A mixture comprising $G_A$, $G_B$, and $G_C$, wherein $G_A$ is a reaction product of an addition, elimination, or replacement reaction or any combination thereof, of at least one atom of the pentaaza macrocycle, wherein said activated pentaaza macrocycle further comprising a halogen or a carboxylic acid.

A mixture as above wherein $G_A$ is an activated pentaaza macrocycle, said activated pentaaza macrocycle comprising a pentaaza macrocycle having a formula:

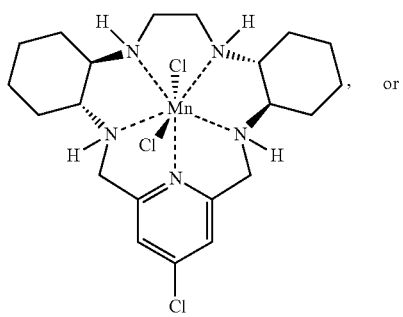

IX

, or

A mixture as above wherein the pentaaza macrocycle is of the formula:

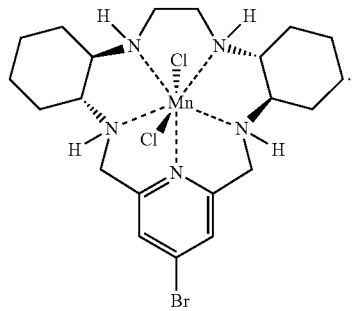

XXIX

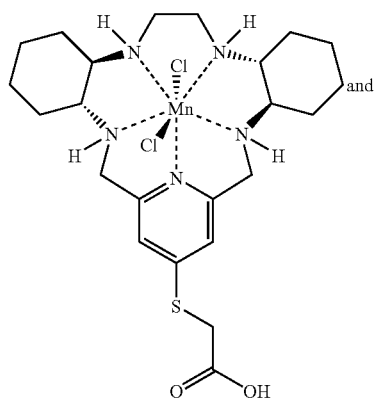

XXXII and

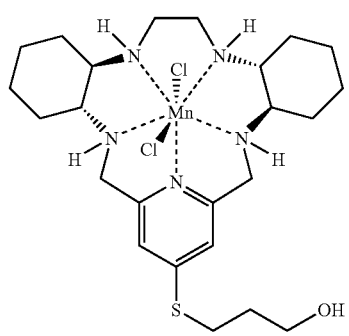

XXXI

Methods of Use of PEGylated Superoxide Dismutase Mimetics

A method for treating a disease or disorder affected by superoxide dismutase activity, the method comprising administering a therapeutically effective amount of a compound comprising a superoxide dismutase mimetic covalently linked to a polyethylene glycol to a subject in need thereof. The subject can be, for example, a mammal, a human, or a research animal that could be, for example, a rat, mouse, monkey, pig, cow, dog, or cat.

The disease or disorder is selected, for example, from the group consisting of reperfusion injury to the ischemic myocardium, general inflammation, inflammatory bowel disease, rheumatoid arthritis, osteoarthritis, hypertension, psoriasis, organ transplant rejections, organ preservation, radiation-induced injury, platelet aggregation, stroke, autoimmune diseases, refractory hypotension, adult respiratory distress, carcinogenesis, severe chronic pain, reversal of opioid tolerance, hyperalgesia, and sepsis.

The disorder can also be, for example, central pain or peripheral pain.

The PEGylated superoxide dismutase mimetic can be, for example:

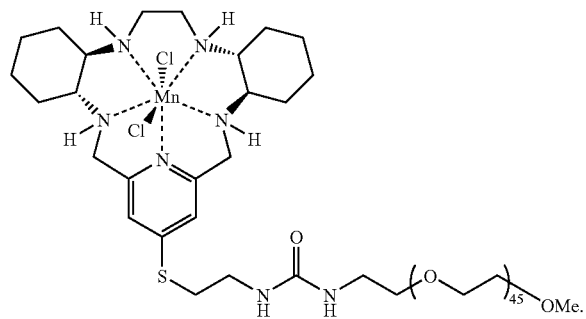

VIII

The PEGylated superoxide dismutase mimetic can also be, for example:

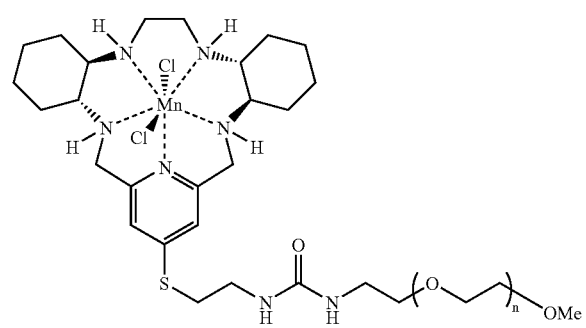

VII wherein the polyethylene glycol cars be of any length, specific lengths including but not limited to from about 7 to about 1,000, from about 10 to about 500, from about 15 to about 250, from about 20 to about 100, from about 25 to about 50, wherein n is about 23, wherein n is about 45, wherein n is about 114, or wherein n is about 455.

A compound as above, wherein the polyethylene glycol has a molecular weight from about 200 Da to about 44 kDa, from about 2500 Da to about 40 kDa, from about 1 kDa to about 35 kDa, from about 5 kDa to about 25 kDa, from about 800 Da to about 1200 Da, from about 1800 Da to about 2200 Da, from about 4800 Da to about 5200 Da, from about 9800 Da to about 10,200 Da, or from about 1900 Da to about 2100 Da.

The PEGylated superoxide dismutase mimetic used in the method can be selected from the group consisting of, for example, those from Table 4 above.

Methods of Making PEGylated Superoxide Dismutase Mimetics

A method for preparing a PEGylated superoxide dismutase mimetic, the method comprising reacting a compound comprising a polyethylene glycol with a compound comprising a superoxide dismutase mimetic. It should be noted that it is known to one of skill in the art that when reacting a monomer, in order to create a polymer, that the number of monomers can vary in the final product. For example, a compound with about 45 monomers can actually include about 10-20% variation in the number of monomers added to the compound. For example, molecules of a PEGylated superoxide dismutase mimetic in a mixture from a single reaction can vary significantly in the number of monomers of ethylene glycol that are have been linked to the superoxide dismutase mimetic.

The polyethylene glycol can be, for example, (a) a monomethoxy polyethylene glycol succinimidyl propionic acid (mPEG-SPA), (b) a monomethoxy polyethylene glycol isocyanate (mPEG-isocyanate), (c) a monomethoxy polyethylene glycol benzotriazole carbonate (mPEG-BTC), (d) a bifunctional polyethylene glycol benzothiazole carbonate (BTC-POLYETHYLENE GLYCOL-BTC), (e) a monomethoxy polyethylene glycol N,N'-cabonyldimidazole (mPEG-CDI) or (f) a monomethoxy polyethylene glycol N-hydroxysuccinimidyl ester (mPEG-NHS), (g) monomethoxy polyethylene glycol thiol (mPEG-SH), and (h) monomethoxy polyethylene glycol butyraldehyde (mPEG-butyrALD), (h) polyethylene glycol, and (i) monomethoxy polyethylene glycol.

A method of preparing a PEGylated superoxide dismutase mimetic, further comprising reacting the polyethylene glycol with the superoxide dismutase mimetic in an organic solvent. The organic solvent can be $CH_2Cl_2$ or, for example, a dipolar aprotic solvent, the dipolar aprotic solvent can be, for example, DMF and DMSO. The superoxide dismutase mimetic can be, for example, a pentaaza macrocycle. The pentaazamacrocycle can further be represented by, for example, a compound discussed herein or incorporated by reference.

A method of preparing a PEGylated superoxide dismutase mimetic wherein the reaction is an amine PEGylation reaction comprising a polyethylene glycol selected from the Table 6.

TABLE 6

Examples of PEG molecules that can be used in reactions with superoxide dismutase mimetics

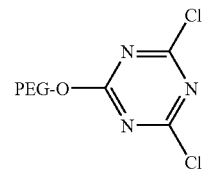

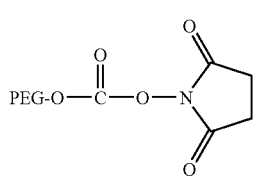

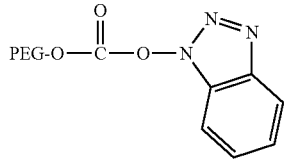

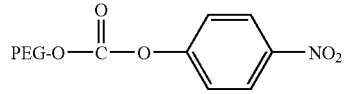

TABLE 6-continued

Examples of PEG molecules that can be used in reactions with superoxide dismutase mimetics

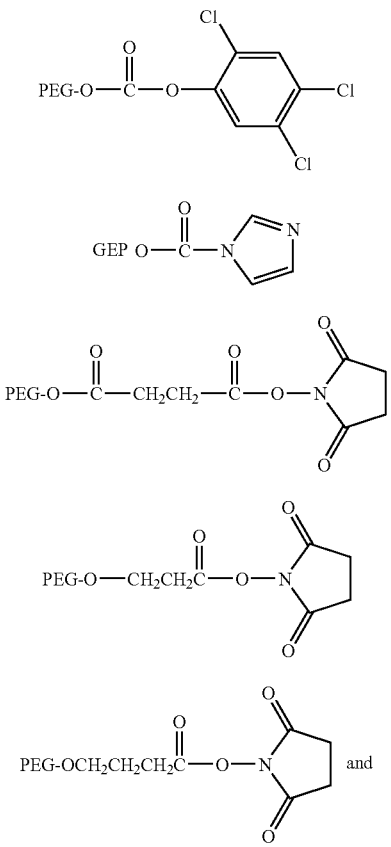

PEG-OCH₂CH₂N=C=O
CH₃-PEG-OCH₂CH₂OH
CH₃-PEG-OCH₂CH₂NH₂
CH₃-PEG-OCH₂CH₂CH₂CO₂H

The be superoxide dismutase mimetic can be, for example, represented by the formula:

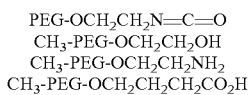

XLVIII

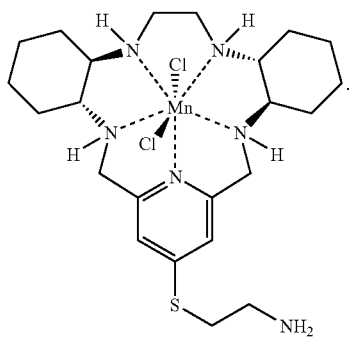

The covalent linkage of the superoxide dismutase mimetic and the polyethylene glycol polymer can be a direct covalent binding or attachment through a linker moeity. Methods of covalently linking an activated polyethylene glycol to various proteinaceous and non-proteinaceous materials are well known. For example, amine PEGylation reactions were among the first developed (for review, see Roberts et al, *Adv. Drug Delivery Rev.* 54:459-576, 2002).

Amine PEGylation reactions with a superoxide dismutase mimetic involve reaction of an amine derivative of a superoxide dismutase mimetic with an activated polyethylene glycol molecule, i.e. a polyethylene glycol derivative capable of reacting with the amine. Such activated polyethylene glycol molecules include (a) polyethylene glycol dichlorotriazine (PEG-DTC), (b) polyethylene glycol tresylate (PEG-TRES), (c) polyethylene glycol succinimidyl carbonate (PEG-SC), (d) polyethylene glycol benzotriazolyl carbonate (PEG-BTC), (e) polyethylene glycol p-nitrophenyl carbonate (PEG-NPC), (f) polyethylene glycol trichlorophenyl carbonate (PEG-TPC), (g) polyethylene glycol imidazolyl formate, (h) polyethylene glycol succinimidyl succinate (PEG-SS), (i) polyethylene glycol succinimidyl butanoic acid (PEG-SPA), (j) polyethylene glycol succinimidyl propionic acid (PEG-SPA) (k) polyethylene glycol isocyanate (PEG-isocyanate) and (l) polyethylene glycol propionaldehyde (for example see butyraldehyde). The activated polyethylene glycol molecules can be prepared by methods known in the art, typically involving reacting a polyethylene glycol with a group that is reactive with hydroxyl groups such as anhydrides, chlorides, chloroformates, or carbonates. Numerous activated polyethylene glycols are commercially available (for example from SunBlo USA, 57 Claremont Ave, Orinda, Calif. 94563). The use of monoalkyl derivatives and, in particular, monomethoxy derivatives of the above activated polyethylene glycol molecules (mPEG) allows the production of mono-functional conjugates.

Amine PEGylation reactions based upon activated monomethoxy polyethylene glycols can include the following reactions:

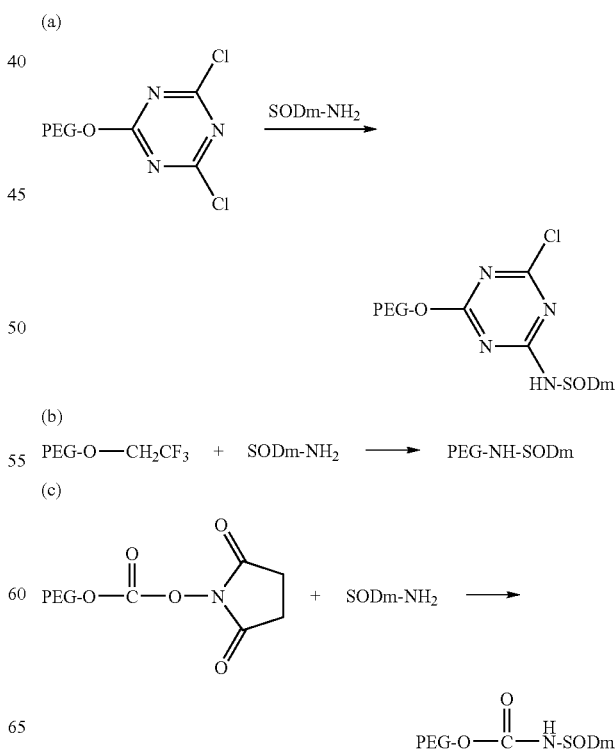

(d) 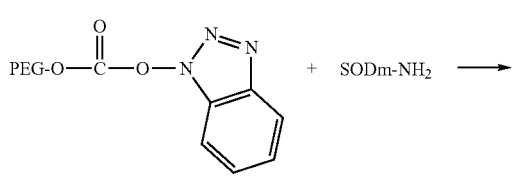

(e) 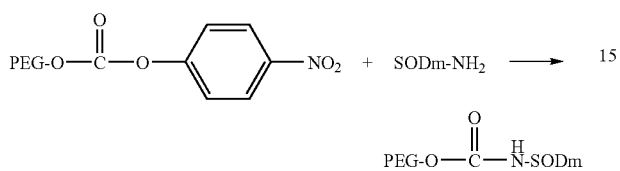

(f) 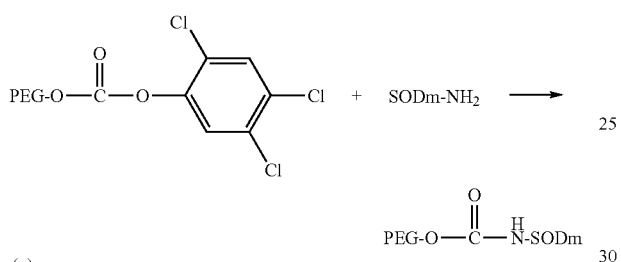

(g) 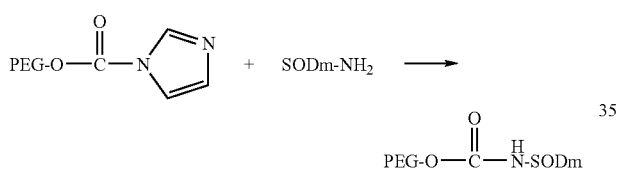

(h) 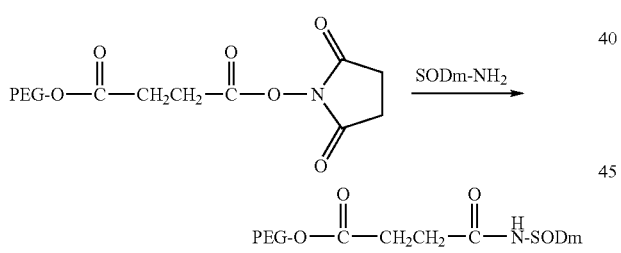

(i) 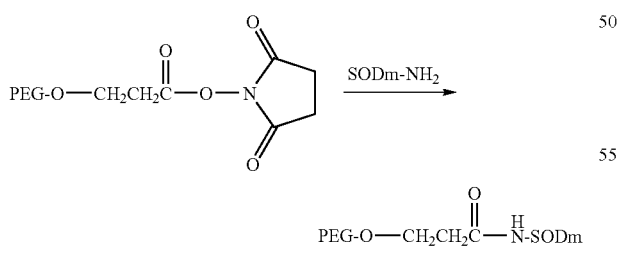

(j) 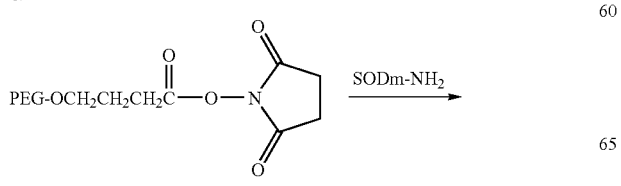

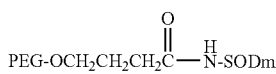

(k) 

(l)

The amine derivative of superoxide dismutase mimetic, superoxide dismutase mimetic-$NH_2$ can be, for example, the compound represented by formulas below:

IX

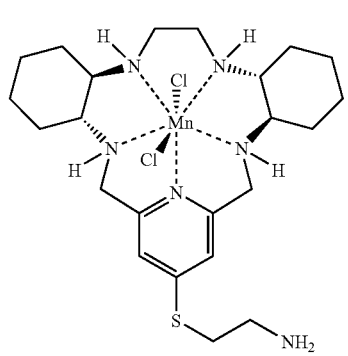

The PEGylation reaction can also be a reaction of an activated PEG with a halogen derivative of superoxide dismutase mimetic such as, for example, superoxide dismutase mimetic-Cl. The activated polyethylene glycol can be monomethoxy polyethylene glycol sulfhydryl (mPEG-sulfhydryl) (or polyethylene glycol hydroxyl) and the PEGylation reaction can be as follows:

$H_3C(OCH_2CH_2)_nSH$ + superoxide dismutase mimetic-Cl → superoxide dismutase mimetic-S—$(CH_2CH_2O)_nCH_3$ The chloro derivative of superoxide dismutase mimetic can be, for example, the compound represented by formula X below:

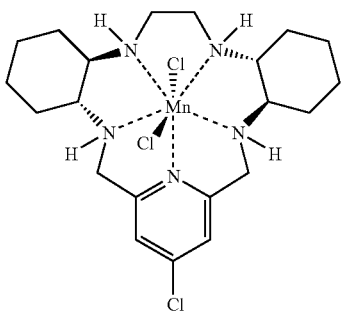

X

The carboxy derivative of superoxide dismutase mimetic can be, for example, the compound represented by the formulas below:

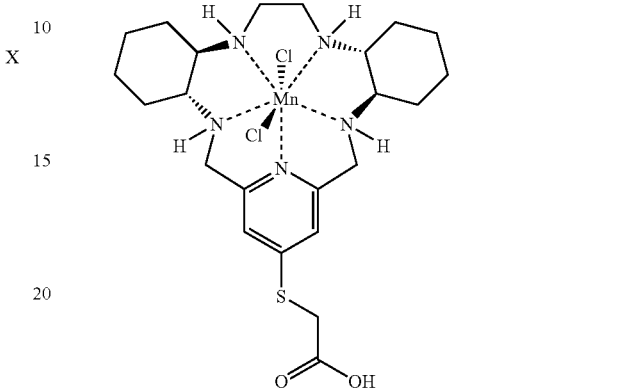

XXXII

An activated PEG compound can comprise many possible acids and bases of PEG. Some of these activated PEG molecules are described in U.S. Pat. Nos. 5,488,090, 5,672,662, 5,990,237 (which are herein incorporated by reference) and others. These are provided as examples and are not limiting.

Carboxyl PEGylation reactions can also be used to produce superoxide dismutase mimetic-polyethylene glycol conjugates. For example of a carboxyl PEGylation reaction involves the reaction of PEG-hydrazide in the presence of N,N'-dicyclohexylcarbodiimide or in the presence of a water soluble coupling agent such as N—(-3-dimethylaminopropyl)-N'-ethylcarbodiimide hydrochloride in the following reactions:

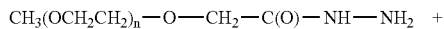

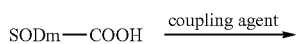

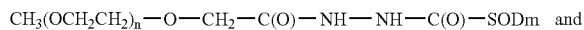

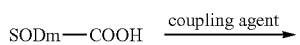

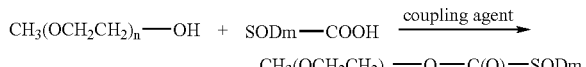

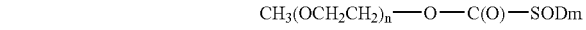

Hydroxyl PEGylation reactions can also be used to produce superoxide dismutase mimetic-polyethylene glycol conjugates. The activated polyethylene glycol molecules useful in hydroxyl PEGylation reactions include (a) polyethylene glycol epoxide (PEG-epoxide), (b) polyethylene glycol nitrophenyl carbonate (PEG-NPC) and (c) polyethylene glycol isocyanate (PEG-isocyanate). It is also possible to include esters in the reaction instead of hycroxylks, and create the corresponding ester PEG-superoxide dismutase mimetic compounds, illustrative examples of hydroxyl PEGylation reactions using monomethoxy PEG derivatives include the following:

(a)

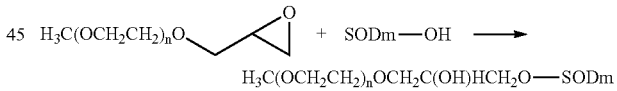

(b)

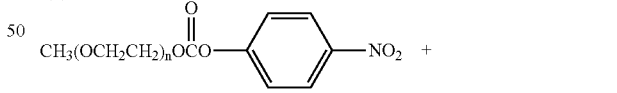

(c)

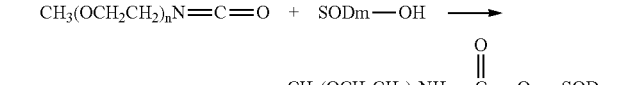

(d)

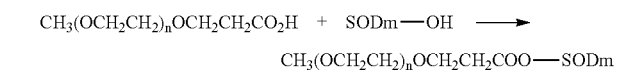

The hydroxy derivative of superoxide dismutase mimetic can be, for example, the compound represented by formula XII below:

XXXI

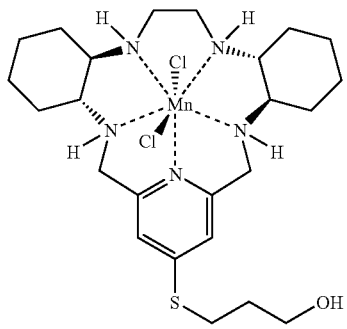

Thiol PEGylation reactions can also used to produce superoxide dismutase mimetic polyethylene glycol conjugates. The activated polyethylene glycol molecules useful in thiol PEGylation reactions include (a) polyethylene glycol maleimide (PEG-maleimide), (b) polyethylene glycol vinylsulfone (PEG-vinylsulfone), (c) polyethylene glycol orthopyridyl disulfide (PEG-OPSS) and (d) polyethylene glycol iodoacetamide (PEG-iodoacetamide). Illustrative examples of thiol PEGylation reactions using monomethoxy PEG derivatives include the following.

(a)
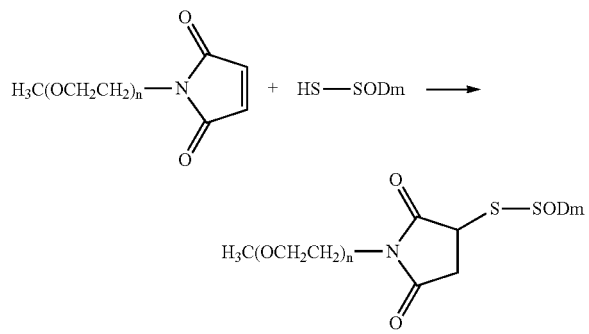

(b)
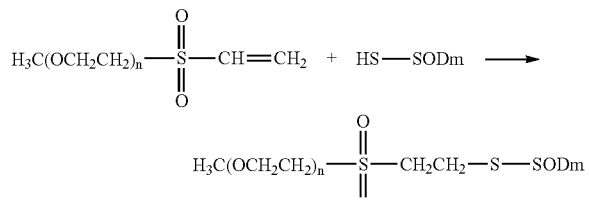

(c)
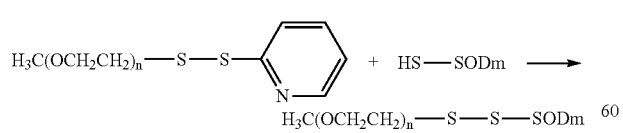

(d)
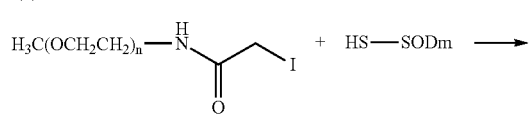

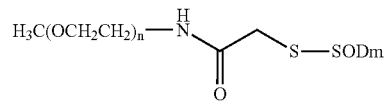

The thiol derivative of superoxide dismutase mimetic can be, for example, the compound represented fey formula XIII below:

LI

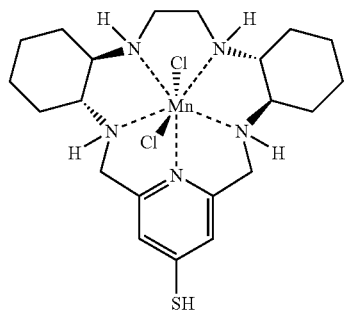

PEGylated compounds in which one PEG was attached to two superoxide dismutase mimetic molecules were prepared using a chloro derivative of a superoxide dismutase mimetic or an amine derivative of superoxide dismutase mimetic. Such reactions can be characterized as indicated below:

(a)

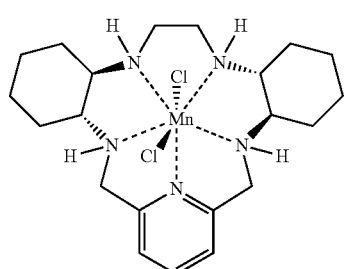

HS(CH$_2$CH$_2$O)$_n$CH$_2$CH$_2$SH
TMG, DMF, 80° C., overnight

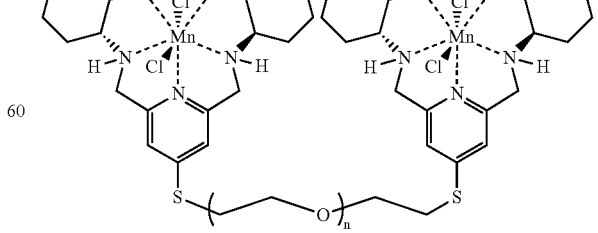

wherein n is between about 7 and about 1,000.

(b)
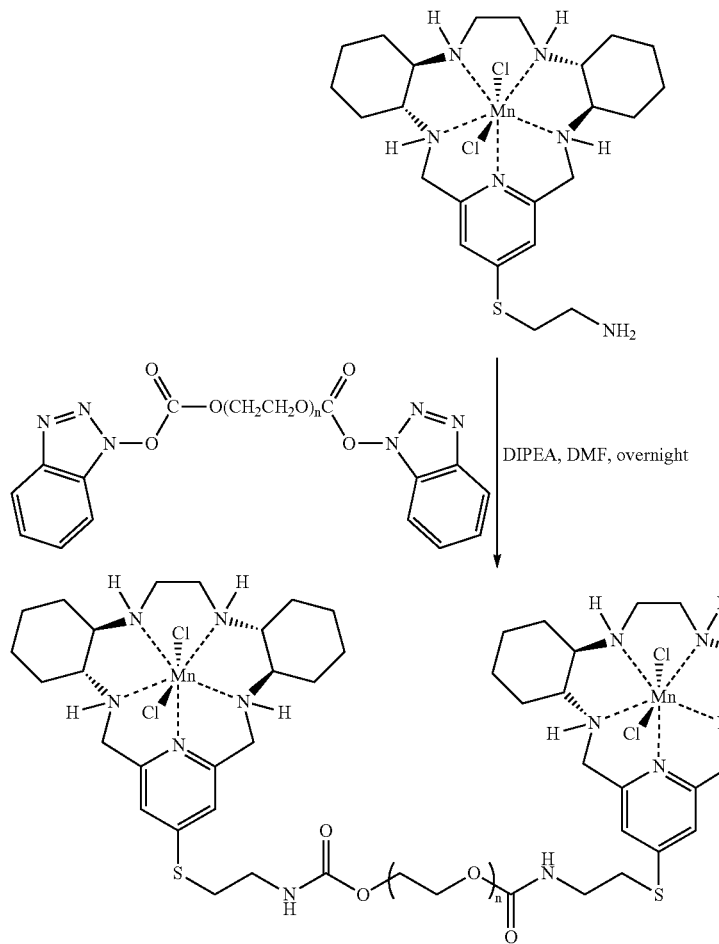
PEGylated compounds in which one PEG was attached to a superoxide dismutase mimetic molecules were prepared using starting compounds as characterized below:
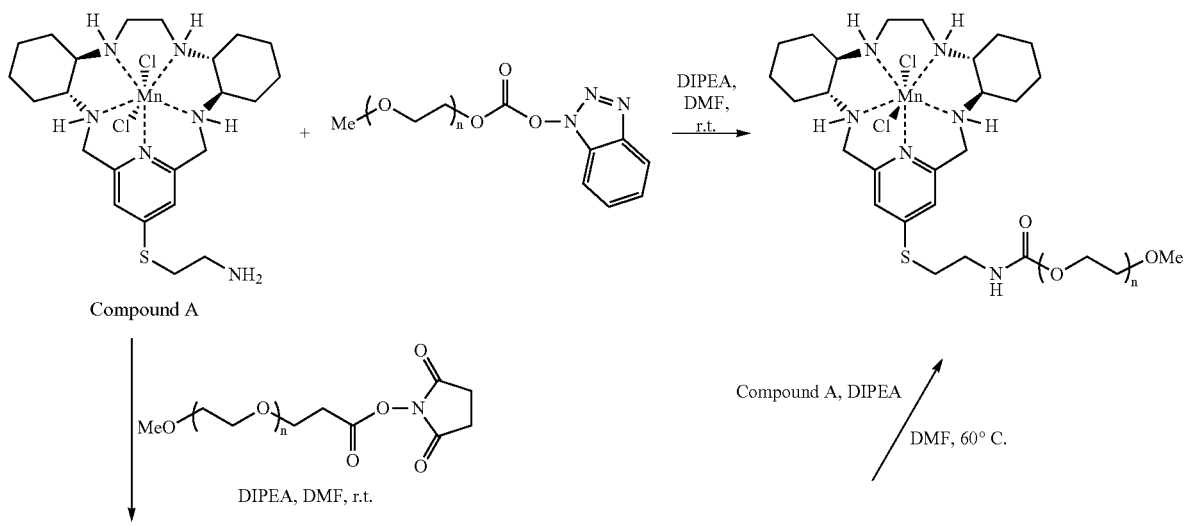

-continued
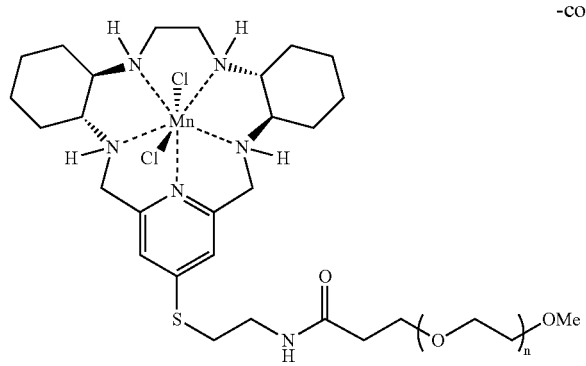
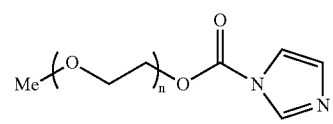
↑ DMF, 37° C.
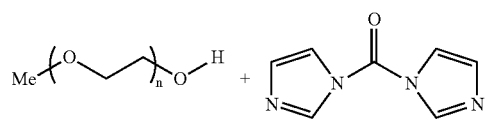
PEGylated compounds in which one PEG is attached to a superoxide dismutase mimetic molecules can also be prepared using any number of starting compounds. Such reactions can be characterized as indicated below:

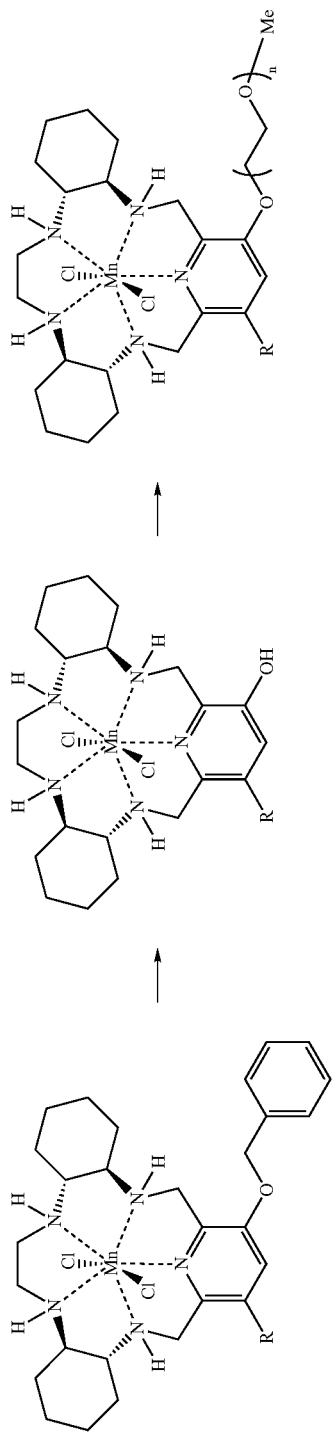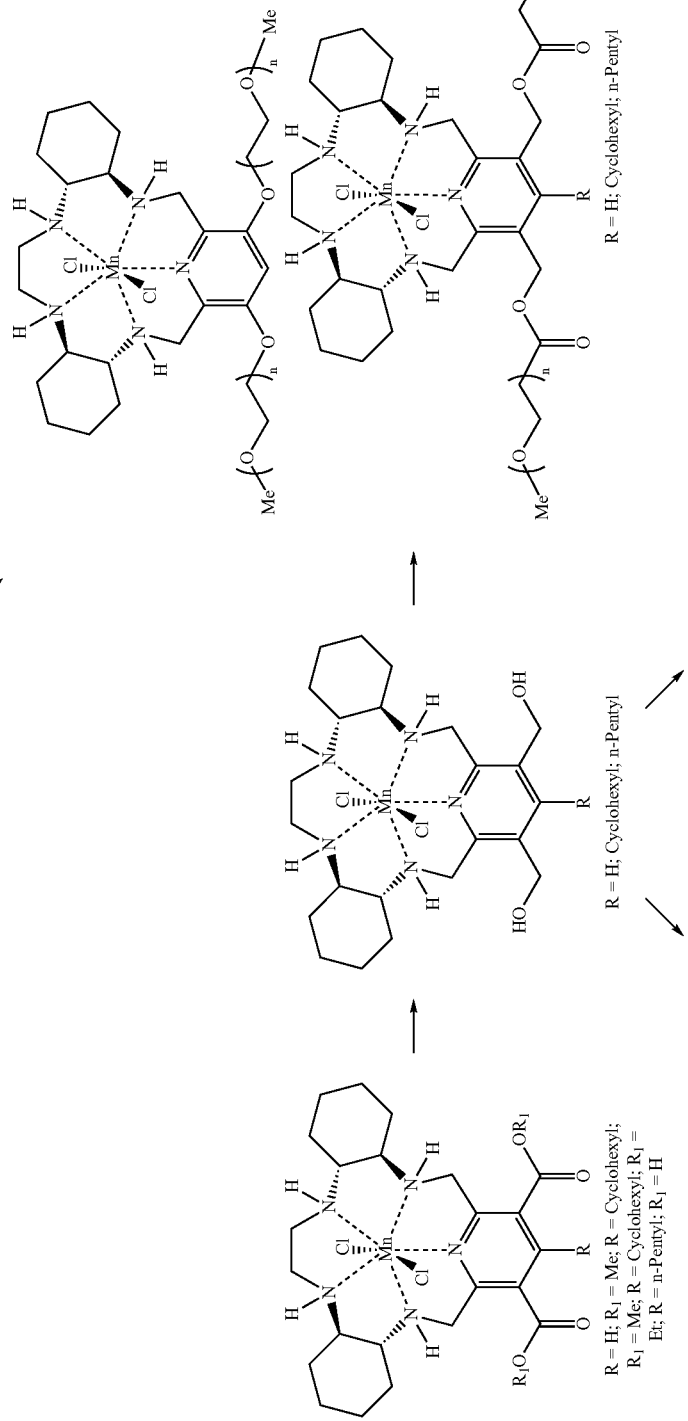

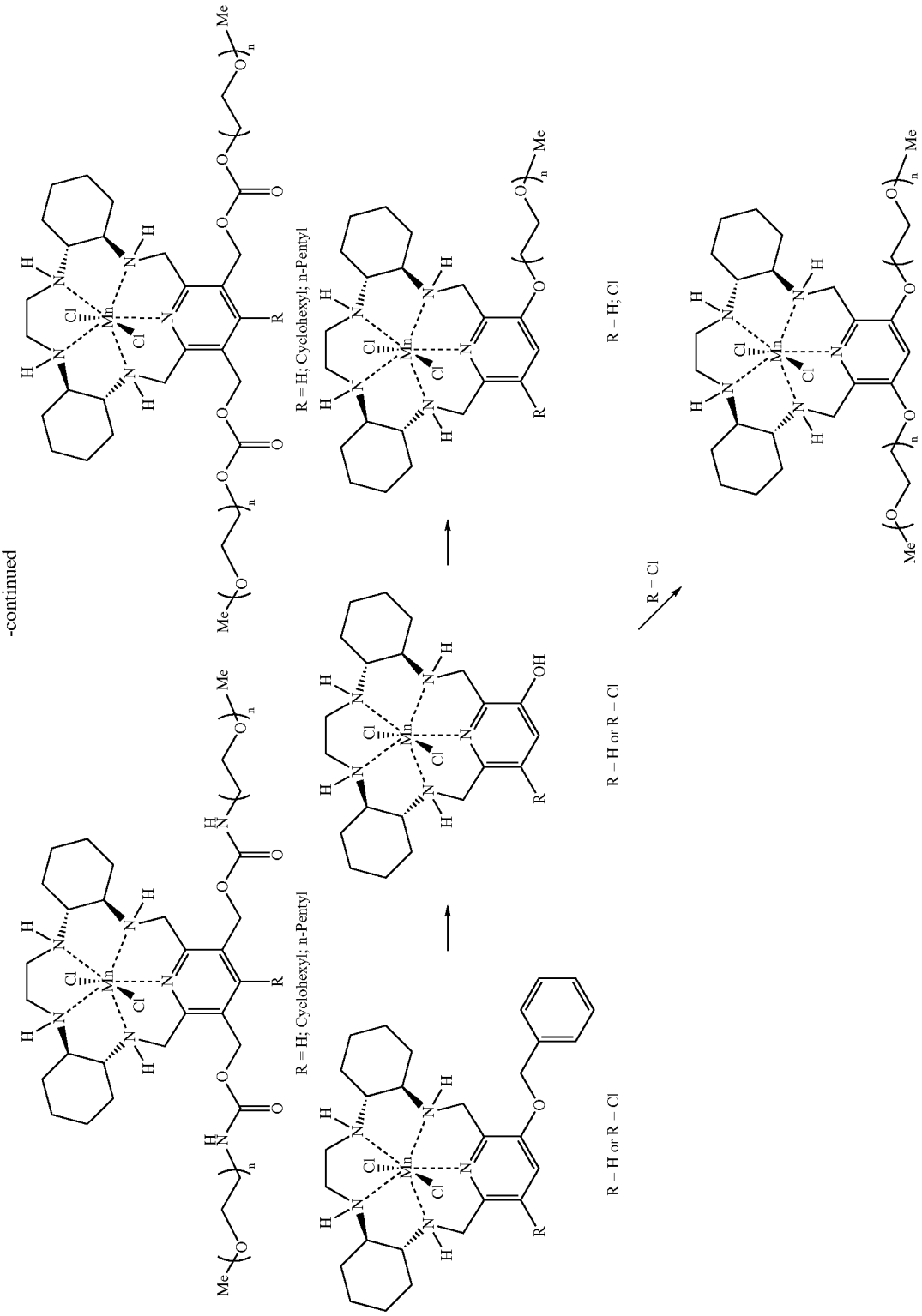

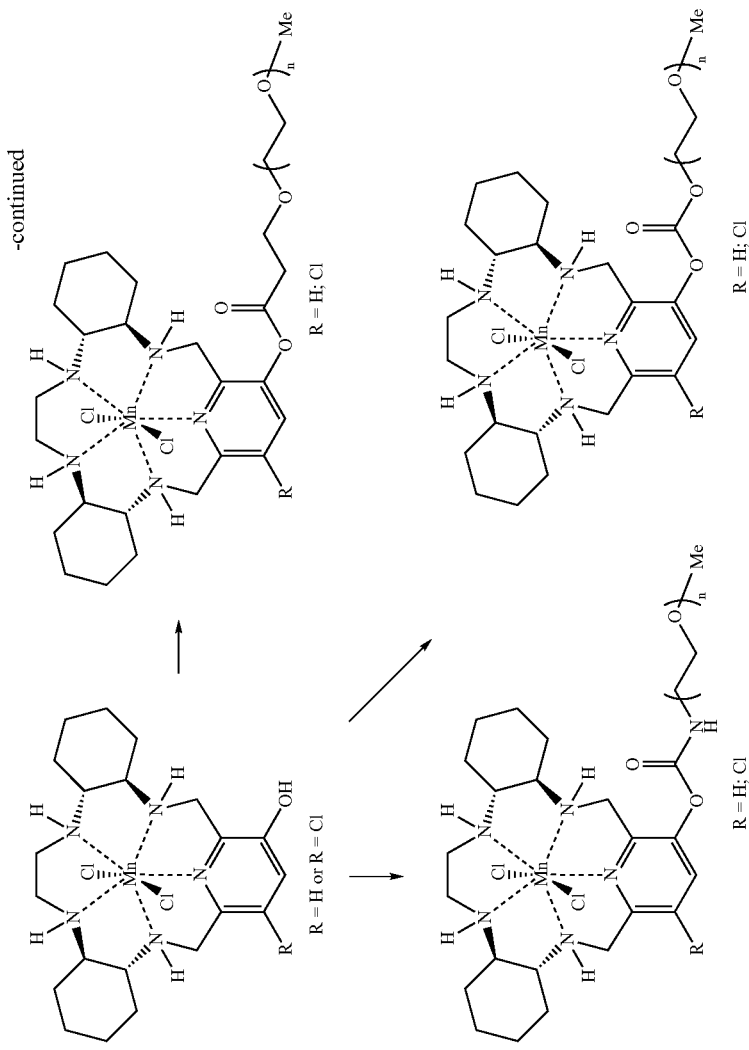

wherein n is between about 7 and about 1,000.

Other examples of PEGylated superoxide dismutase mimetic compounds include those with various linker molecules, such as:

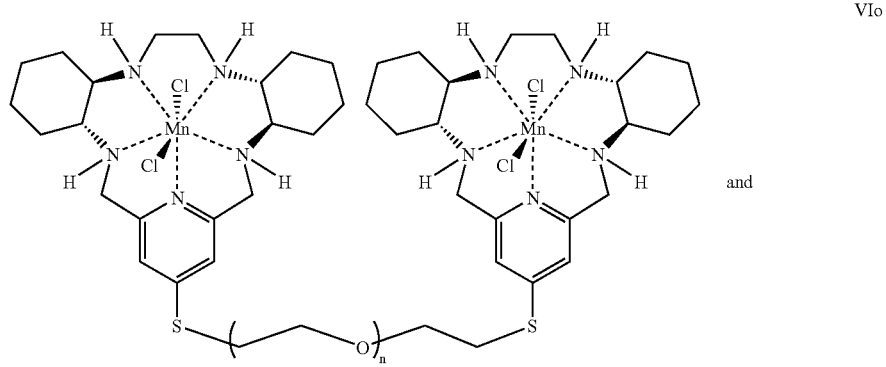

VIo and

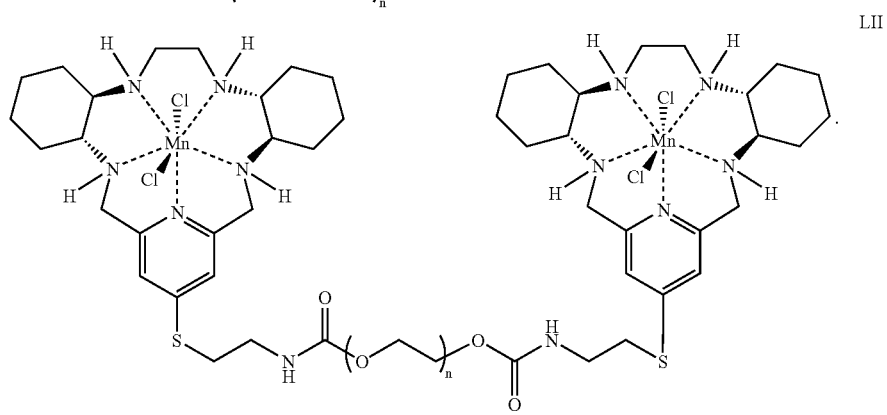

LII

Various superoxide dismutase mimetic PEGylated compounds also include superoxide dismutase mimetic compounds comprising a single superoxide dismutase mimetic molecule, such as (wherein n is between about 7 and about 1,000):

-continued

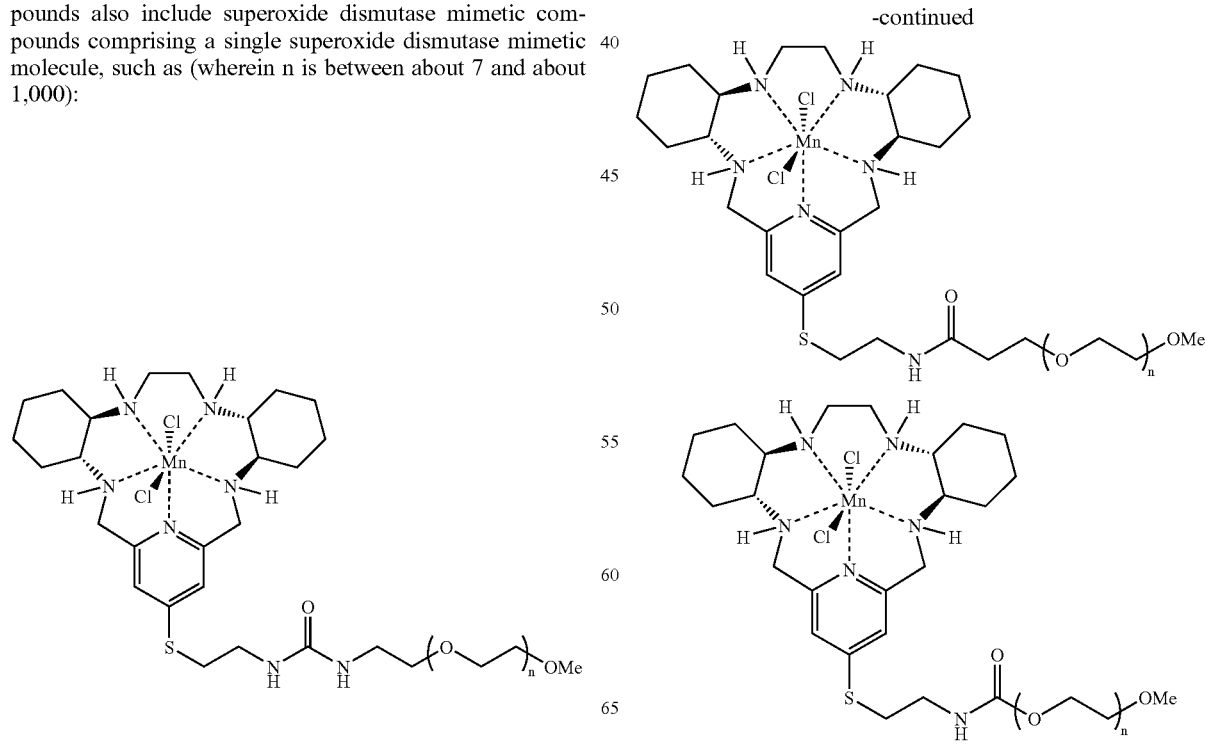

-continued

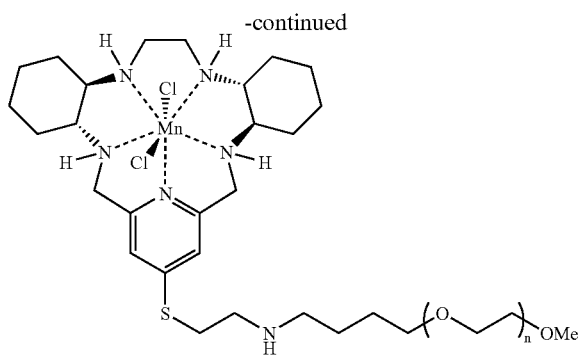

The superoxide dismutase mimetic-PEG conjugates of the present invention are active in catalyzing the dismutation of superoxide as measured by in vitro catalytic activity and by in vivo efficacy. In both the stopped-flow kinetic analysis and the cytochrome C assays as shown below in Example 7. The compounds also showed activity in carageenan-induced hyperalgesia in rats as shown below in Example 8. Moreover, the plasma concentrations following intravenous administration as well as the plasma half-life were both increased for the PEGylated superoxide dismutase mimetic compounds of the present invention as shown below in Example 9. In addition, these compounds have lower toxicity than their non-PEGylated counterparts, as can be seen, for example, in Example 11.

As a result of the superoxide dismutase activity of the PEGylated superoxide dismutase mimetic compounds of the present invention, the compounds are active in diseases or conditions involving superoxide ions. Such diseases and conditions for which the PEGylated superoxide dismutase mimetic molecules are effective include pain and inflammation, reversal of morphine tolerance and prevention of hypotension in endotoxemic animals.

The PEGylated superoxide dismutase mimetic compounds of the present invention can be utilized to treat numerous disease states and disorders in a patient in need thereof. The terms "patient" and "subject" includes human and non-human animals in need of treatment. Such disease states and disorders include, but are not limited to: reperfusion injury to an ischemic organ, such as reperfusion injury to the ischemic myocardium, general inflammation, inflammatory bowel disease, rheumatoid arthritis, osteoarthritis, hypertension, psoriasis, organ transplant rejections, refractory hypotension, organ preservation, radiation-induced injury, platelet aggregation, stroke, autoimmune diseases, adult respiratory distress, carcinogenesis, severe chronic pain, hyperalgesia, and sepsis. The PEGylated compounds of this invention are analgesics. As such, they can be used to treat or prevent pain in a subject arising from any hyperalgesic state. The compounds further have activity to prevent or reduce tolerance to opiates, and to potentiate the analgesic activity of opiates without potentiating the respiratory depression associated with opiates. In addition, the compounds are useful in treating withdrawal symptoms associated with addiction to opiates, nicotine, or other drugs. The compounds of this invention can also be used systemically or topically to prevent or reverse free oxygen radical-mediated symptoms of aging, such as skin wrinkling, and to prevent or reverse environmental damage caused by exposure to ultraviolet radiation or chemical agents.

Total daily dose administered to a subject in single or divided doses may be in amounts, for example, from about 0.00025 to about 20 mg/kg body weight daily, from about 0.001 to about 10 mg/kg body weight daily or from about 0.01 to about 3 mg/kg body weight daily, when given as a parenteral injection or continuous infusion. Dosage unit compositions may contain such amounts of sub-multiples thereof to make up the daily dose. The amount of active ingredient that may be combined with the carrier materials to produce a single dosage form will vary depending upon the subject treated and the particular mode of administration. For instance, systems such as transdermal administration or oral administration, which are substantially less efficient delivery systems, may require dosages at least an order of magnitude above those required for parenteral administration. The dosage regimen for treating a disease condition with the compounds and/or compositions of this invention is selected in accordance with a variety of factors, including the type, age, weight, sex, diet and medical condition of the patient, the severity of the disease, the route of administration, pharmacological considerations such as the activity, efficacy, pharmokinetic and toxicology profiles of the particular compound employed, whether a drug delivery system is utilized and whether the compound is administered as part of a drug combination. Thus, the dosage regimen actually employed may vary widely and therefore may deviate from the preferred dosage regimen set forth above. Those of ordinary skill in the art can readily determine appropriate dosages for any particular subject based on the teachings in this specification and routine analysis of the subject.

The compounds of the present invention may be administered by any technique known to those of ordinary skill, including but not limited to, orally, parenterally, by inhalation spray, racially, topically or by nasal, vaginal or ocular administration, in dosage unit formulations containing conventional nontoxic pharmaceutically acceptable carriers, adjuvants, and vehicles as desired. Topical administration may also involve the use of transdermal administration such as transdermal patches or iontophoresis devices. The term parenteral as used herein includes subcutaneous injections, intravenous, intramuscular, intrasternal injection, intrathecal or infusion techniques. Injectable preparations, for example, sterile injectable aqueous or oleaginous suspensions may be formulated according to the known art using suitable dispersing or wetting agents and suspending agents. The sterile injectable preparation may also be a sterile injectable solution or suspension in a nontoxic parenterally acceptable diluent or solvent, for example, as a solution in 1,3-butanediol. Among the acceptable vehicles and solvents that may be employed are water, Ringer's solution, and isotonic sodium chloride solution, in addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

Suppositories for rectal administration of the drug can be prepared by mixing the drug with a suitable nonirritating excipient such as cocoa butter and polyethylene glycols which are solid at ordinary temperatures but liquid at the rectal temperature and will therefore melt in the rectum and release the drug. Solid dosage forms for oral administration may include capsules, tablets, pills, powders, granules and gels. In such solid dosage forms, the active compound may be admixed with at least one inert diluent such as sucrose, lactose, or starch. Such dosage forms may also comprise, as in normal practice, additional substances other than inert diluents, e.g., lubricating agents such as magnesium stearate. In the case of capsules, tablets, and pills, the dosage forms may also comprise buffering agents. Tablets and pills can additionally be prepared with enteric coatings. Liquid dosage forms for oral administration may include pharmaceutically acceptable emulsions, solutions, suspensions, syrups, and elixirs containing inert diluents commonly used in the art, such as water. Such compositions may also comprise adjuvants, such as wetting agents, emulsifying and suspending agents, and sweetening, flavoring, and perfuming agents.

While the compounds of the invention can be administered as the sole active pharmaceutical agent, they can also be used in combination with one or more compounds which are known to be effective against the specific disease state that one is targeting for treatment.

As a result of the compounds of the present invention being active in catalyzing the dissimulation of superoxide, they can be used in this catalytic capacity in a variety of in vivo and in vitro applications where a reduction in superoxide concentration is desired and, in particular, in in vivo applications in which a prolonged action is desired. Such prolonged action is possible with the PEGylated superoxide dismutase mimetic compounds of the present invention as a result of the extended half life produced by the PEGylation of the compounds.

The capacity of the compounds of the present invention to catalyze the decomposition of reactive oxygen species along with the extended half-life of the compounds can be used to advantage to inhibit or slow damage to biological tissues and cells. For example, oxyradical-induced damage to connective tissues (e.g., collagen) attendant to exposure to UV light, cigarette smoking, and senescence may be reduced by administration of a PEGylated SOD mimetic compound of the present invention approximately concomitant with the exposure to UV light, cigarette smoking, or other oxyradical-generating process (e.g., cellular senescence). As a result of the extended half-life, an extended period of protection can be achieved.

The PEGylated SOD mimetics of the present invention can be formulated into a pharmaceutically- or cosmetically-acceptable organic solvent. The terms "pharmaceutically-acceptable organic solvent" and "cosmetically-acceptable organic solvent" refer to an organic solvent which, in addition to being capable of having dispersed or dissolved therein the salen-metal compound, and optionally also an anti-inflammatory agent, also possesses acceptable safety (e.g. irritation and sensitization characteristics), as well as good aesthetic properties (e.g., does not feel greasy or tacky). The most typical example of such a solvent is isopropanol. Examples of other suitable organic solvents include: propylene glycol, polyethylene glycol (200-800), polypropylene glycol (425-2025), glycerol, 1,2,4-butanetriol, sorbitol esters, 1,2,6-hexanetriol, ethanol, butanediol, water and mixtures thereof. These solutions contain from about 0.001% to about 20%, preferably from about 0.1% to about 10%, superoxide dismutase mimetic complex, from about 0.01% to about 5%, preferably from about 0.5% to about 2% of an anti-inflammatory agent, and from about 80% to about 99%, preferably from about 90% to about 98%, of an acceptable organic solvent.

As used herein, "emollients" refer to materials used for the prevention or relief of dryness, as well as for the protection of the skin. A wide variety of suitable emollients are known and may be used herein. Sagarin, Cosmetics, Science and Technology, 2nd Edition, Vol. 1, pp. 32-43 (1972), incorporated herein by reference, contains numerous examples of suitable materials. Particularly useful emollients which provide skin conditioning are glycerol, hexanetriol, butanetriol, lactic acid and its salts, urea, pyrrolidone carboxylic acid and its salts, amino acids, guanidine, diglycerol and triglyceryl. Preferred skin conditioning agents are the propoxylated glycerol derivatives.

The invention also provides methods for preventing food spoilage and oxidation by applying to foodstuffs an effective amount of at least one PEGylated SOD mimetic compound of the present invention, optionally in combination with at least one additional food preservative agent (e.g., butylated hydroxytoluene, butylated hydroxyanisole, sulfates, sodium nitrite, sodium nitrate). In another aspect, the invention relates to antioxidant compositions and methods of use in inhibiting formation of undesired hydrocarbon polymers generated via free radical-mediated polymerization mechanisms, especially oxyradical-mediated polymerization and/or oxyradical-mediated rancidification or gum formation. The PEGylated SOD mimetic compounds of the invention can be applied to a variety of hydrocarbons to reduce undesired oxidation and/or polymerization, or to quench a polymerization reaction at a desired state of polymer formation (e.g., at a desired average chain length). For example and not to limit the invention, examples of such saturated and unsaturated hydrocarbons include: petroleum distillates and petrochemicals, turpentine, paint synthetic and natural rubber, vegetable oils and waxes, animal fats, polymerizable resins, polyolefin, and the like.

The compounds of the present invention may also be used to protect cells and tissues from free radical-producing agents, such as ionizing radiation and chemotherapeutic agents (e.g., bleomycin). Preferably, a protective dosage comprising at least about 0.001 mg of PEGylated SOD mimetic/kg body weight is administered by one or more of several routes (e.g., oral, intravenous, intraperitoneal, intragastric lavage, enema, portal vein infusion, topical, or inhalation of mist) to protect normal cells, for example, against free radical toxicity associated with chemotherapy or radiotherapy of a neoplasm. The compounds of the present invention are preferably pre-administered to the patient prior to the commencement of the chemotherapy and/or radiotherapy, usually within about 24 hours of commencement, and preferably within about 3-6 hours of commencement of the chemotherapy and/or radiotherapy. The compounds may be continually administered to the patient during the course of therapy.

The PEGylated SOD mimetics of the present invention also can be administered to individuals to prevent radiation injury or chemical injury by free radical generating agents. Military personnel and persons working in the nuclear, nuclear medicine, and/or chemical industries may be administered the compounds of the present invention prophylactically. These may also be used as chemoprotective agents to prevent chemical carcinogenesis; particularly by carcinogens which form reactive epoxide intermediates (e.g., benzopyrene, benzanthracene) and by carcinogens or promoting agents which form free radicals directly or indirectly (e.g., Phenobarbital, TPA i.e. 12-O-tetradecanoyl phorbol-13-acetate, benzoyl peroxiprolieroxisome proliferators: ciprofibrate, clofibrate). Persons exposed to such chemical carcinogens are pretreated with the compounds of the present invention to reduce the incidence or risk of developing neoplasia.

Other Aspects of the Instant Invention

Toxicity and therapeutic efficacy of such compounds can be determined by standard pharmaceutical procedures in cell cultures or experimental animals for determining the $LD_{50}$ (the dose lethal to 50% of the population) and the $ED_{50}$, (the dose therapeutically effective in 50% of the population). The dose ratio between toxic and therapeutic effects is the therapeutic index that can be expressed as the ratio $LD_{50}/ED_{50}$. Compounds that exhibit large therapeutic indices are preferred. As can be seen below in the examples, both animal models and humans can be used for these studies. This can be used to determine safety of a single compound, or compare the safety of two different compounds.

A method comparing two compounds can comprise a method as follows:

(a) covalently attaching at least one polyethylene glycol to a superoxide dismutase mimetic;

(b) administering the superoxide dismutase mimetic comprising the polyethylene to a living cell;

(c) determining the $LD_{50}$ of a superoxide dismutase mimetic comprising the polyethylene glycol;

(d) administering an identical superoxide dismutase mimetic not comprising the polyethylene to a living cell;

(e) determining the $LD_{50}$ of an Identical superoxide dismutase mimetic not comprising the polyethylene glycol; and (f) comparing the $LD_{50}$ of the superoxide dismutase mimetic comprising the polyethylene glycol with an identical superoxide dismutase mimetic not comprising the polyethylene glycol.

This method can be method can be used in a mammal, for example. The mammal can be any mammal, but for example, can be a rat, mouse, cat, dog, or monkey.

The PEGylated superoxide dismutase mimetic can be any superoxide dismutase mimetic to which is covalently attached at least one polyethylene glycol molecule which includes:

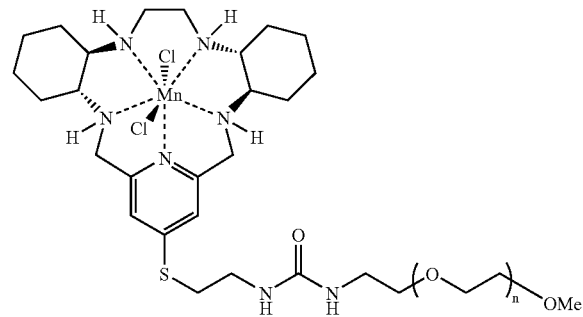

VII wherein n is an integer, for example, from about 7 to about 1,000, from about 10 to about 500, from about 15 to about 250, from about 20 to about 100, from about 25 to about 50, wherein n is about 23, wherein n is about 45, wherein n is about 114, or wherein n is about 455. A compound as above, wherein the polyethylene glycol has a molecular weight from about 200 Da to about 44 kDa, from about 2500 Da to about 40 kDa, from about 1 kDa to about 35 kDa, from about 5 kDa to about 25 kDa, from about 800 Da to about 1200 Da, from about 1800 Da to about 2200 Da, from about 4800 Da to about 5200 Da, from about 9800 Da to about 10,200 Da, or from about 1900 Da to about 2100 Da. The invention is not limited to these compounds and any PEGylated superoxide dismutase mimetic can be used in the instant invention.

PEGylated superoxide dismutase mimetics can be, for example, those from Table 4 above.

The instant invention further includes a method for determining a dose lethal to 50% of a population, the method comprising:

(a) administering a superoxide dismutase mimetic to at least a cell, tissue, or organism; and (b) monitoring the cell, tissue, or organism during and after the course of said administration to assess the viability of the cell, tissue, or organism.

Pharmaceutical Preparations and Methods of Administration

The Identified compounds treat, inhibit, control and/or prevent, or at least partially arrest or partially prevent, diseases and conditions wherein superoxide radicals are produced and can be administered to a subject at therapeutically effective doses for the inhibition, prevention, prophylaxis or therapy for such diseases. The compounds of the present invention comprise a therapeutically effective dosage of at least a superoxide dismutase mimetic, a terms which includes therapeutically, inhibitory, preventive and prophylactically effective doses of the compounds of the present invention and is more particularly defined below. The subject is preferably an animal, including, but not limited to, mammals, reptiles and avians, more preferably horses, cows, dogs, cats, sheep, pigs, and chickens, and most preferably human.

Therapeutically Effective Dosage

Toxicity and therapeutic efficacy of such compounds can be determined by standard pharmaceutical procedures in cell cultures or experimental animals for determining the $LD_{50}$ (the dose lethal to 50% of the population) and the $ED_{50}$, (the dose therapeutically effective in 50% of the population). The dose ratio between toxic and therapeutic effects is the therapeutic index that can be expressed as the ratio $LD_{50}/ED_{50}$. Compounds that exhibit large therapeutic indices are preferred. While compounds exhibiting toxic side effects may be used, care should be taken to design a delivery system that targets such compounds to the site affected by the disease or disorder in order to minimize potential damage to unaffected cells and reduce side effects.

The data obtained from the cell culture assays and animal studies can be used in formulating a range of dosages for use in humans and other mammals. The dosage of such compounds lies preferably within a range of circulating plasma or other bodily fluid concentrations that include the $ED_{50}$ and provides clinically efficacious results (i.e. reduction in disease symptoms). The dosage may vary within this range depending upon the dosage form employed and the route of administration utilized. For any compound of the invention, the therapeutically effective dose can be estimated initially from cell culture assays. A dosage may be formulated in animal models to achieve a circulating plasma concentration range that includes the $IC_{50}$ (the concentration of the test compound that achieves a half-maximal inhibition of symptoms) as determined in cell culture. Such information can be used to more accurately determine useful dosages in humans and other mammals. Compound levels in plasma may be measured, for example, by high performance liquid chromatography.

The amount of a compound that may be combined with a pharmaceutically acceptable carrier to produce a single dosage form will vary depending upon the host treated and the particular mode of administration. It will be appreciated by those skilled in the art that the unit content of a compound contained in an individual dose of each dosage form need not in itself constitute a therapeutically effective amount, as the necessary therapeutically effective amount could be reached by administration of a number of individual doses. The selection of dosage depends upon the dosage form utilized, the condition being treated, and the particular purpose to be achieved according to the determination of those skilled in the art.

The dosage and dosage regime for treating a disease or condition with the compounds of the invention is selected in accordance with a variety of factors, including the type, age, weight, sex, diet and medical condition of the patient, the route of administration, pharmacological considerations such as activity, efficacy, pharmacokinetic and toxicology profiles of the particular compound employed, whether a compound delivery system is utilized and whether the compound is administered as a pro-drug or part of a drug combination. Thus, the dosage regime actually employed may vary widely from subject to subject, or disease to disease and different routes of administration may be employed in different clinical settings.

Formulations and Use

The compounds of the present invention may be formulated by known methods for administration to a subject using several routes which include, but are not limited to, parenteral, oral, topical, intradermal, intramuscular, intraperitoneal, intravenous, subcutaneous, intranasal, epidural, and ophthalmic routes. The individual compounds may also be administered in combination with one or more additional compounds of the present invention and/or together with other biologically active or biologically inert agents. Such biologically active or inert agents may be in fluid or mechanical communication with the compound(s) or attached to the compound(s) by ionic, covalent, Van der Waals, hydrophobic, hydrophilic or other physical forces, it is preferred that administration is localized in a subject, but administration may also be systemic.

The compounds of the present invention may be formulated by any conventional manner using one or more pharmaceutically acceptable carriers and/or excipients. Thus, the compounds and their pharmaceutically acceptable salts and solvates may be specifically formulated for administration, e.g., by inhalation or insufflation (either through the mouth or the nose) or oral, buccal, parenteral or rectal administration. The compounds may take the form of charged, neutral and/or other pharmaceutically acceptable salt forms. Examples of pharmaceutically acceptable carriers include, but are not limited to, those described in REMINGTON'S PHARMACEUTICAL SCIENCES (A. R. Gennaro, Ed.), 20th edition, Williams & Wilkins Pa., USA (2000).

The compounds may also take the form of solutions, suspensions, emulsions, tablets, pills, capsules, powders, controlled- or sustained-release formulations and the like. Such formulations will contain a therapeutically effective amount of the compound, preferably in purified form, together with a suitable amount of carrier so as to provide the form for proper administration to the patient. The formulation should suit the mode of administration.

Parenteral Administration

The compound may be formulated for parenteral administration by injection, e.g., by bolus injection or continuous infusion. Formulations for injection may be presented in unit dosage form in ampoules or in multi-dose containers with an optional preservative added. The parenteral preparation can be enclosed in ampoules, disposable syringes or multiple dose vials made of glass, plastic or the like. The formulation may take such forms as suspensions, solutions or emulsions in oily or aqueous vehicles, and may contain formulatory agents such as suspending, stabilizing and/or dispersing agents.

For example, a parenteral preparation may be a sterile injectable solution or suspension in a nontoxic parenterally acceptable diluent or solvent (e.g., as a solution in 1,3-butanediol). Among the acceptable vehicles and solvents that may be employed are water, Ringer's solution, and isotonic sodium chloride solution, in addition, sterile, fixed oils are conventionally employed as a solvent or suspending medium. For this purpose any bland fixed oil may be employed including synthetic mono- or diglycerides, in addition, fatty acids such as oleic acid may be used in the parenteral preparation.

Alternatively, the compound may be formulated in powder form for constitution with a suitable vehicle, such as sterile pyrogen-free water, before use. For example, a compound suitable for parenteral administration may comprise a sterile isotonic saline solution containing between 0.1 percent and 90 percent weight per volume of the compound. By way of example, a solution may contain from about 5 percent to about 20 percent, more preferably from about 5 percent to about 17 percent, more preferably from about 8 to about 14 percent, and still more preferably about 10 percent of the compound. The solution or powder preparation may also include a solubilizing agent and a local anesthetic such as lignocaine to ease pain at the site of the injection. Other methods of parenteral delivery of compounds will be known to the skilled artisan and are within the scope of the invention.

Oral Administration

For oral administration, the compound may take the form of tablets or capsules prepared by conventional means with pharmaceutically acceptable excipients such as binding agents, fillers, lubricants and disintegrants:

A. Binding Agents

Binding agents include, but are not limited to, corn starch, potato starch, or other starches, gelatin, natural and synthetic gums such as acacia, sodium alginate, alginic acid, other alginates, powdered tragacanth, guar gum, cellulose and its derivatives (e.g., ethyl cellulose, cellulose acetate, carboxymethyl cellulose calcium, sodium carboxymethyl cellulose), polyvinyl pyrrolidone, methyl cellulose, pre-gelatinized starch, hydroxypropyl methyl cellulose, (e.g., Nos. 2208, 2908, 2910), microcrystalline cellulose, and mixtures thereof. Suitable forms of microcrystalline cellulose include, for example, the materials sold as AVICEL-PH-101, AVICEL-PH-103 and AVICEL-PH-103 (available from FMC Corporation, American Viscose Division, Avicel Sales, Marcus Hook, Pa., USA). An exemplary suitable binder is a mixture of microcrystalline cellulose and sodium carboxymethyl cellulose sold as AVICEL RC-581 by FMC Corporation.

B. Fillers

Fillers include, but are not limited to, talc, calcium carbonate (e.g., granules or powder), lactose, microcrystalline cellulose, powdered cellulose, dextrates, kaolin, mannitol, silicic acid, sorbitol, starch, pre-gelatinized starch, and mixtures thereof.

C. Lubricants

Lubricants include, but are not limited to, calcium stearate, magnesium stearate, mineral oil, light mineral oil, glycerin, sorbitol, mannitol, polyethylene glycol, other glycols, stearic acid, sodium lauryl sulfate, talc, hydrogenated vegetable oil (e.g., peanut oil, cottonseed oil, sunflower oil, sesame oil, olive oil, corn oil, and soybean oil), zinc stearate, ethyl oleate, ethyl laurate, agar, and mixtures thereof. Additional lubricants include, for example, a syloid silica gel (AEROSIL 200, manufactured by W. R. Grace Co. of Baltimore, Md., USA), a coagulated aerosol of synthetic silica (marketed by Deaussa Co. of Plano, Tex., USA), CAB-O-SIL (a pyrogenic silicon dioxide product sold by Cabot Co. of Boston, Mass., USA), and mixtures thereof.

D. Disintegrants

Disintegrants include, but are not limited to, agar-agar, alginic acid, calcium carbonate, microcrystalline cellulose, croscarmellose sodium, crospovidone, polacrilin potassium, sodium starch glycolate, potato or tapioca starch, other starches, pre-gelatinized starch, other starches, clays, other algins, other celluloses, gums, and mixtures thereof.

The tablets or capsules may optionally be coated by methods well known in the art. If binders and/or tillers are used with the compounds of the invention, they are typically formulated as about 50 to about 99 weight percent of the compound. In one aspect, about 0.5 to about 15 weight percent of disintegrant, and particularly about 1 to about 5 weight percent of disintegrant, may be used in combination with the compound. A lubricant may optionally be added, typically in an amount of less than about 1 weight percent of the compound. Techniques and pharmaceutically acceptable additives for making solid oral dosage forms are described in Marshall. SOLID ORAL DOSAGE FORMS, Modern Pharmaceutics (Banker and Rhodes, Eds.), 7:359-427 (1979). Other less typical formulations are known in the art.

Liquid preparations for oral administration may take the form of solutions, syrups or suspensions. Alternatively, the liquid preparations may be presented as a dry product for constitution with water or other suitable vehicle before use. Such liquid preparations may be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., almond oil, oily esters, ethyl alcohol or fractionated vegetable oils); and/or preservatives (e.g., methyl or propyl-p-hydroxybenzoates or sorbic acid). The preparations may also contain buffer salts, flavoring, coloring, perfuming and sweetening agents as appropriate. Preparations for oral administration may also be formulated to achieve controlled release of the compound. Oral formulations preferably contain 10% to 95% compound. In addition, the compounds of the present invention may be formulated for buccal administration in the form of tablets or lozenges formulated in a conventional manner. Other methods of oral delivery of compounds will be known to the skilled artisan and are within the scope of the invention.

Controlled-Release Administration

Controlled-release (or sustained-release) preparations may be formulated to extend the activity of the compound and reduce dosage frequency. Controlled-release preparations can also be used to effect the time of onset of action or other characteristics, such as blood levels of the compound, and consequently affect the occurrence of side effects.

Controlled-release preparations may be designed to initially release an amount of a compound that produces the desired therapeutic effect, and gradually and continually release other amounts of the compound to maintain the level of therapeutic effect over an extended period of time. In order to maintain a near-constant level of a compound in the body, the compound can be released from the dosage form at a rate that will replace the amount of compound being metabolized and/or excreted from the body. The controlled-release of a compound may be stimulated by various inducers, e.g., change in pH, change in temperature, enzymes, water, or other physiological conditions or molecules.

Controlled-release systems may include, for example, an infusion pump which may be used to administer the compound in a manner similar to that used for delivering insulin or chemotherapy to the body generally, or to specific organs or tumors. Typically, using such a system, the compound is administered in combination with a biodegradable, biocompatible polymeric implant that releases the compound over a controlled period of time at a selected site. Examples of polymeric materials include polyanhydrides, polyorthoesters, polyglycolic acid, polylactic acid, polyethylene vinyl acetate, and copolymers and combinations thereof. In addition, a controlled release system can be placed in proximity of a therapeutic target, thus requiring only a fraction of a systemic dosage.

The compounds of the invention may be administered by other controlled-release means or delivery devices that are well known to those of ordinary skill in the art. These include, for example, hydropropylmethyl cellulose, other polymer matrices, gels, permeable membranes, osmotic systems, multilayer coatings, microparticles, liposomes, microspheres, or the like, or a combination of any of the above to provide the desired release profile in varying proportions. Other methods of controlled-release delivery of compounds will be known to the skilled artisan and are within the scope of the invention.

Inhalation Administration

The compound may also be administered directly to the lung by inhalation. For administration by inhalation, a compound may be conveniently delivered to the lung by a number of different devices. For example, a Metered Dose inhaler ("MDI") which utilizes canisters that contain a suitable low boiling point propellant, e.g., dichlorodifluoromethane, trichlorofluoromethane, dichlorotetrafluoroethane, carbon dioxide or other suitable gas may be used to deliver a compound directly to the lung. MDI devices are available from a number of suppliers such as 3M Corporation, Aventis, Boehringer Ingleheim, Forest Laboratories, Glaxo-Wellcome, Sobering Plough and Vectors.

Alternatively, a Dry Powder Inhaler (DPI) device may be used to administer a compound to the lung. DPI devices typically use a mechanism such as a burst of gas to create a cloud of dry powder inside a container, which may then be inhaled by the patient. DPI devices are also well known in the art and may be purchased from a number of vendors which include, for example, Fisons, Glaxo-Wellcome, inhale Therapeutic Systems, ML Laboratories, Qdose and Vectura. A popular variation is the multiple dose DPI ("MDDPI") system, which allows for the delivery of more than one therapeutic dose, MDDPI devices are available from companies such as AstraZeneca, GlaxoWellcome, IVAX, Schering Plough, SkyePharma and Vectura. For example, capsules and cartridges of gelatin for use in an inhaler or insufflator may be formulated containing a powder mix of the compound and a suitable powder base such as lactose or starch for these systems.

Another type of device that may be used to deliver a compound to the lung is a liquid spray device supplied, for example, by Aradigm Corporation. Liquid spray systems use extremely small nozzle holes to aerosolize liquid compound formulations that may then be directly inhaled info the lung. For example, a nebulizer device may be used to deliver a compound to the lung. Nebulizers create aerosols from liquid compound formulations by using, for example, ultrasonic energy to form fine particles that may be readily inhaled. Examples of nebulizers include devices supplied by Sheffield/Systemic Pulmonary Delivery Ltd., Aventis and Batelle Pulmonary Therapeutics.

In another example, an electrohydrodynamic ("EHD") aerosol device may be used to deliver a compound to the lung. EHD aerosol devices use electrical energy to aerosolize liquid compound solutions or suspensions. The electrochemical properties of the compound formulation are important parameters to optimize when delivering this compound to the lung with an EHD aerosol device. Such optimization is routinely performed by one of skill in the art. Other methods of infrapulmonary delivery of compounds will be known to the skilled artisan and are within the scope of the invention.

Liquid compound formulations suitable for use with nebulizers and liquid spray devices and EHD aerosol devices will typically include the compound with a pharmaceutically acceptable carrier, in one exemplary embodiment, the pharmaceutically acceptable carrier is a liquid such as alcohol, water, polyethylene glycol or a perfluorocarbon. Optionally, another material may be added to alter the aerosol properties of the solution or suspension of the compound. For example, this material may be a liquid such as an alcohol, glycol, polyglycol or a fatty acid. Other methods of formulating liquid compound solutions or suspensions suitable for use in aerosol devices are known to those of skill in the art.

Depot Administration

The compound may also be formulated as a depot preparation. Such long-acting formulations may be administered by implantation (e.g., subcutaneously or intramuscularly) or by intramuscular injection. Accordingly, the compounds may be formulated with suitable polymeric or hydrophobic materials such as an emulsion in an acceptable oil or ion exchange resins, or as sparingly soluble derivatives such as a sparingly soluble salt. Other methods of depot delivery of compounds will be known to the skilled artisan and are within the scope of the invention.

Topical Administration

For topical application, the compound may be combined with a carrier so that an effective dosage is delivered, based on the desired activity ranging from an effective dosage, for example, of 1.0 µM to 1.0 mM. In one aspect of the invention, a topical compound can be applied to the skin. The carrier may be in the form of, for example, and not by way of limitation, an ointment, cream, gel, paste, foam, aerosol, suppository, pad or gelled stick.

A topical formulation may also consist of a therapeutically effective amount of the compound in an ophthalmologically acceptable excipient such as buffered saline, mineral oil, vegetable oils such as corn or arachis oil, petroleum jelly, Miglyol 182, alcohol solutions, or liposomes or liposome-like products. Any of these compounds may also include preservatives, antioxidants, antibiotics, immunosuppressants, and other biologically or pharmaceutically effective agents which do not exert a detrimental effect on the compound. Other methods of topical delivery of compounds will be known to the skilled artisan and are within the scope of the invention.

Suppository Administration

The compound may also be formulated in rectal formulations such as suppositories or retention enemas containing conventional suppository bases such as cocoa butter or other glycerides and binders and carriers such as triglycerides, microcrystalline cellulose, gum tragacanth or gelatin. Suppositories can contain the compound in the range of 0.5% to 10% by weight. Other methods of suppository delivery of compounds will be known to the skilled artisan and are within the scope of the invention.

Other Systems of Administration

Various other delivery systems are known in the art and can be used to administer the compounds of the invention. Moreover, these and other delivery systems may be combined and/or modified to optimize the administration of the compounds of the present invention. Exemplary formulations using the compounds of the present invention are described below (the compounds of the present invention are indicated as the active ingredient, but those of skill in the art will recognize that pro-drugs and compound combinations are also meant to be encompassed by this term):

Formulation 1

Hard gelatin capsules are prepared using the following ingredients;

TABLE 7

| Ingredients | (mg/capsule) |
|---|---|
| Active Ingredient | 250.0 |
| Starch | 305.0 |
| Magnesium stearate | 5.0 |

The above ingredients are mixed and tied into hard gelatin capsules in 560 mg quantities.

Formulation 2

A tablet formula is prepared using the following ingredients;

TABLE 8

| Ingredients | (mg/tablet) |
|---|---|
| Active Ingredient | 250.0 |
| Cellulose, microcrystalline | 400.0 |
| Colloidal silicon dioxide | 10.0 |
| Stearic acid | 5.0 |

The components are blended and compressed to form tablets, each weighing 665 mg.

Formulation 3

A dry powder inhaler formulation is prepared containing the following components:

TABLE 9

| Ingredients | Weight % |
|---|---|
| Active ingredient | 5 |
| Lactose | 95 |

The active ingredient is mixed with the lactose and the mixture is added to a dry powder inhaling appliance.

Formulation 4

Tablets, each containing 60 mg of active ingredient, are prepared as follows:

TABLE 10

| Ingredients | milligrams |
|---|---|
| Active ingredient | 60.0 |
| Starch | 45.0 |
| Microcrystalline cellulose | 35.0 |
| Polyvinylpyrrolidone (as 10% solution in water) | 4.0 |
| Sodium carboxymethyl starch | 4.5 |
| Magnesium stearate | 0.5 |
| Talc | 1.0 |
| Total | 150.0 |

The active ingredient, starch and cellulose are passed through a No. 20 mesh U.S. sieve and mixed thoroughly. The solution of polyvinylpyrrolidone is mixed with the resultant powders which are then passed through a 18 mesh U.S. sieve. The granules as produced are dried at 50-80° C. and passed through a 16 mesh U.S. sieve. The sodium carboxymethyl starch, magnesium stearate, and talc, previously passed through a No. 30 mesh U.S. sieve, are then added to the granules which, after mixing, are compressed on a tablet machine to yield tablets each weighing 150 mg.

Formulation 5

Capsules, each containing 80 mg of active ingredient are made as follows:

TABLE 11

| Ingredients | milligrams |
|---|---|
| Active ingredient | 80.0 |
| Starch | 109.0 |
| Magnesium stearate | 1.0 |
| Total | 190.0 |

The active ingredient, cellulose, starch, and magnesium stearate are blended, passed through a No. 20 mesh U.S. sieve, and filled into hard gelatin capsules in 190 mg quantities.

Formulation 6

Suppositories, each containing 225 mg of active ingredient, are made as follows:

TABLE 12

| Ingredients | milligrams |
|---|---|
| Active Ingredient | 225 |
| Saturated fatty acid glycerides to | 2000 |

The active ingredient is passed through a No. 60 mesh U.S. sieve and suspended in the saturated fatty acid glycerides previously melted using the minimum heat necessary. The mixture is then poured into a suppository mold of nominal 2.0 g capacity and allowed to cool.

Formulation 7

Suspensions, each containing 50 mg of active ingredient per 5.0 ml dose are made as follows:

TABLE 13

| Ingredients | milligrams |
|---|---|
| Active ingredient | 50.0 mg |
| Xanthan gum | 4.0 mg |
| Sodium carboxymethyl cellulose | (11%) |
| Microcrystalline cellulose | (89%) 50.0 mg |
| Sucrose | 1.75 g |
| Sodium benzoate | 10.0 mg |
| Flavor | q.v. |
| Color | q.v. |
| Purified water to | 5.0 ml |

The active ingredient, sucrose and xantham gum are blended, passed through a No. 10 mesh U.S. sieve, and mixed with a previously made solution of the microcrystalline cellulose and sodium carboxymethyl cellulose in water. The sodium benzoate, flavor, and color are diluted with some of the water and added with stirring. Sufficient water is then added to produce the required volume.

Formulation 8

Capsules, each containing 150 mg of active ingredient, are made as follows:

TABLE 14

| Ingredients | milligrams |
|---|---|
| Active ingredient | 150.0 |
| Starch | 407.0 |
| Magnesium stearate | 3.0 |
| Total | 560.0 |

The active ingredient, cellulose, starch, and magnesium stearate are blended, passed through a No. 20 mesh U.S. sieve, and filled into hard gelatin capsules in 560 mg quantities.

Kits

In various embodiments, the present invention can also involve kits. Such kits can include the compounds of the present invention and, in certain embodiments, instructions for administration. When supplied as a kit, different components of a compound formulation can be packaged in separate containers and admixed immediately before use. Such packaging of the components separately can, if desired, be presented in a pack or dispenser device which may contain one or more unit dosage forms containing the compound. The pack may, for example, comprise metal or plastic foil such as a blister pack. Such packaging of the components separately can also, in certain instances, permit long-term storage without losing activity of the components. In addition, if more than one route of administration is intended or more than one schedule for administration is intended, the different components can be packaged separately and not mixed prior to use. In various embodiments, the different components can be packaged in one combination for administration together.

Kits may also include reagents in separate containers such as, for example, sterile water or saline to be added to a lyophilized active component packaged separately. For example, sealed glass ampules may contain lyophilized superoxide dismutase mimetics and in a separate ampule, sterile water, sterile saline or sterile each of which has been packaged under a neutral non-reacting gas, such as nitrogen. Ampules may consist of any suitable material, such as glass, organic polymers, such as polycarbonate, polystyrene, ceramic, metal or any other material typically employed to hold reagents. Other examples of suitable containers include bottles that may be fabricated from similar substances as ampules, and envelopes that may consist of foil-lined interiors, such as aluminum or an alloy. Other containers include test tubes, vials, flasks, bottles, syringes, and the like. Containers may have a sterile access port, such as a bottle having a stopper that can be pierced by a hypodermic injection needle. Other containers may have two compartments that are separated by a readily removable membrane that upon removal permits the components to mix. Removable membranes may be glass, plastic, rubber, and the like.

In certain embodiments, kits can be supplied with instructional materials. Instructions may be printed on paper or other substrate, and/or may be supplied as an electronic-readable medium, such as a floppy disc, mini-CD-ROM, CD-ROM, DVD-ROM, Zip disc, videotape, audio tape, and the like. Detailed instructions may not be physically associated with the kit; instead, a user may be directed to an internet web site specified by the manufacturer or distributor of the kit, or supplied as electronic mail.

The following examples illustrate the present invention.

EXAMPLES

Without further elaboration, it is believed that one skilled in the art can, using the preceding description, utilize the present invention to its fullest extent. The following specific examples are offered by way of illustration and not by way of limiting the remaining disclosure.

Unless otherwise noted, all reagents were used as supplied. Activated PEG compounds were purchased either from Nektar Therapeutics, Huntsvilie, Ala. or SunBio USA, Orlnda, Calif. Chromatographic purifications were carried out using Bakerbond® octadecyl ($C_{18}$) 40 ☐M prep LC packing by J. T.

Baker. HPLC analyses were carried out either using a Waters YMC ODS-AQ™ S5 120 Å 5 μm (4.6×50 mm) column [Mobile phase A consisted of 0.50 M aqueous NaCl and mobile phase B consisted of $H_2O$—$CH_3ON$ (1:4, v/v) and a single-gradient condition (90/10 of A/B to 0/100 in 9 min) with a flow rate of 3 mL/min was used (Method A)] or an ACE 5 C18 (250×4.6 mm) column [Mobile phase A consisted of 0.60 M $NH_4Cl$ in water and mobile phase B consisted of MeOH and an isocratic run (68/32 of A/B) with a flow rate of 1 mL/min were used (Method B)] or a Waters Symmetry-Shield™ $RP_{18}$ 5 μm (4.6×250 mm) column [Mobile phase A consisted of 0.50 M LiCl/0.125 M TBAC in water and mobile phase B consisted of $CH_3CN$ and an isocratic run (95/5 of A/B) with a flow rate of 1 mL/min were used (Method C)] with UV detection at 265 nm. All the reactions were monitored and the PEGylated products were characterized by analytical HPLC, Method A. The amount of unbound M40470 present in the purified PEGylated products was determined by HPLC. An external standard method and linear least squares analysis was used to obtain the peak response calibration curve of M40470. Degree of modification or loading on the PEG was estimated by Mn analysis (ICP) in conjunction with either molecular weight of the starting activated PEG material or molecular weight of the product determined by MALDI-MS and is expressed as weight percentage. Optical rotations were measured on a Rudolph Autopol® III automatic polarimeter. Electrospray (ESI) mass spectra were obtained with ThermoQuest AQA spectrometer, LC-MS (ESI) data was obtained on a ThermoQuest AQA spectrometer coupled with Shimadzu SIL-HTC Auto Sampler with diode array detection [RP column with Ace 5 μm C18 packing (Cat# A11155; length, 5 cm; id, 2.1 mm); Single gradient condition of 10-90% C (Mobile phase B; 1.0% ammonium formate in $H_2O$; Mobile phase C: MeOH) with a flow rate of 0.2 mL/min]. MALDI-MS were recorded at HT Laboratories, San Diego, Calif., Elemental analyses were carried out either by Atlantic Microlab, Inc., Norcross, Ga. or Desert Analytics Laboratory, Tucson, Ariz. or Galbraith Laboratories, Inc., Knoxville, Tenn.

Example 1 mPEG-BTC (MW 1,857 Da, 2.00 g, 1.08 mmol) and COMPOUND XLVIII (0.603 g, 1.08 mmol) were weighed into a 100 mL 3-necked flask, flushed with $N_2$, and the reaction flask was cooled in an ice-bath. Then anhyd DMF (25 mL) was cannulated into it followed by the addition of DIPEA (0.226 mL, 1.30 mmol) while magnetically stirring under $N_2$. The cooling bath was removed after 30 min and the resulting yellow solution was stirred overnight (ca 20 h) at room temperature. Then the reaction mixture was added slowly to a stirring solution of anhyd $Et_2O$ (300 mL) and the precipitate was collected by filtration and dried under high vacuum overnight (2.17 g). The precipitate was then dissolved in $CH_2Cl_2$ (200 mL), washed successively with 50 mL portions of water (×2) and said $NaHCO_3$-brine water (4:1, v/v; ×6). Then it was dried over $Na_2SO_4$ and concentrated to about 10 mL and added slowly to stirring anhyd $Et_2O$ (100 mL). The precipitate was collected by filtration, powdered, and then triturated with anhyd $Et_2O$ (75 mL). Then it was dried under high vacuum (0.1 mmHg) to a constant weight to give M40606 (1.97 g, 79.8%) as an off-white powder: HPLC: $t_R$=4.31 min (99.6%); Loading: 74.2% based on 1.78% Mn analysed by ICP and MW of 1,857 Da for mPEG-BTC; $k_{cat}$ (stopped flow)=0.84×10$^{-1}$s$^{-1}$ (pH 8.1).

Example 2

Theses example illustrates how to prepare a superoxide dismutase mimetic of the formula VId.

These reactions produce a compound with a molecular weight of approximately 900 Da. The PEG portion of the molecule is approximately 350 Da.

(i) Activation of mPEG-OH with CDI. To a colorless solution of mPEG-OH ($M_W$ 333 Da, 1.67 g, 5.0 mmol) in anhyd DMF (20 mL), 1,1'-carbonyldimidazole (1.62 g, 10.0 mmol) was added and the resulting mixture was stirred at 37° C. for 27 h in an atmosphere of $N_2$. Most of the DMF was removed under high vacuum and the residue was dissolved in $CH_2Cl_2$ (200 mL). Then it was transferred into a separatory funnel and washed thrice with 25 ml portions of ice-cold brine-water (4:1, v/v). The organic layer was dried over MgSO4 and evaporated to dryness. The resulting light pink oil was further dried under high vacuum (0.05 mmHg) overnight at 40° C. to give mPEG-CDI (2.41 g): MS (ESI) m/z 523 (M+H)$^+$ (corresponds to n=9 in PEG).

(II) Reaction of mPEG-CDI with COMPOUND XLVIII: To a colorless solution of mPEG-CDI (128 g, 2.45 mmol) in anhyd DMF (12 mL), COMPOUND XLVIII (2.01 g, 3.60 mmol) and N,N-disopropylethylamine (0.627 mL, 3.60 mmol) were added while stirring in an atmosphere of $N_2$. The temperature of the resulting light yellow solution was brought to 60° C. quickly and stirred for 48 h under $N_2$. Most of the DMF was removed under high vacuum, the residue was dissolved in water (50 mL), and NaCl (10 g) was added. After stirring the contents for 15 min, the compound was extracted into $CH_2Cl_2$ (4×50 mL). The combined organic layers were diluted with $CH_2Cl_2$ (200 mL) and washed successively with water (2×30 mL) and brine. The dried ($Na_{22}SO_4$ extract was concentrated in vacuo and further dried under high vacuum to give 2.44 g of brownish-orange viscous residue containing 22.9% of unbound COMPOUND XLVIII by HPLC. The crude product was dissolved in anhyd 1,2-dichloroethane (40 mL), amine scavenger resin PS-isocyanate (1.46 mmol/g loading, 2.05 g, 3.0 mmol) was added, and the slurry was stirred and heated at 50° C. for 6 h. After cooling to room temperature, additional PS-isocyanate (1.0 g) was added, and stirred overnight under $N_2$. The resin was separated by filtration and was washed further with $CH_2Cl_2$. The combined filtrates were concentrated in vacuo and further dried under high vacuum to give 1.95 g of brownish viscous residue containing 1.5% of unbound COMPOUND XLVIII (HPLC, Method A). It was then subjected to chromatography over $C_{18}$ silica gel using 20-40% $CH_3CN$ in 0.50 M NaCl as eluant and the progress of the chromatography was monitored by HPLC. The fractions containing the pure compound (devoid of COMPOUND XLVIII) were combined and evaporated to dryness. The residue was dissolved in water (50 mL), NaCl (10 g) was added, stirred for 15 min, and then extracted with $CH_2Cl_2$ (4×50 mL). The combined $CH_2Cl_2$ extracts were dried over $MgSO_4$ and concentrated to a volume of ~5 mL. Then It was filtered through a fritted funnel and the solvent was removed in vacuo. The residue was co-evaporated with anhyd EtOH (2×5 mL) and dried overnight under high vacuum (0.05 mmHg) at 40° C. to give M40644 (1.40 g, 61.8%) as a brownish viscous residue: HPLC: major peaks at $t_R$=3.55 min (40.3%), 3.58 min (17.4%), and 3.62 min (40.2%); MS (ESI) m/z 888 (M-Cl)$^+$, 898 (M-2Cl+HCOO)$^+$ (corresponds to n=7 in PEG); Loading: 92.8 based on 5.50% Mn analysed by ICP: Unbound COMPOUND XLVIII (quantified by HPLC): 0.043% by weight; $k_{cat}$ (stopped flow)=1.1× 10$^{-1}$s$^{-1}$(pH 8.1).

This example illustrates how to prepare a superoxide dismutase mimetic of the formula VId with a molecular weight approximately 2 kDa.

mPEG-BTC (MW 1,857 Da, 2.00 g, 1.08 mmol) and COMPOUND XLVIII (0.603 g, 1.08 mmol) were weighed into a 100 mL 3-necked flask, flushed with $N_2$, and the reaction flask was cooled in an ice-bath. Then anhyd DMF (25 mL) was cannulated into it followed by the addition of DIPEA (0.226 mL, 1.30 mmol) while magnetically stirring under $N_2$. The cooling bath was removed after 30 min and the resulting yellow solution was stirred overnight (ca 20 h) at room temperature. Then the reaction mixture was added slowly to a stirring solution of anhyd $Et_2O$ (300 mL) and the precipitate was collected by filtration and dried under high vacuum overnight (2.17 g). The precipitate was then dissolved in $CH_2Cl_2$ (200 mL), washed successively with 50 mL portions of water (×2) and satd $NaHCO_3$-brine water (4:1, v/v; ×6). Then it was dried over $Na_2SO_4$ and concentrated to about 10 mL and added slowly to stirring anhyd $Et_2O$ (100 mL). The precipitate was collected by filtration, powdered, and then triturated with anhyd $Et_2O$ (75 mL). Then if was dried under high vacuum (0.1 mmHg) to a constant weight to give M40606 (1.97 g, 79.8%) as an off-white powder: HPLC: $t_R$=4.31 min (99.6%); Loading: 74.2% based on 1.78% Mn analysed by ICP and MW of 1,857 Da for mPEG-BTC; $k_{cat}$ (stopped flow)=$0.84 \times 10^{-1} s^{-1}$ (pH 8.1).

This example produces a compound with a molecular weight of approximately 5 kDa. mPEG-BTC (MW 5,124 Da, 1.95 g, 0.380 mmol) was weighed into a 100 mL 3-necked flask, flushed with $N_2$, and anhyd DMF (10 mL) was cannulated into it. The resulting suspension was cooled in an ice-bath and COMPOUND XLVIII (0.212 g, 0.380 mmol) followed by DIPEA (0.080 mL, 0.459 mmol) were added while magnetically stirring under $N_2$. More DMF (5 mL) was added and somewhat lighter suspension was stirred for 37 h at room temperature and then 6 h at 50° C. (no change in the ratio of product and COMPOUND XLVIII by HPLC after 15 h at room temperature). Then the reaction mixture was added slowly to a stirring solution of anhyd $Et_2O$ (225 mL), the precipitate was collected by filtration and dried under high vacuum to give 1.95 g of an off-white powder. The precipitate was then dissolved in $CH_2Cl_2$ (200 mL), washed successively with 50 mL portions of water (×2), satd $NaHCO_3$-brine water (4:1, v/v; ×3), 5% NaCl, and brine. The organic layer was dried over $Na_2SO_4$, evaporated to dryness, and the resulting solid was powdered. Then it was triturated with anhyd $Et_2O$ (75 mL) and dried under high vacuum (0.05 mmHg) to a constant weight to give M40603 (1.87 g, 88.8%) as an off-white powder: HPLC: major peak at $t_R$=4.54 min (97%); Loading: 58.6% based on 0.58% Mn analysed by ICP and MW of 5,124 Da for mPEG-BTC; $k_{cat}$ (stopped flow)=$0.72 \times 10^{-1} s^{-1}$ (pH 8.1).

This example illustrates how to prepare a superoxide dismutase mimetic of the formula VId with a molecular weight approximately 20 kDa.

mPEG-BTC (MW 21,400 Da, 1.95 g, 0.091 mmol) was weighed into a 100 mL 3-necked flask, flushed with $N_2$, and anhyd DMF (25 mL) was cannulated into it. The resulting suspension was cooled in an ice-bath and COMPOUND XLVIII (0.051 g, 0.091 mmol) followed by DIPEA (0.019 mL, 0.109 mmol) were added while magnetically stirring under $N_2$. After 15 min, the cooling bath was removed, additional DMF (5 mL) was added, and stirred overnight (ca 24 h) at room temperature. The colorless turbid solution was added slowly to a stirring solution of anhyd $Et_2O$ (300 mL), the precipitate was collected by filtration and dried under high vacuum to give 1.89 g of a white fluffy solid. Then it was dissolved in $CH_2Cl_2$ (200 mL) and washed successively with 50 mL portions of water, said $NaHCO_3$-brine water (4:1, v/v; ×2), 5% NaCl, and brine. The organic layer was dried over $Na_2SO_4$ and concentrated to ~15 mL, and slowly added to stirring anhyd $Et_2O$ (150 mL). The precipitate was collected by filtration, washed with $Et_2O$, and dried briefly. Then it was triturated with anhyd $Et_2O$ (75 mL) and dried under high vacuum (0.05 mmHg) to a constant weight to give M40605 (1.86 g, 93.4%) as a white fluffy solid: HPLC; $t_R$=4.87 min (98%); Loading: quantitative based on Mn analysed by ICP and MW of 21,400 Da for mPEG-BTC; $k_{cat}$ (stopped flow)= $1.03 \times 10^1 s^{-1}$ (pH 8.1).

Example 3

This example illustrates how to prepare a superoxide dismutase mimetic of the formula VIb.

mPEG-SPA (MW 5,105 Da, 1.94 g, 0.380 mmol) and COMPOUND XLVIII (0.212 g, 0.360 mmol) were weighed into a 100 mL 3-necked flask, flushed with $N_2$, and the reaction flask was cooled in an ice-bath. Then anhyd DMF (25 mL) was cannulated into it followed by the addition of DIPEA (0.080 mL, 0.450 mmol) while magnetically stirring under $N_2$. After 15 min, the cooling bath was removed and the resulting yellow solution was stirred overnight (ca 27 h) at room temperature. Then the reaction mixture was added slowly to a stirring solution of anhyd $Et_2O$ (300 mL), the precipitate was collected by filtration and dried under high vacuum overnight to give 2.10 g of a white powder. The precipitate was then dissolved in $CH_2Cl_2$ (200 mL), washed successively with 50 mL portions of water (×2), satd $NaHCO_3$-brine water (4:1, v/v), 5% NaCl, and brine. Then it was dried over $Na_2SO_4$ and concentrated to about 10 mL and added slowly to stirring anhyd $Et_2O$ (100 mL). The precipitate was collected by filtration and then triturated with anhyd $Et_2O$ (75 mL). Then it was dried under high vacuum (0.05 mmHg) to a constant weight to give M40602 (1.98 g, 94.3%) as a white powder: HPLC: $t_R$=4.48 min (99.1%); Loading: 70.7% based on 0.70% Mn analysed by ICP and MW of 5,105 Da for mPEG-SPA; $k_{cat}$ (stopped flow)=$0.90 \times 10^{-1} s^{-1}$ (pH 8.1).

Example 4

This example illustrates how to prepare a superoxide dismutase mimetic of the formula VIb.

This reaction produces a compound of approximately 2 kDa in the PEG portion of the molecule.

mPEG-SPA (MW 2,000 Da, 2.00 g, 1.00 mmol) and COMPOUND. XLVIII (0.659 g, 1.00 mmol) were weighed info a 100 mL 3-necked flask, flushed with $N_2$, and the reaction flask was cooled in an ice-bath. Then anhyd DMF (25 mL) was cannulated into it followed by the addition of DIPEA (0.209 mL, 1.20 mmol) while magnetically stirring under $N_2$. The resulting yellow solution was stirred overnight (ca 18 h) at room temperature. Then the reaction mixture was added slowly to a stirring solution of anhyd $Et_2O$ (300 mL), the precipitate was collected by filtration and dried under high vacuum to give 2.35 g of an off-white powder. The precipitate was then dissolved in $CH_2Cl_2$ (200 mL), washed successively with 50 mL portions of water (×2), said $NaHCO_3$-brine water (4:1, v/v), and brine. Then it was dried over $Na_2SO_4$ and concentrated to about 10 mL and added slowly to stirring anhyd $Et_2O$ (100 mL). The precipitate was collected by filtration, powdered, and then triturated with anhyd $Et_2O$ (75 mL). Then if was dried under high vacuum (0.05 mmHg) to a constant weight to give M40604 (2.13 g, 86.9%) as a white powder: HPLC: $t_R$=4.19 min (99.9%); Loading: 75% based on 1.68% Mn analysed by ICP and MW of 2,000 Da for mPEG-SPA; $k_{cat}$ (stopped flow)=$102 \times 10^{-1} s^{-1}$ (pH 8.1).

This reaction produces a compound of approximately 5 kDa in the PEG portion of the molecule.

mPEG-SPA (MW 5,105 Da, 1.94 g, 0.380 mmol) and COMPOUND XLVIII (0.212 g, 0.380 mmol) were weighed into a 100 mL 3-necked flask, flushed with $N_2$, and the reaction flask was cooled in an ice-bath. Then anhyd DMF (25 mL) was cannulated into it followed by the addition of DIPEA (0.080 mL, 0.459 mmol) while magnetically stirring under $N_2$. After 15 min, the cooling bath was removed and the resulting yellow solution was stirred overnight (ca 27 h) at room temperature. Then the reaction mixture was added slowly to a stirring solution, of anhyd $Et_2O$ (300 mL), the precipitate was collected by filtration and dried under high vacuum overnight to give 2.10 g of a white powder. The precipitate was then dissolved in $CH_2Cl_2$ (200 mL), washed successively with 50 mL portions of water (×2), satd $NaHCO_3$-brine water (4:1, v/v), 5% NaCl, and brine. Then it was dried over $Na_2SO_4$ and concentrated to about 10 mL and added slowly to stirring anhyd $Et_2O$ (100 mL). The precipitate was collected by filtration and then triturated with anhyd $Et_2O$ (75 mL). Then It was dried under high vacuum (0.05 mmHg) to a constant weight to give M40602 (1.98 g, 94.3%) as a white powder: HPLC: $t_R$=4.48 min (99.1%); Loading: 70.7% based on 0.70% Mn analysed by ICP and MW of 5,105 Da for mPEG-SPA; $k_{cat}$ (stopped flow)=$0.90 \times 10^{-1} s^{-1}$ (pH 8.1).

This reaction produces a compound of approximately 20 kDa in the PEG portion of the molecule.

mPEG-SPA (MW 20,500 Da, 2.00 g, 0.097 mmol) and COMPOUND XLVIII (0.054 g, 0.097 mmol) were weighed into a 100 mL 3-necked flask, flushed with $N_2$, and anhyd DMF (20 mL) was cannulated into it followed by the addition of DIPEA (0.020 mL, 0.115 mmol) while magnetically stirring under $N_2$. The suspension was heated to 35° C. over a 15 min period to obtain a clear solution, which was then stirred overnight (ca 26 h) at room temperature. Then the reaction mixture was added slowly to a stirring solution of anhyd $Et_2O$ (200 mL), the precipitate was collected by filtration and dried under high vacuum to give 1.95 g of a white solid. The precipitate was then dissolved in said $NaHCO_3$ (50 mL) and extracted with $CH_2Cl_2$ (2×100 mL), washed successively with 50 mL portions of water (×2), satd $NaHCO_3$-brine water (4:1, v/v). The combined organix extracts were washed successively with 50 mL portions of water (×2) and brine. Then if was dried over $Na_2SO_4$ and concentrated to about 20 mL and added slowly to stirring anhyd $Et_2O$ (150 mL). The precipitate was collected by filtration and washed with anhyd $Et_2O$. The resulting off-white and somewhat a sticky solid was dried under high vacuum to a constant weight to give M40617 (1.70 g, 82.9%): HPLC: $t_R$=5.10 min (98.9%); Loading: 69.2% based on 0.18% Mn analysed by ICP and MW of 20,600 Da for mPEG-SPA; Unbound COMPOUND XLVIII (quantified by HPLC): 0.002% by weight.

Example 5

This reaction produces a molecule with approximately one kDa in the PEG portion of the molecule.

To a solution of mPEG-isocyanate (MW 1,077 Da, 2.50 g, 2.32 mmol) in anhyd $CH_2Cl_2$ (10 mL), COMPOUND XLVIII (3.08 g, 5.52 mmol) was added at ice-bath temperature while stirring in an atmosphere of $N_2$. The viscous solution was stirred overnight (ca 20 h) at room temperature and for 3 h at 40° C. Then the reaction mixture was diluted with $CH_2Cl_2$ (200 mL) and water (50 mL). After stirring well, the contents were transferred into a separatory funnel and the layers were separated. The $CH_2Cl_2$ layer was further washed with water (2×50 mL and 1×100 mL) and dried over $Na_2SO_4$. Solvent was removed in vacuo and the resulting yellow solid was dried under high vacuum to give 3.06 of the crude product containing <1% of unbound COMPOUND XLVIII by HPLC. About half of this material was subjected to chromatography over $C_{18}$ silica gel using 20-35% $CH_3CN$ in 0.50 M NaCl as eluant and the progress of the chromatography was monitored by HPLC. The fractions containing the pure compound (devoid of COMPOUND XLVIII) were combined and most of the $CH_3CN$ was removed in vacuo. Then it was diluted with water (50 mL), NaCl (10 g) was added, stirred for 15 min, and then extracted with $CH_2Cl_2$ (4×50 mL). The combined $CH_2Cl_2$ extracts were dried over $Na_2SO_4$ and the solvent was removed in vacuo. The resulting gummy residue was dissolved in minimum amount of $CH_2Cl_2$ and added slowly to stirring anhyd $Et_2O$ (100 mL). The precipitate was collected by quick filtration, washed with more $Et_2O$, and Immediately transferred into a vacuum desiccator (hygroscopic). Then if was dried under high vacuum (0.05 mmHg) at 40° C. for 2 d to give M40643 (0.902 g, 46.5%) as an off-white solid: HPLC: major peaks at $t_R$=3.91 min (96.9%) and 4.40 min (2.8%); MS (MALDI) m/z calculated for $C_{73}H_{139}Cl_2N_7O_{25}SMn$ (for n=23 in PEG) 1,638 $(M-Cl)^+$, 1754 $(M-2Cl+DHB)^+$; found 1,637 $(M-Cl)^+$, 1,755 $(M-2Cl+DHB)^+$; Loading: 89.8% based on 2.95% Mn analysed (duplicate) by ICP: Unbound COMPOUND XLVIII (quantified by HPLC): 0.002% by weight; $k_{cat}$ (stopped flow)=$1.0 \times 10^{-1} s^{-1}$ (pH 8.1).

This reaction produces a compound of approximately 2 kDa in the PEG portion of the molecule.

mPEG-isocyanate (MW 2,089 Da, 4.40 g, 2.10 mmol) was weighed info a 250 mL 3-necked flask equipped with a pressure equalizing funnel, flushed with $N_2$, and the reaction flask was cooled in an ice-bath. Then anhyd $CH_2Cl_2$ (30 mL) was cannulated into it and a solution of COMPOUND XLVIII (1.17 g, 2.10 mmol) in anhyd $CH_2Cl_2$ (10 mL) was added slowly (ca 20 min) with stirring in an atmosphere of $N_2$. The cooling bath was removed and the light yellow solution was stirred at room temperature for 6 h. Solvent was removed in vacuo and the resulting off-white residue was partitioned between $CH_2Cl_2$ (500 mL) and water (100 mL). The turbid layers were separated and the organic layer was washed successively with water (5×50 mL). The combined aqueous layers, including the first one, were allowed to stand overnight in a separately funnel and the organic layer was separated. The combined organic layers were dried over $MgSO_4$, filtered through celite, and evaporated to dryness. To remove the traces of COMPOUND XLVIII present in the product, the above solid was dissolved in $CHCl_3$ (200 mL) and washed with water (50 mL). The faintly turbid $CHCl_3$ layer was dried over MgSO4, filtered through celite, and evaporated to dryness to give 4.20 g of beige solid. It was co-evaporated with anhyd $Et_2O$ (2×100 mL) and the residue was triturated with anhyd $Et_2O$ (20 mL). The solid was collected by filtration, further washed with anhyd $Et_2O$, and finally dried under high vacuum (0.1 mmHg) to a constant weight to give M40618 (4.10 g, 76.5%) as an off-white powder: HPLC; $t_R$=4.09 min (99.3%); MS (MALDI) m/z calculated for $C_{113}H_{219}Cl_2N_7O_{45}SMn$ (for n=43 in PEG) 2,517 $(M-Cl)^+$; found 2,516 $(M-Cl)^+$; Loading: 77.2% based on 1.88% Mn analysed by ICP; Unbound COMPOUND XLVIII (quantified by HPLC): 0.01% by weight; $k_{cat}$ (stopped flow)=$0.84 \times 10^{-1} s^{-1}$ (pH 8.1).

These methods produce a compound with approximately 5 kDa in the PEG portion of the molecule.

Method A. mPEG-isocyanate (MW 4,881 Da, 4.00 g, 0.823 mmol) was weighed into a 250 mL round-bottomed flask equipped with a pressure equalizing funnel, flushed with $N_2$, and the reaction flask was cooled in an ice-bath. Then anhyd $CH_2Cl_2$ (30 mL) was cannulated into if and a solution of COMPOUND XLVIII (0.460 g, 0.823 mmol) in anhyd $CH_2Cl_2$ (10 mL) was added slowly (ca 30 min) with stirring in an atmosphere of $N_2$. The cooling bath was removed and the light yellow solution was stirred at room temperature for 8 h. Solvent was removed in vacuo, the residue was dissolved in water (25 mL), loaded into loaded into Slide-A-Lyzer dialysis cassettes (4, MW cutoff 3,500; Pierce), and exhaustively dialyzed against distilled water (3 L, 20 h). The product solution from the cassettes was collected (~60 mL), diluted with water (40 mL), and NaCl (20 g) was added. After stirring for 15 min under $N_2$, the product was extracted info $CH_2Cl_2$ (3×75 mL), and the combined organic extracts were dried over $Na_2SO_4$. The solvent was removed in vacuo, the residue dried under high vacuum briefly, and powdered. Then it was triturated with anhyd $Et_2O$ (150 mL), the solid was collected by filtration, further washed with anhyd $Et_2O$, and finally dried under high vacuum: (0.05 mmHg) to a constant weight to give M40601 (3.60 g, 82%) as an off-white powder: HPLC; major peaks at $t_R$=4.60 min (97.3%) and 4.88 min (2.5%); MS (MALDI) m/z calculated for $C_{239}H_{471}Cl_2N_7O_{106}SMn$ (for n=106 in PEG) 5,293 (M-Cl)$^+$; found 5,287 (M-Cl)$^+$; Loading: 76.7% based on 0.79% Mn analysed by ICP; Unbound COMPOUND XLVIII (quantified by HPLC): 0.004% by weight; $k_{cat}$ (stopped flow)=0.85×10$\square^{-1}$s$^{-1}$ (pH 8.1).

Method B.

(i) Activation of mPEG-NH$_2$ with DSC. mPEG-NH$_2$ (MW 5,254 Da for starting mPEG-OH, 1.89 g, 0.38 mmol) was dissolved in anhyd dioxane (15 mL) by slightly warming and allowed to cool to room temperature in an atmosphere of $N_2$. Then a slurry of N,N'-disuccinimidyl carbonate (0.640 g, 2.50 mmol) in anhyd acetone (15 mL) was cannulated followed by the addition of DMAP (0.305 g, 2.50 mmol) in anhyd acetone (15 mL) over a 15 min period. The resulting solution was stirred for 4 h at room temperature and most of the acetone was removed in vacuo. The resulting viscous solution was added to stirring anhyd $Et_2O$ (150 mL) and the white precipitate was collected by vacuum filtration. This material was re-precipitated from $CH_2Cl_2$ (10 mL) using anhyd $Et_2O$ (100 mL) thrice, thoroughly washed with anhyd $Et_2O$, and dried overnight under high vacuum (0.3 mmHg) to give activated mPEG derivative (2.03 g) as white powder (upon breaking the cake): MALDI-MS (ESI) m/z 5,225 (M+H)$^+$ (corresponds to n ~114 in PEG).

(ii) Reaction of activated mPEG-derivative with COMPOUND XLVIII: The above activated mPEG-derivative (1.98 g, 0.351 mmol based on 100% conversion) and COMPOUND XLVIII (0.196 g, 0.351 mmol) were weighed into a 100 mL round-bottomed flask equipped with a Claisen adapter and flushed with $N_2$. Then anhyd DMF (15 mL) was cannulated into it and stirred overnight (21 h) at room temperature and for 4 h at 40° C. under $N_2$. The reaction mixture was allowed to cool to room temperature and the product was precipitated by pouring into anhyd $Et_2O$ (150 mL). The off-white colored precipitate was collected by vacuum filtration, washed with $Et_2O$, and dried under high vacuum (1.92 g). The crude product was dissolved in water (15 mL), pH was adjusted to ~9 by a few drops of satd NaHCO$_3$, loaded into loaded info Slide-A-Lyzer dialysis cassettes (3, MW cutoff 3,500; Pierce), and exhaustively dialyzed against distilled water (3 L, 42 h). The product solution from the cassettes was collected (~50 mL), diluted with water (30 mL), and NaCl (16 g) was added. After stirring for 15 min under $N_2$, $CH_2Cl_2$ (50 mL) was added, stirred for another 15 min, and transferred info a separatory funnel. The layers were separated and the aqueous layer was further extracted with $CH_2Cl_2$ (3×50 mL). The combined organic extracts were washed with brine (50 mL) and dried Na$_2$SO$_4$. The solvent was removed in vacuo, the residue dissolved in $CH_2Cl_2$ (10 mL), and the product was precipitated by adding to stirring anhyd $Et_2O$ (100 mL). The precipitate collected by vacuum filtration, further washed with anhyd $Et_2O$, and the white filter cake was dried under high vacuum briefly. Then if was powdered and dried under high vacuum (0.05 mmHg) to a constant weight to give M40601 (1.74 g, 87.4%) as a white powder: HPLC: $t_R$=4.70 min (99.5%); MS (MALDI) m/z calculated for $C_{255}H_{503}Cl_2N_7O_{116}SMn$ (for n=114 in PEG) 5,645 (M-Cl)$^+$; found 5,643 (M-Cl)$^+$; Loading: 70.1% based on 0.68% Mn analysed by ICP; Unbound COMPOUND XLVIII (quantified by HPLC): 0.007% by weight; $k_{cat}$ (stopped flow)=0.80×10$\square^{-1}$s$^{-1}$ (pH 8.1).

This produces a compound with approximately 20 kDa in the PEG portion.

mPEG-isocyanate (MW 21,514 Da, 4.82 g, 0.224 mmol) was weighed into a 250 mL round-bottomed flask equipped with a pressure equalizing funnel, flushed with $N_2$, and anhyd $CH_2Cl_2$ (25 mL) was cannulated into it. The resulting viscous solution was cooled in an ice-bath, COMPOUND XLVIII (0.626 g, 1.12 mmol) was added, and stirred overnight (ca 18 h) at morn temperature under $N_2$. Solvent was removed in vacuo, the residue dissolved in anhyd 1,2-dichloroethane (40 mL), amine scavenger resin PS-isocyanate (1.46 mmol/g loading, 1.84 g, 2.69 mmol) was added, and the slurry was stirred and heated for 16 h at 60° C. under $N_2$. Another 1.84 g batch of PS-isocyanate was added and stirring continued overnight at 40° C. After cooling to room temperature, the resin was separated by filtration and washed further with $CH_2Cl_2$. The combined filtrates were concentrated in vacuo and further dried under high vacuum to give 5.01 g of the product containing 15.2% of unbound COMPOUND XLVIII (HPLC, Method A). It was then dissolved in water (55 mL), loaded into loaded into Slide-A-Lyzer dialysis cassettes (7, MW cutoff 3,500; Pierce), and exhaustively dialyzed against distilled water (6 L, 17 h). The product solution from the cassettes was collected (~100 mL including washings) and NaCl (20 g) was added. The product was extracted into $CH_2Cl_2$ (4×75 mL), and the combined organic extracts were dried over Na$_2$SO$_4$. The solvent was removed in vacuo and the residue was dried under high vacuum to give 4.83 g of a whitish solid containing 1.6% of unbound COMPOUND XLVIII. The above material was dissolved in CHCl$_3$ (500 mL), washed with water (4×100 mL) and brine (100 mL). The CHCl$_3$ extract was dried over Na$_2$SO$_4$, concentrated in vacuo, and the residual viscous solution was added to stirring anhyd $Et_2O$ (400 mL). The precipitate was collected by vacuum filtration, washed with more $Et_2O$, and dried under high vacuum (0.05 mmHg) over the weekend to give M40619 (4.37 g, 88.1%) as a white fluffy solid: HPLC: $t_R$=5.01 min (99.3%); MS (MALDI) m/z calculated for $C_{1003}H_{1999}Cl_2N_7O_{490}SMn$ (for n=488 in PEG) 22,121 (M-Cl)$^+$; found 22,117 (M-Cl)$^+$; Loading: 78% based on 0.195% Mn analysed (duplicate) by ICP: Unbound COMPOUND XLVIII (quantified by HPLC): 0.002% by weight; $k_{cat}$ (stopped flow)=1.4×10$\square^{-1}$s$^{-1}$ (pH 8.1).

Example 6

This example illustrates how to prepare a superoxide dismutase mimetic of the formula VIa.

mPEG-ButyrALD (1.61 g, 0.320 mmol) and M40470 (0.215 g, 0.384 mmol) were weighed into a 100 mL round-bottomed flask equipped with a Claisen adapter and flushed with $N_2$. Then anhyd 1,2-dichloroethane (20 mL) was cannulated, reaction flask was cooled in an ice-bath, and HOAc (0.37 mL, 6.40 mmol) and sodium: triacetoxyborohydride (0.170 g, 0.80 mmol) were added. The reaction mixture was stirred overnight (ca 22 h) at room temperature in an atmosphere of $N_2$. Most of the solvent was removed in vacuo and the residue was treated with satd $NaHCO_3$ (50 mL) and stirred for 30 min. Then it was diluted with water (50 mL), extracted with $CH_2Cl_2$ (3×50 mL), and the combined organic extracts were washed with brine (50 mL). The dried ($Na_2SO_4$) extracts were concentrated in vacuo and dried under high vacuum to give 1.79 g of an off-white solid. The crude product was dissolved in water (20 mL), loaded into loaded into Slide-A-Lyzer dialysis cassettes (3, MW cutoff 3,500; Pierce), and exhaustively dialyzed against distilled water (4×1.5 L) in succession (changed water after 2 h during first three experiments and left over the weekend last time). The water used in last two dialysis experiments were combined and concentrated to ~1000 mL and NaCl (100 g) was added. Then if was extracted with $CH_2Cl_2$ (4×150 mL) and the combined organic extracts were dried $Na_2SO_4$. The solvent was removed in vacuo and the residue dried under high vacuum to give 1.58 g of whitish solid containing <1% of unbound M40470 by HPLC. This was combined with another 0.16 g of the product isolated in a different experiment identically run on the same lot of mPEG-ButyrALD (0.201 g, 0.040 mmol) and partitioned between. $CH_2Cl_2$ (200 mL) and water (50 mL). The layers were separated, the aqueous layer was further extracted with $CH_2Cl_2$ (2×75 mL), and the combined extracts were washed with brine (50 mL). The dried ($Na_2SO_4$) extracts were concentrated, filtered through a fritted funnel, and added to stirring anhyd $Et_2O$. The precipitate was collected by vacuum filtration and further washed with anhyd $Et_2O$. Then it was powdered and dried under high vacuum (0.10 mmHg) to a constant weight to give M40628 (1.48 g, 65.8%) as an off-white powder; HPLC: $t_R$=4.56 min (98.5%); MS (MALDI) m/z calculated for $C_{282}H_{556}Cl_2N_6O_{128}SMn$ (for n=127 in PEG) 6,204 (M-Cl)$^+$; found 6,209 (M-Cl)$^+$; Loading: 100% based on 0.895% Mn analysed (duplicate) by ICP; Unbound M40470 (quantified by HPLC); 0.006% by weight; $k_{cat}$ (stopped flow)=1.0-1.5×58$^{-1}$s$^{-1}$ (pH 8.1).

Example 7

This example illustrates methods that can be used to prepare superoxide dismutase mimetic-Cl and superoxide dismutase mimetic-$NH_2$ compounds for use in producing PEGylated superoxide dismutase mimetic molecules.

This synthesis follows the procedure described in Examples 4 and 5 of U.S. patent application Ser. No. 10/702,407, which is incorporated in its entirety by reference.

The template Synthesis of the superoxide dismutase mimetic-Cl compound of formula IX can be performed as follows.

Tetraamine hydrochloride (5.00 g, 12.5 mmol) was suspended in 1-propanol (150 mL), and the flask was purged thoroughly with $N_2$. DIPEA (8.70 mL, 50.0 mmol) was then added resulting a homogeneous solution, and after 5 min, $MnCl_2$ (1.58 g, 12.5 mmol) was added. The solution was stirred at room temperature for 25 min and 4-chloro-2,6-pyridinedicarboxaldehyde (2.13 g, 12.5 mmol) was added in one portion. The resulting deep orange solution was heated to 95° C. and maintained at that temperature for 5 h. The reaction mixture was then allowed to cool and stir overnight (15 h) at room temperature. Once again the reaction mixture was heated to 95° C. and stirred for additional 7 h to complete the reaction. After cooling the reaction mixture to room temperature, the solvent was removed in vacuo and the dark reddish brown oil was dried under high vacuum overnight. Distilled $H_2O$ (200 mL) was added to the above residue, and after the addition of NaCl (40 g), the mixture was stirred for 1 h at room temperature. The resulting suspension was filtered through a fritted funnel and the orange filter cake was dried under high vacuum at 50° C. over the weekend to give M40481 (6.74 g, 105%, contains some NaCl): HPLC: 97.6% ($t_R$=2.12 min; Method A), MS (ESI) m/z 487 (M-2Cl+ HCOO)$^+$.

A solution of the above (6.5 g, 12.1 mmol) in anhydrous EtOH (60 mL) was cooled in an ice-bath and $NaBH_4$ (1.91 g, 50.5 mmol) was added in one portion while magnetically stirring in an atmosphere of $N_2$. After 10 min, the ice-bath was removed, and the reaction mixture was allowed to warm to room temperature and stirred for 1 h. Anhyd MeOH (60 mL) was added slowly to the reaction mixture and the resulting solution was stirred at room temperature for 2 h. The reaction mixture was then evaporated to dryness and distilled $H_2O$ (100 mL) and NaCl (2 g) were added. The resulting suspension was stirred for 1 h at room temperature and then extracted with $CH_2Cl_2$ (3×150 mL). The combined $CH_2Cl_2$ extracts were dried over MgSO4, filtered, and evaporated to dryness. Then the off-white solid was further dried under high vacuum overnight at 40° C. to give M40409 (4.34 g, 69.2%): HPLC: 98.4% ($t_R$=2.86 min; Method A), MS (ESI) m/z 491 (M-2Cl+ HCOO)$^+$.

The synthesis is illustrated below:

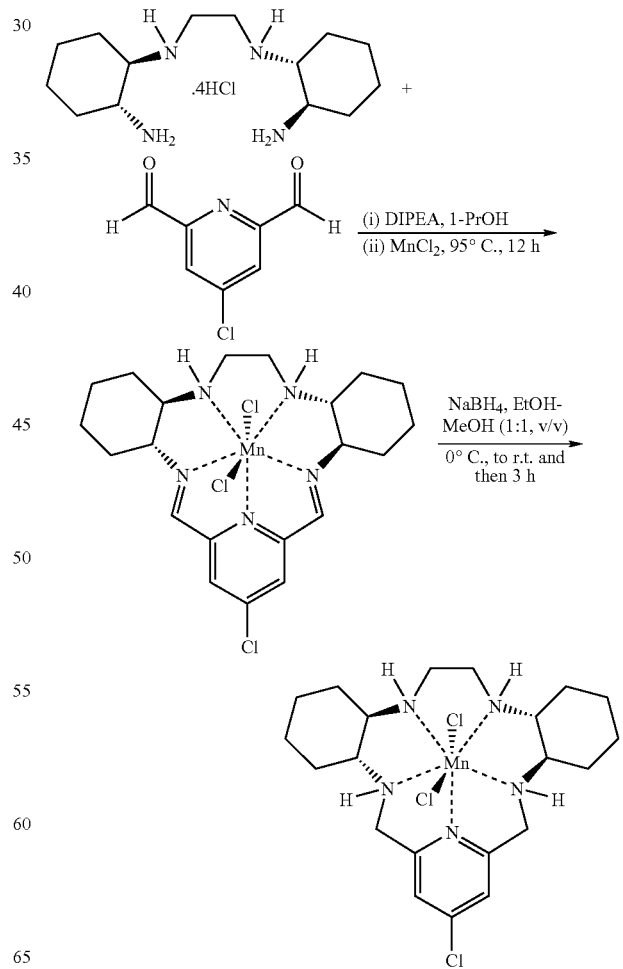

Example 8

This example provides a method for the preparation of compound XLVIII.

A 500 mL 3-necked round-bottom flask was charged with 2-mercaptoethylamine hydrochloride or cysteamine hydrochloride (6.48 g, 57.0 mmol) and flushed with $N_2$. Then anhyd DMF (190 mL) was cannulated into the flask while magnetically stirring the contents in an atmosphere of Ar. The solution was cooled in an ice-bath and 1,1,3,3-tetramethylguanidine (15.8 mL, 125.9 mmol) was added with a pipette. The resulting white suspension was stirred for 1 h and M40409 (9.84 g, 19.0 mmol) was added as a solid in one portion. The light green suspension was slowly warmed to r.t. and stirred overnight for a total of 20 h. Then the reaction mixture was transferred into a round-bottom flask and the solvent was removed under high vacuum (bath temp, ~30° C.). The residue was dissolved in distilled $H_2O$ (250 mL) and NaCl (37.5 g) was added while stirring the aqueous solution vigorously under $N_2$. A thick colorless gelatinous material was formed, which was broken up with a glass rod, and stirred with $CH_2Cl_2$ (250 mL) with occasional shaking. The biphasic system was transferred into a 1000 mL separator/funnel and the layers separated. The aqueous layer was further extracted with $CH_2Cl_2$ (3×150 mL) and the combined organic extracts were washed with 20% NaCl and brine (150 mL each). The dried ($Na_2SO_4$) extracts were evaporated to dryness and the pale yellow foam was dissolved in anhyd EtOH. After filtration (Whatman), solvent was removed in vacuo, and the residue was co-evaporated with anhyd EtOH (50 mL). The resulting pale yellow foam (more like an yellowish tinge) was dried under high vacuum at 40° C. to a constant weight (~36 h) to give M40470 (10.63 g, 100.2%); $[\alpha]_D^{24}=-61.4$ (c 1.04, MeOH); HPLC: 97.9% ($t_R$=2.14 min; Method A), 97.0% ($t_R$=11.51 min; Method B), 98.4% ($t_R$=6.40 min: Method C); LC-MS (ESI) m/z 532 (M-2Cl+HCOO)$^+$ ($t_R$=1197 min). Anal Calcd for $C_{23}H_{40}Cl_2MnN_6S$. 11/2$H_2O$: C, 47.18; H, 7.40; Cl, 12.11; Mn, 9.38; N, 14.35; S, 5.48: Found: C, 47.53; H, 7.55; Cl, 12.06; Mn, 9.07; N, 14.67; S, 5.73.

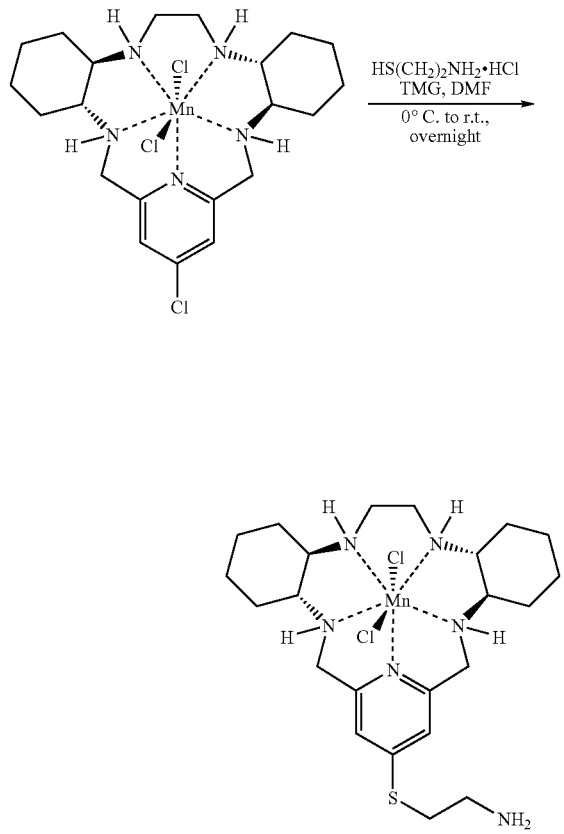

Example 9

This example illustrates the synthesis of amide conjugates of methoxy polyethylene glycol and compound of formula IX.

The compound of formula IX can be prepared as above and reacted with mPEG-SPA in the presence of N,N-diisopropylethylamine (DIPEA) and dimethyl formamide (DMF) at room temperature. The synthesis is as illustrated below.

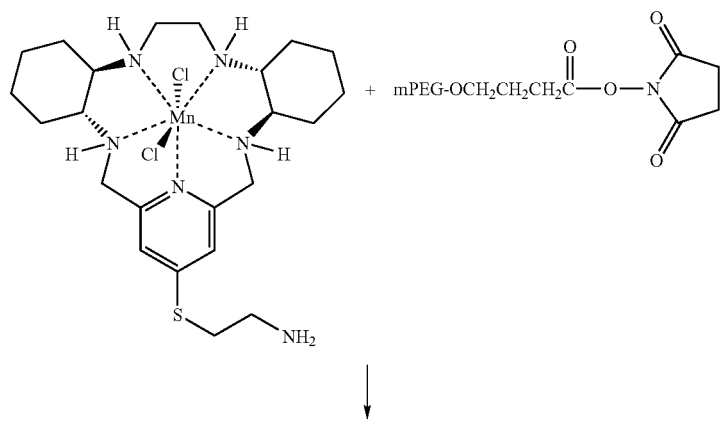

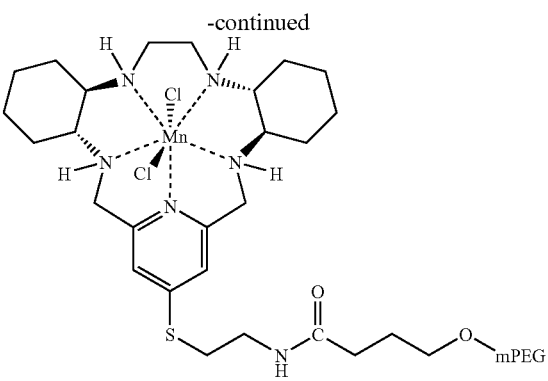

Example 10

This example illustrates the synthesis of urea conjugates of methoxy polyethylene glycol and compound of formula IX.

The compound of formula IX can be prepared as described above and reacted with mPEG-isocyanate in the presence of methylene chloride at room temperature. The synthesis is as illustrated below:

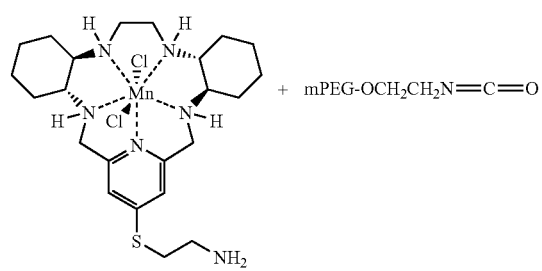

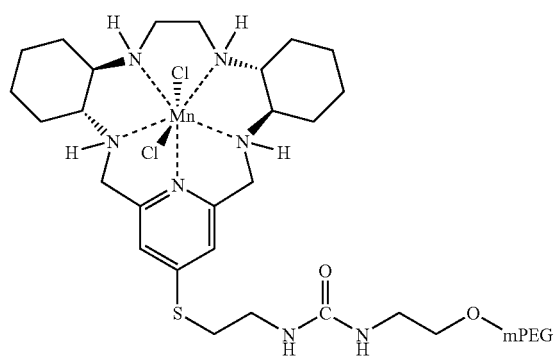

Example 11

This example illustrates the synthesis of conjugates in which each polyethylene glycol molecule reacts with two molecules of compound of formula VIo.

Thiol-PEG-Thiol (MW 3,115 Da, 0.997 g, 0.320 mmol) was weighed into a 100 mL 3-necked flask, flushed with $N_2$, and anhyd DMF (25 mL) was cannulated into it. The flask was cooled in an ice-bath and 1,1,3,3-tetramethylguanidine (0.088 mL, 0.700 mmol) was added with a pipette while magnetically stirring the suspension. The suspension turned lighter and was stirred for 45 min before the addition of M40409 (0.321 g, 0.620 mmol) in one portion. The cooling bath was removed and the pale yellow suspension was heated to 80° C. (ca 30 min). During this heating process, the reaction mixture became a light yellow solution, which was stirred at 80° C. for 40 h. The reaction mixture was allowed to cool to room temperature and added dropwise to a stirring solution of anhyd $Et_2O$ (400 mL). The white precipitate was collected by filtration and dried under high vacuum for 3 h. The off-white powder obtained was dissolved in $CH_2Cl_2$ (160 mL), washed with water (2×40 mL), and dried over $Na_2SO_4$. Removal of the solvent followed by drying overnight under high vacuum gave 1.08 g of a gummy solid. This was combined with the product (0.635 g) obtained from another identically run experiment with Thiol-PEG-Thiol (0.590 g, 0.189 mmol) and M40409 (0.190 g, 0.367 mmol) in DMF (20 mL) in the presence of 1,1,3,3-tetramethylguanidine (0.052 mL, 0.414 mmol), dissolved in $CH_2Cl_2$ (10 mL), and added dropwise into stirring anhyd $Et_2O$ (150 mL). The precipitate was collected by filtration and further triturated with $Et_2O$ (25 mL). Then if was dried under high vacuum (0.05 mmHg) to a constant weight to give M40509 (1.61 g, 77%) as an off-white powder; HPLC; major peaks at $t_R$=4.71 min (69.5%) and 5.03 min (20.1%); Loading: 66.4% based on 1.78% Mn analysed by ICP and MW of 3,041 Da for BTC-PEG-BTC; $k_{cat}$ (stopped flow)=$0.64\times10^7$ $M^{-1}s^{-1}$ (pH 8.1). For example:

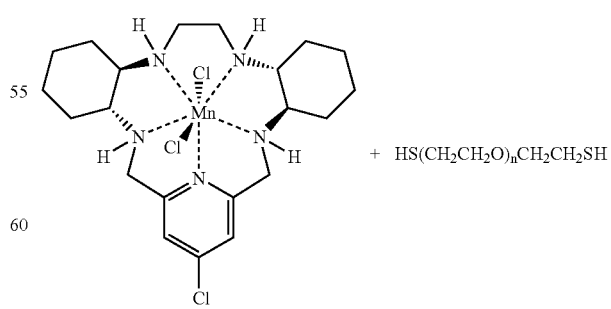

-continued

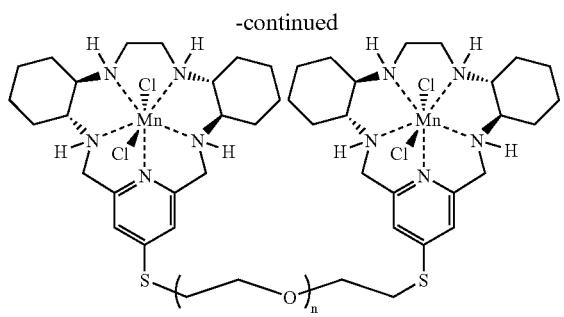

The number of polyethylene monomers, represented by n, in the polyethylene glycol can vary as described above. Compounds have been produced wherein the MW of the final compound is approximately 3.4 kDa.

Example 12

This example illustrates the synthesis of conjugates in which each polyethylene glycol molecule reacts with two molecules of compound of formula VIc. BTC-PEG-BTC (MW 3,041 Da, 2.05 g, 0.674 mmol) was weighed into a 100 mL 3-necked flask, flushed with Ar, and anhyd DMF (25 mL) was cannulated into it. The resulting colorless solution was cooled in an ice-bath and M40470 (0.748 g, 1.34 mmol) and DIPEA (0.279 mL, 1.60 mmol) ware added while magnetically stirring the contents. The pale yellow solution was slowly allowed to warm to r.t. and stirred for a total of 42 h. Then the reaction mixture was added slowly to a stirring solution of anhyd $Et_2O$ (400 mL), the precipitate was collected by titration and dried under high vacuum for 3 h. The precipitate was then dissolved in $CH_2Cl_2$ (200 mL), washed successively with 50 mL portions of water (×2), $NaHCO_3$, said $NaHCO_3$, water (×2), and brine. Then it was dried over $Na_2SO_4$ and the solvent was removed in vacuo. The resulting pale yellow viscous residue was dried overnight under vacuum to give 2.57 g of a pale yellow solid that still contained trace impurities of HOBt (HPLC analysis), it was once again dissolved in $CH_2Cl_2$ (200 mL) and successively washed with 50 mL portions of satd $NaHCO_3$-brine (4:1, v/v, ×5), 5% NaCl (×2), and brine (brine was incorporated into aq $NaHCO_3$ washings to aid quick partitioning of the layers). The $CH_2Cl_2$ layer was dried over $Na_2SO_4$, concentrated to about 10 mL in vacuo, and added slowly to vigorously stirring anhyd $Et_2O$ (150 mL). After stirring for 15 min, the precipitate was collected by filtration, lumpy material was broken up, and then triturated with anhyd $Et_2O$ (25 mL). Then it was dried under high vacuum (0.05 mmHg) to a constant weight to give M40596 (2.06 g, 78.9%) as an off-white powder: HPLC: major peaks at $t_R$=4.67 min (88.6%) and 4.96 min (8.9%); Loading: 76.4% based on 2.17% Mn analysed by ICP and MW of 3,115 Da for Thiol-PEG-Thiol; $k_{cat}$ (stopped flow) =$0.84\times10^1 s^{-1}$ (pH 8.1). For example:

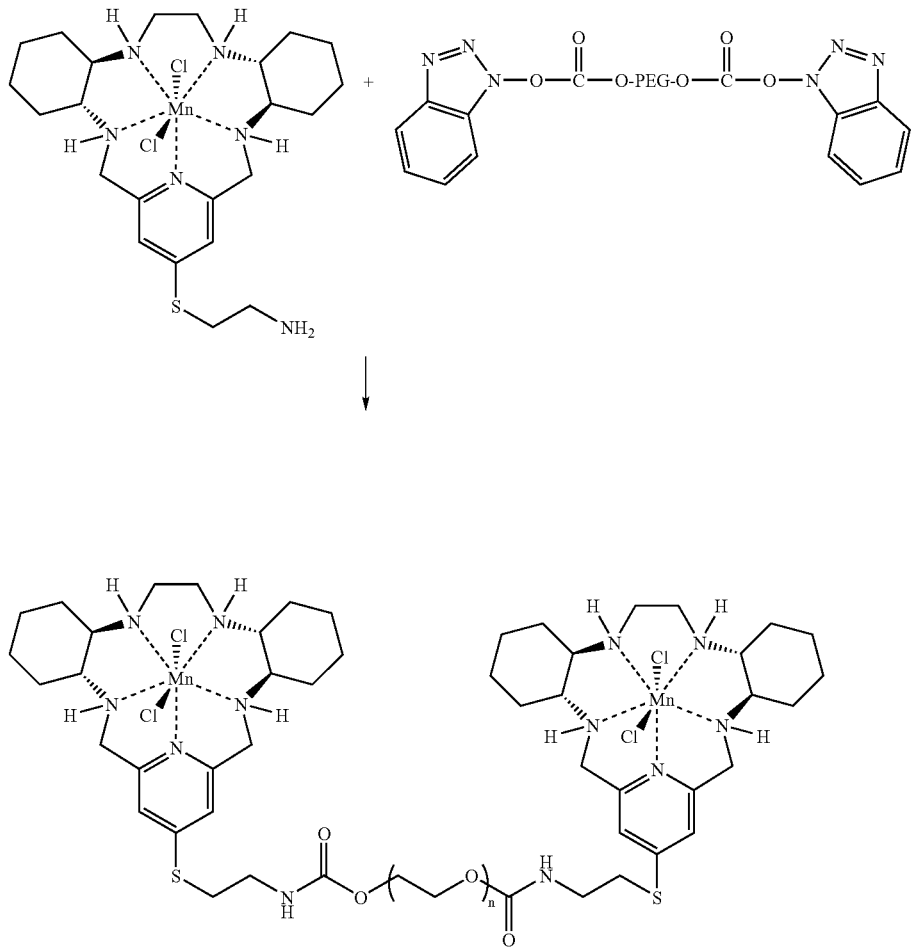

Compounds have been produced wherein the final product is approximately 3.4 kDa, but different molecular weight compounds are possible via modifying the length of the polyethylene glycol (i.e. changing n).

Example 13

This example illustrates the in vitro catalytic activity of PEGylated superoxide dismutase mimetic compounds of the present invention.

The stopped-flow kinetic analysis an cytochrome C assays were performed as follows.

Stopped-Flow Kinetic Analysis

Stopped-flow kinetic analysis has been utilized to determine whether a compound can catalyze the dismutation of superoxide (Riley, D. P., Rivers, W. J. and Weiss, R. H., "Stopped-Flow Kinetic Analysis for Monitoring Superoxide Decay in Aqueous Systems," Anal. Biochem, 196:344-349 1991). For the attainment of consistent and accurate measurements all reagents were biologically clean and metal-free. To achieve this, all buffers (Calbiochem) were biological grade, metal-free buffers and were handled with utensils which had been washed first with 0.1N HCl, followed by purified water, followed by a rinse in a $10^{-4}$ M EDTA bath at pH 8, followed by a rinse with purified water and dried at 65° C. for several hours. Dry DMSO solutions of potassium superoxide (Aldrich) were prepared under a dry, inert atmosphere of argon in a Vacuum Atmospheres dry glovebox using dried glassware. The DMSO solutions were prepared immediately before every stopped-flow experiment. A mortar and pestle were used to grind the yellow solid potassium superoxide (about 100 mg). The powder was then ground with a few drops of DMSO and the slurry transferred to a flask containing an additional 25 ml of DMSO. The resultant slurry was stirred for ½ h and then filtered. This procedure gave reproducibly about 2 mM concentrations of superoxide in DMSO. These solutions were transferred to a glovebag under nitrogen in sealed vials prior to loading the syringe under nitrogen, it should be noted that the DMSO/superoxide solutions are extremely sensitive to water, heat, air, and extraneous metals. A fresh, pure solution has a very slight yellowish tint.

Water for buffer solutions was delivered from an in-house deionized water system to a Barnstead Nanopure Ultrapure Series 550 water system and then double distilled, first from alkaline potassium permanganate and then from a dilute EDTA solution. For example, a solution containing 1.0 g of potassium permanganate, 2 liters of water and additional sodium hydroxide necessary to bring the pH to 9.0 were added to a 2-liter flask fitted with a solvent distillation head. This distillation will oxidize any trace of organic compounds in the water. The final distillation was carried out under nitrogen in a 2.5-liter flask containing 1500 ml of water from the first still and $1.0 \times 10^{-6}$ M EDTA. This step will remove remaining trace metals from the ultrapure water. To prevent EDTA mist from volatilizing over the reflux arm to the still head, the 40-cm vertical arm was packed with glass beads and wrapped with insulation. This system produces deoxygenated water that can be measured to have a conductivity of less than 2.0 nanoohms/$cm^2$.

The stopped-flow spectrometer system was designed and manufactured by Kinetic Instruments Inc. (Ann Arbor, Mich.) and was interfaced to a MAC IICX personal computer. The software for the stopped-flow analysis was provided by Kinetics Instrument Inc. and was written in QuickBasic with MacAdios drivers. Typical injector volumes (0.10 ml of buffer and 0.006 ml of DMSO) were calibrated so that a large excess of water over the DMSO solution were mixed together. The actual ratio was approximately 19/1 so that the initial concentration of superoxide in the aqueous solution was in the range 60-120 µM. Since the published extinction coefficient of superoxide in $H_2O$ at 245 nm is ~2250$M^{-1}$ $cm^{-1}$ (1), an initial absorbance value of approximately 0.3-0.5 would be expected for a 2-cm path length cell, and this was observed experimentally. Aqueous solutions to be mixed with the DMSO solution of superoxide were prepared using 80 mM concentrations of the Hepes buffer, pH 8.1 (free acid+Na form). One of the reservoir syringes was tilled with 5 ml of the DMSO solution while the other was filled with 5 ml of the aqueous buffer solution. The entire injection block, mixer, and spectrometer cell were immersed in a temperature controlled circulating water bath with a temperature of 21.0°±0.5°. Prior to initiating data collection for a superoxide decay, a baseline average was obtained by injecting several shots of the buffer and DMSO solutions into the mixing chamber. These shots were averaged and stored as the baseline. The first shots to be collected during a series of runs were with aqueous solutions that did not contain catalyst. This assures that each series of trials were free of contamination capable of generating first-order superoxide decay profiles. If the decays observed for several shots of the buffer solution were second-order, solutions of manganese(III) complexes could be utilized. In general, the potential SOD catalyst was screened over a wide range of concentrations. Since the initial concentration of superoxide upon mixing the DMSO with the aqueous buffer was about 1.2 times $10^{-4}$ M, we wanted to use a manganese (II) complex concentration that was at least 20 times less than the substrate superoxide. Consequently, we generally screened compounds for superoxide dissimulating activity using concentrations ranging from $5 \times 10^{-7}$ to $8 \times 10^{-6}$ M. Data acquired from the experiment was imported into a suitable math program (e.g., Cricket Graph) so that standard kinetic data analyses could be performed. Catalytic rate constants for dismutation of superoxide by manganese(ii) complexes were determined from linear plots of observed rate constants (kobs) versus the concentration of the manganese (II) complexes, kobs values were obtained from linear plots of in absorbance at 245 nm versus time for the dismutation of superoxide by the manganese(II) complexes.

Cytochrome C Assay

The Fe(II)cytochrome C assay procedure is known in the art (see for example, Fridovich I, Cytochrome C. In:*CRC Handbook of Methods for Oxygen Radical Research*. Boca Raton: CRC Press; pp 213-214 (1985). Briefly, the procedure used involved combining in a buffer, Fe(II)cytochrome C, xanthine and a test sample containing PEGylated superoxide dismutase mimetic. The solution is then incubated at about 25° C. for about 5 min. Xanthine oxidase is then added. Fe(III)cytochrome C has an absorbance at 550 nm and superoxide dismutase mimetic competes with Fe(III)cytochrome C for superoxide. Absorbance is, therefore, measured at 550 nm for about 15 min and the rate of change per min determined. The $IC_{50}$ amount of SOD in a sample solution can be determined as the amount that inhibits cytochrome C reduction by 50%.

The compounds tested were as follows. Compound XLIX having the following

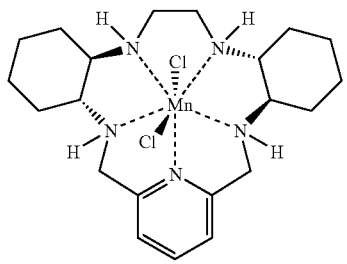

XLIX

Compound XLVIII having the following structure:

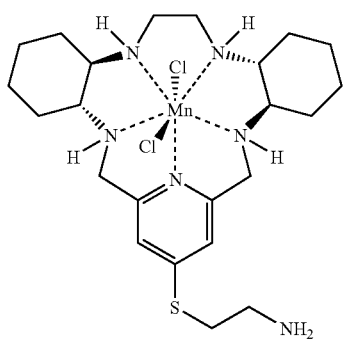

XLVIII and Compounds VIIa, VIIb, VIIc, and VIId having the structure below with polyethylene glycol molecular weights of 1 kDa (n=~23), 2 kDa (n=~45), 5 kDa (n=~114) and 20 kDa (n=~455), respectively:

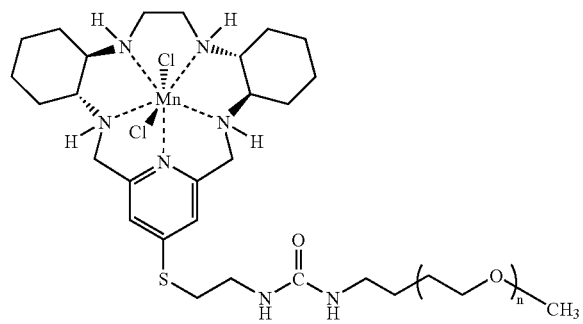

VII

The results of stopped-flow and cytochrome C assays were as shown in Table 15.

TABLE 15

| COMPOUND | MW (MALDI-TOF)[b] | Loading (%) based on Mn (ICP-MS) | Stopped-flow Assay kcat (M−1s−1) at pH = 8.1 | Cytochrome C Assay IC50 (µM) |
|---|---|---|---|---|
| XLIX | — | — | $1.19 \times 10^7$ | 0.31 [0.20-0.48][a] |
| XLVIII | — | — | $1.18 \times 10^7$ | 0.37 [0.27-0.51] |
| VIIa | 2,516 | 77.2 | $0.84 \times 10^7$ | 1.4 [0.47-4.2] |
| VIIb | 5,287 | 76.7 | $0.95 \times 10^7$ | 1.5 [0.95-2.3] |
| VIIc | 22,341 | 48.0 | $0.55 \times 10^7$ | 0.6 [0.32-1.1] |

[a] 95% confidence interval,
[b] observe as (M-Cl)+ ion

As shown in the table the PEGylated superoxide dismutase mimetic compounds were catalytically active although at lower levels of $k_{cat}$ in the stopped-flow assay and higher levels of $IC_{50}$ in the cytochrome C assay.

Example 14

This example illustrates the activity of the PEGylated superoxide dismutase mimetic compounds of the present invention in carageenan-induced hyperalgesia in rats.

Male Sprague-Dawley rats (175-200 g, Harlan Sprague Dawley, Indianapolis, Ind., USA) were housed and cared for in accordance with the guidelines of the institutional Animal Care and Use Committee and in accordance with NIH guidelines on laboratory animal welfare. Rats received a subplantar injection of carrageenan (0.1 ml of a 1% suspension in 0.85% saline) into the right hind paw. A hyperalgesic response to heat was determined in the animals by Hargreaves' method (Hargreaves et al, 1988). Rats were individually confined and acclimated to Plexiglas chambers for 30 min. A mobile unit consisting of a high intensity projector bulb was positioned to deliver a thermal stimulus directly to an individual hind paw from beneath the chamber. The withdrawal latency period of injected and contralateral paws was determined to the nearest 0.1 sec with an electronic clock circuit and thermocouple. If the animal failed to respond by 20 sec the test was terminated. Each point will represent the change in withdrawal latency compared with control measurements taken prior to carrageenan injection.

The intraplantar injection of carrageenan in rats resulted in a time-dependent increase in paw volume and hyperalgesia that was maximal after 3-6 h. The SOD mimetic, compound VIIa, was administered Intravenously 3 hours after carrageenan, at the time of maximal hyperalgesia. The compound was administered at doses of 5,29, 16.03 and 52.9 mg/kg which were equivalent to doses of compound XLIX of 1, 3 and 10 mg/kg, respectively. As shown in FIG. 1, compound VIIa inhibited the hyperalgesic response in a dose dependent manner with a very rapid onset of action and duration of at least 3 hours after administration.

Compound VIIa (5.3 mg/kg, i.v.) showed a modest inhibition of hyperalgesia as did morphine (0.1 mg/kg, s.c,). The combination of compound XVa (5.3 mg/kg, i.v.) and morphine (0.1 mg/kg. s.c.) acted synergistically to produce a substantial inhibition of hyperalgesia (FIG. 2).

Example 15

This example illustrates the increased plasma concentration and half life of PEGylated superoxide dismutase mimetic compounds VIIb, VIIc, VIId, and XIV compared the non-PEGylated superoxide dismutase mimetic.

FIG. 3 shows the plasma concentrations of PEGylated superoxide dismutase mimetic compounds following i.v. administration at doses equivalent to that of compound to their non-PEGylated counterpart, at 3 mg/kg. As can be seen in the figure, all of the PEGylated compounds produced higher equivalent plasma concentrations than that of compound non-PEGylated counterpart. Compound VIId with a polymer M. W. of about 20K produced substantially increased plasma concentrations with the plasma level being nearly ten fold greater than that of its non-PEGylated counterpart at 10 min after administration. The half life of compound was also substantially increased with plasma levels at 7 hours after administration being approximately equal to the peak plasma concentration of the non-PEGylated compound at 10 min as illustrated in Table 16:

TABLE 16

Half life wherein the $t_{1/2}$ is calculated as Vi/CL

| Compound | ~M.W. | Normalized AUC(0->6) (ng-hr/ml) | Vi (mL) | CL (mL/hr) | $T_{1/2}$ (minutes) |
|---|---|---|---|---|---|
| XLVIII | 500 | 333 | 211 | 752 | 11.7 |
| VIII | 2500 | 1431 | 87 | 177 | 20.6 |
| VIIc | 5000 | 1210 | 75 | 190 | 16.3 |
| VIId | 20000 | 14132 | 27 | 18 | 63.8 |

Example 16

This example describes a single dose toxicity study in mice, using the compound PEGylated and non-PEGylated versions of compound VIII.

The purpose of this study was to compare the potential acute toxicity of a compound when administered as a single bolus intravenous injection over one minute to mice.

Compound VIII was a white to off-white powder. The compound was prepared into dosing solutions for intravenous administration via the lateral tail vein. Ninety-six experimentally naive male mice, approximately 6 weeks old and weighing 27-38 grams at the outset of the study were assigned to treatment groups.

Animals were dosed once. Mortality and clinical observations were evaluated daily. Body weights were recorded prior to dose administration on Day 1 and prior to sacrifice on Day 5. All surviving animals were sacrificed on Day 5 and a gross necropsy was performed.

Animals were assigned to treatment groups as shown in Table 17:

TABLE 17

| Group | Dose Level (mg/kg/day) | Concentration (mg/ml) | Dose Volume (ml/kg) | Number of Males |
|---|---|---|---|---|
| 1. Control | 0 | 0 | 10.0 | 6 |
| Test Article (compound VIII) | | | | |
| 8. Low-dose | 156 | 15.6 | 10.0 | 6 |
| 9. Mid-dose | 520 | 52.0 | 10.0 | 6 |
| 10. High-dose | 1560 | 156.0 | 10.0 | 6 |

Results

There were no treatment-related body weight changes or gross necropsy findings. A total of 23 male mice died within a few minutes following dose administration on Day 1. Mortality did not occur in any of the control animals or in animals treated with compound VIII at a dose of 156, 520 or 1580 mg/kg.

The most frequently observed treatment-related clinical signs were decreased activity, a hunched posture and a ruffled hair coat. These clinical signs were observed in all test article-treated groups (except for control groups), and most animals exhibiting these clinical signs survived until the schedule day of euthanasia. Additionally, the presence of these clinical signs was most evident in groups treated with compound VIII (Groups 8, 9 and 10).

In conclusion, male CD-1 mice were administered compound VIII (156, 520 and 1560 mg/kg) as a single intravenous bolus administration over 1 minute. Clinical signs were observed in animals from all test article-treated groups. Body weights or weight gains were not affected by the administration of on any of the test articles. There were no apparent treatment-related gross necropsy findings.

The purpose of this study was to compare the potential acute toxicity of test compounds when administered as a single bolus intravenous injection over one minute to mice.

Animals were dosed once. Mortality and clinical observations were evaluated dally. Body weights were recorded prior to dose administration on Day 1 and prior to sacrifice on Day 5. All surviving animals were sacrificed on Day 5 and a gross necropsy was performed.

Dose Preparation

The protocol specified that test article formulations were to be prepared by serial dilution. Since the test articles were supplied in very limited quantifies, it was deemed necessary to modify the preparation procedure to minimize the use of test article for each study group. This protocol deviation had no negative impact on the integrity of the study.

Test article formulations were prepared by dilution from the highest concentration of each test article (the stock solution):

For each of test articles the highest dose concentration was prepared by weighing the test article into a tarred sterile vial and adding the appropriate calculated volume of TRIS-water buffer to provide the correct concentration of test article solution. The vial was then sealed with a rubber stopper and an aluminum crimp top, inverted several times and vortexed to ensure proper mixing of the contents.

Each of the lower dose concentrations of each test article was prepared by removing the appropriate calculated amount of stock solution from the sealed high dose vial using a syringe and needle. The amount removed was placed info a sterile vial. The appropriate calculated, amount of TRIS-water buffer required to achieve the desired final concentration of test article formulation was then added to the vial using a syringe and needle. The vial was then sealed using a rubber stopper and an aluminum crimp top.

For the test article, the highest dose concentration was prepared by weighing the test article into a tared beaker, due to the large amount of test article required for this formulation preparation. Most of the volume of TRIS-water buffer required for dissolving the lest article was added to the beaker, a stir bar was added, and the beaker was mixed on a stir plate. The resulting solution was transferred to a graduated cylinder, and sufficient buffer was added to achieve the final calculated volume. The solution was then transferred to a sterile vial which was sealed with a rubber stopper and an aluminum crimp top.

On the day of dosing (Day 1), 1-ml samples of each dosing solution, including the control article, were obtained to determine the concentration, and/or stability of the test article in vehicle. These samples were stored refrigerated (2-8° C.).

Husbandry

Housing: Animals, as described in Table 18 below, were housed group housed upon receipt and individually upon assignment to study in compliance with the National Research Council "Guide for the Care and Use of Laboratory Animals".

TABLE 18

| | |
|---|---|
| Species: | Mouse |
| Stock: | Hsd ICR (CD-1) |
| Total Number: | 6/group |
| Gender: | Male |
| Age Range: | 6 weeks at start of dosing; records of dates of birth for animals used in this study are retained in the Calvert archives. |
| Body Weight Range: | 27-38 grams at the outset (Day 1) of the study. |
| Animal Source: | Harlan Sprague Dawley P.O. Box 29176 Indianapolis, Indiana 46229 |
| Experimental History: | Purpose-bred and experimentally naïve at the outset of the study. |
| Identification: | Eartag and cage card |

The room in which the animals were kept is documented in the study records. No other species were kept in the same room.

Lighting: 12 hours light/12 hours dark

Room Temperature: 18 to 26° C.

Relative Humidity: 30-70%

Sanitation: Animal room and cage cleaning was performed.

Food: All animals had access to Harlan Teklad Rodent Diet (certified) or equivalent ad libitum, unless otherwise specified. The lot numbers) and specifications of each lot used were archived. No contaminants were known to be present in the certified diet at levels that would be expected to interfere with the results of this study. Analysis of the diet was limited to that performed by the manufacturer, records of which are maintained.

Water; Tap water was available ad libitum, to each animal via an automatic watering device. The water is routinely analyzed for contaminants. No contaminants were known to be present in the water at levels that would be expected to interfere with the results of this study. Results of the water analysis were maintained.

Acclimation: Study animals were acclimated to their housing for 5 days prior to the scheduled day of treatment.

Prestudy Health Screen and Selection Criteria

All animals received for this study were assessed as to their general health by a member of the veterinary staff or other authorized personnel. During the acclimation ported, each mouse was observed at least once daily for any abnormalities or for the development of infectious disease. Only animals that were determined by the study veterinarian and/or Study Director to be suitable for use were assigned to this study.

Assignment to Study Groups

Animals were assigned to study groups by a computerized randomization program (LABCAT) Randomization module version 2.48, developed by Innovative Program Associates, Inc. 303 Wall Street, Princeton, N.J. 08540-1515) designed to achieve similar group mean body weights.

Humane Care of Animals

Treatment of animals was in accordance with the study protocol which adhered to the regulations outlined in the USDA Animal Welfare Act (9 CFR Parts 1, 2 and 3) and the conditions specified in the Guide for the Care and Use of Laboratory Animals (ILAR publication, 1996, National Academy Press).

Test Compound Administration

TABLE 19

Group Assignments and Dose Levels

| Group | Dose Level (mg/kg/day) | Concentration (mg/ml) | Dose Volume (ml/kg) | Number of Males |
|---|---|---|---|---|
| 1. Control (vehicle) | 0 | 0 | 10.0 | 6 |
| Test Article #3: VIII | | | | |
| 8. Low-dose | 156 | 15.6 | 10.0 | 6 |
| 9. Mid-dose | 520 | 52.0 | 10.0 | 6 |
| 10. High-dose | 1560 | 156.0 | 10.0 | 6 |

Route: Intravenous slow bolus injection

Frequency: Once on Day 1.

Procedure: The vehicle control/test article formulations were administered once on Day 1 via the lateral tail vein, as a slow bolus injection over 1 minute, to male mice.

In-Life Observations and Measurements

Mortality:

Frequency: Twice daily (a.m. and p.m.); once daily (prior to sacrifice) on Day 5

Procedure; Each animal observed for evidence of death or impending death.

Clinical Observations:

Frequency: On the day of dosing, animals were observed predose and immediately post dose and 1, 2 and 4 hours post-dose. All clinical signs observed were recorded. On Days 2-5, animals were observed once dally.

Body Weight:

Frequency: Prior to dose administration on Day 1 and prior to sacrifice on Day 5

Terminal Procedures and Anatomic Pathology

Termination

Scheduled Sacrifice; All surviving animals were euthanized by $CO_2$ asphyxiation on Day 5.

Gross Necropsy

A complete gross necropsy was performed by trained personnel on all animals that were sacrificed or found dead during the study. The necropsy included examination of the external body surface, all orifices, and the cranial, thoracic and abdominal cavities and their contents. All abnormalities were described completely and recorded. One exception occurred from the above procedure. The necropsy for one animal (Mo. 553) treated with compound VIII at a dose 520 mg/kg was not documented at the time of euthanasia on Day 5.

Statistical Analysis

Data was evaluated using LABCAT Body Weight module version 4.65. This LABCAT module was developed by innovative Program Associates, Inc. (303 Wall Street, Princeton, N.J. 08540-1515). In addition, SYSTAT version 9.01, developed by SPSS, Inc., was used in body weight data analysis.

Body weight data were evaluated. The evaluation of the equality of means was made by a one-way analysis of variance using the F distribution to assess statistical significance, if statistically significant differences between the means were found. Dunnett's test was used to determine the degree of significance from the control means ($p<0.05$ and $p<0.01$).

Mortality

Mortality did not occur in any of the control animals (Group 1) and in animals treated with compound VII at a dose of 156, 520 or 1560 mg/kg (Groups 8, 9 and 10, respectively.

Clinical Observations

The most frequently observed treatment-related clinical signs were decreased activity, a hunched posture and a ruffled hair coat. These clinical signs were observed in all test article groups and most animals exhibiting these clinical signs survived until the schedule day of euthanasia. Additionally, the presence of these clinical signs was most evident in groups treated with compound VIII (Groups 8, 9 and 10), in which the number of animals and the frequency of occurrence of these clinical signs increased with each increment in dose level.

Body Weights

There were no noticeable differences in body weights or weight gains for test article-treated mice that survived until Day 5, when compared to the body weights or weight gains of control male mice.

Gross Necropsy Findings

There were no apparent treatment-related gross necropsy findings in any of the test article-treated animals or vehicle control animals.

Conclusion

In conclusion, male CD-1 mice were administered compound VIII (156, 520 and 1560 mg/kg) as a single intravenous bolus administration over 1 minute. Clinical signs were observed in animals from all test article-treated groups. Body weights or weight gains were not affected by the administration of on any of the test articles. There were no apparent treatment-related gross necropsy findings.

Example 17

An experiment was be performed wherein rats were injected with PEGylated and non-PEGylated superoxide dismutase mimetic compounds. Animal health, death rates, and necroscopy findings were compared between the two groups:

TEST ARTICLE INFORMATION: Test Article 1: Compound XLVIII and Test Article 2: Compound VIII.

TEST SYSTEM: Species: Rat; Strain: Crl:CD® (SD): Source: Charles River Laboratories. Raleigh, N.C.

Number of Animals:

Forty-five males and 45 females were ordered and 40 animals of each sex were assigned to the study. Females were nulliparous and non-pregnant. Animals not assigned to study were deemed part of the stock rat colony or euthanized by $CO_2$ inhalation and discarded.

Approximate Age and Weight:

Animals were approximately 5 to 7 weeks of age when received, and approximately 7 to 9 weeks of age at initiation of dosing. Body weight was approximately 150-320 grams at initiation of dosing.

Identification System:

Each rat were uniquely Identified by a metal ear tag displaying the animal number. Individual cage cards were be affixed to each cage and will display the animal number, group number, study number, dosage level and sex of the animal.

Justification for Selection and Numbers of Animals;

This species and strain of animal is recognized as appropriate for single dose toxicity studies. The Sprague-Dawley rat was be utilized because it is a widely used strain for which significant historical control data are available. The number of animals selected for this study was the minimum required to achieve the object of the study.

Specific Maintenance Schedule:

Animal Housing:

The animals were individually housed in clean suspended wire-mesh cages in an environmentally controlled room during the study. The cages were elevated above cage-board or other suitable material, which were changed at least three times each week. The cages were subjected to routine cleaning at a frequency consistent with maintaining good animal health.

Environmental Conditions:

An average daily temperature of $71\pm5°$ F. ($22\pm3C$) and an average daily relative humidify of $50\pm20\%$ was maintained. Temperature and relative humidity were monitored continuously. Fluorescent lighting controlled by light timers provided illumination for a 12-hour light/dark photoperiod. The ventilation rate was set at a minimum of 10 room air changes per hour, 100% fresh air.

Drinking Water:

Reverse osmosis-purified water was available ad libitum. The municipal water supplying the laboratory is analyzed on a routine basis to assure that contaminants are not present in concentrations that would be expected to affect the outcome of the study.

Basal Diet:

PMI Nutrition international, LLC Certified Rodent LabDiet® 5002 (meal) were offered ad libitum. Each lot utilized was identified and recorded. Standard operating procedures provide specifications for acceptable levels of heavy metals and pesticides that are reasonably expected to be present in the diet without interfering with the purpose or conduct of the study. Each lot of feed has been analyzed to assure specifications were met.

Experimental Design:

Animal Receipt and Quarantine:

Each animal was inspected by a qualified technician upon receipt. Animals Judged to be in good health were acclimated for a minimum of seven days. All animals were weighed and assigned a permanent animal number. During the acclimation period, each animal were observed twice daily for changes in general appearance or behavior. The animals were allowed a pretreatment week (included in acclimation period) during which body weights, food consumption and general health were monitored. All animals received a detailed physical examination approximately one week prior to initiation of dosing and at the time of animal selection for randomization.

Randomization:

Near the end of the pretest period, animals judged to be suitable for testing were assigned to the study at random based on body weight stratification info a block design using a computer program. A printout containing the animal numbers and individual group assignments were generated. Animals were then be arranged into the groups according to the printout. Body weights at randomization were within $\pm20\%$ of the mean for each group.

Route and Rationale of Test Article Administration:

The route of administration was by intravenous injection via a tail vein. The intravenous route was selected to assess potential systemic toxicity of maximal bioavailability.

Organization of Test Groups, Dosage Levels and Treatment Regimen:

Organization of Test Groups;

The following table presents the study group arrangement (shown in Table 19):

TABLE 19

Dosing schedule for the animals is shown herein.

| Group Number | Treatment | Dosage Level (mg/kg) | Concentration (mg/mL) | Dosage Volume (mL/Kg) | Number of Animals Males | Females |
|---|---|---|---|---|---|---|
| 1 | Compound XLVIII | 3 | 0.6 | 5 | 5 | 5 |
| 2 | Compound XLVIII | 10 | 6 | 5 | 5 | 5 |
| 3 | Compound XLVIII | 6 | 2 | 5 | 5 | 5 |
| 4 | Control | 0 | 0 | 5 | 5 | 5 |
| 5 | Compound VIII | 100 | 20 | 5 | 5 | 5 |
| 6 | Compound VIII | 300 | 60 | 5 | 5 | 5 |
| 7 | Compound VIII | 1000 | 200 | 5 | 5 | 5 |
| 8 | Compound VIII | 3000 | 200 | 15 | 5 | 5 |

Vehicle:

26 mM sodium bicarbonate buffer solution (prepared by dissolving 0.437 grams of anhydrous $NaHCO_3$ per 200 mL of sterile saline).

Treatment Regimen:

The test article and vehicle were administered once after which the animals entered a 3-day observation period. For Groups 1-7, animals were appropriately restrained, and administered test article solutions by bolus intravenous injection (sterile needle and syringe) via a lateral tail vein. A constant dosage volume (5.0 ml/kg) was used for Group 1-7. The dosage volume for Group 8 was 15 mL/kg. For Group 8, the dosing solution was administered over an approximately 5-minute period using a Razel® syringe pump. The site, of injection was marked to facilitate identification at necropsy.

Adjustment of Dosages: individual doses were based on the Day 0 body weight.

Method and Frequency of Formulations: Aseptic techniques was used for all preparation procedures. A 26 mM sodium bicarbonate buffer solution was prepared as the vehicle by dissolving 0.437 grams of $NaHCO_3$ in 200 ml of sterile physiologic saline. The resultant pH was approximately 8.1 to 8.3. The appropriate amounts of test article was dissolved in the vehicle to provide the concentrations detailed in Section 7.4.1. Fresh test article solutions was prepared on the day of dosing. The pH of the dosing solution was measured before initiation of dosing.

All dosing solutions was filtered prior to dose administration using a Durapore® 0.22-μm polyvinylidine fluoride (PVDF) filter or equivalent.

Concentration Analysis:

Samples of appropriate size (approximately 1.0 mL) of the dosing solutions was collected at the time of preparation. Samples were frozen and stored at approximately −70° C. and saved for possible future concentration analysis. If analysis is not performed the frozen samples were discarded following issuance of the final report.

Parameters to be Evaluated (All Groups):

Viability Observations; All animals were observed for mortality/morbidity twice daily, once in the morning and once in the afternoon. Moribund animals were euthanized by $CO_2$ inhalation.

Daily Observations: A clinical examination was performed for all animals within 2 hours prior to dosing on the day of dosing, immediately following dosing, at approximately 1 and 3 hours after dosing and once daily at approximately the same time each day thereafter. Observations included, but are not limited to, changes in the skin, fur, eyes and mucous membranes; respiratory, circulatory, autonomic and central nervous systems functions; somatomotor activity and behavior patterns. Findings noted at the clinical examination were recorded for individual animals; the condition of animals without signs were documented in a general comment at each observation period.

Detailed Physical Examinations; A detailed physical examination was conducted at least once during the pretreatment period, at randomization and on the day of the scheduled necropsy. Animals without signs were noted individually.

Unscheduled Observations: A separate computer protocol was used to collect any findings outside the above-specified observations. Only the presence of findings was recorded; the absence of findings was not be recorded.

Individual Body Weights: Individual body weights were recorded during acclimation, at pretest initiation, at randomization, on Day 0, daily after dosing and on the day of scheduled euthanasia.

Individual Food Consumption: Individual food consumption was recorded weekly during acclimation on all animals and daily after dosing.

Macroscopic Examination: A gross necropsy was conducted on all animals dying spontaneously, euthanized in extremis or at the scheduled primary necropsy. Animals euthanized in extremis or at study termination were anesthetized by $CO_2$ inhalation and exsanguinated. Gross lesions and injection sites were saved in neutral buffered formalin. Necropsy included examination of the external surface, all orifices and the cranial, thoracic, abdominal and pelvic cavities including viscera.

Statistical Methods:

All analyses were two-failed for significance levels of 5% and 1%. The body weight and food consumption data was evaluated for rats dosed with the test article by identifying dose and/or time-related changes. Body weights, body weight changes and food consumption for selected groups was compared by Dunnett's test (Dunnett Biometrics, 20:482-491, 1984). Group 2 was compared to Group 5, Group 3 was compared to Group 6, Group 4 was compared to Group 7 and Group 4 was compared to Group 5. Body weights, body weight changes and food consumption for selected groups was compared by Dunnett's test (Dunnett, 1984).

Reports:

The final report contained a summary, test article data, methods and procedures, animal data (i.e., mortality, clinical observations, body weights, etc.) and an interpretation and discussion of the study results. The final report was comprehensive and shall define level(s) inducing toxic effects under the condition of the investigation.

TABLE 20

Mortality of animals per treatment group

| Group Number | Treatment | Dosage Level (mg/kg) | Concentration (mg/mL) | Dosage Volume (mL/Kg) | Number of Animals Dying during experiment | |
|---|---|---|---|---|---|---|
| | | | | | Males | Females |
| 1 | Compound XLVIII | 3 | 0.6 | 5 | 0/5 | 0/5 |
| 2 | Compound XLVIII | 10 | 6 | 5 | 2/5 | 2/5 |
| 3 | Compound XLVIII | 6 | 2 | 5 | 0/5 | 0/5 |
| 4 | Control | 0 | 0 | 5 | 0/5 | 0/5 |
| 5 | Compound VIII | 100 | 20 | 5 | 0/5 | 0/5 |
| 6 | Compound VIII | 300 | 60 | 5 | 0/5 | 0/5 |
| 7 | Compound VIII | 1000 | 200 | 5 | 0/5 | 0/5 |
| 8 | Compound VIII | 3000 | 200 | 15 | 4/5 | 3/5 |

In the male groups, on animal in each of groups 2 and 3 had convulsions immediately after dosing. In addition, in group 3, all animals had hypoactivity, and two had twitching. In group 2, three animals also had decreased respiration, four had labored respiration and one was gasping. In group 8 one animal had increased respiration, and three had clear discharge from the left eye, and four from the right eye. All other animals had no clinical findings immediately after injection for these clinical symptoms.

In the female group if was noted that there was one prostrate animal in group 2, three animals with impaired equilibrium in group 3, one animal twitching in each of groups 2 and 3. One animal in group 3 also showed intermittent convulsions and three showed labored respiration. In group 8 females one animal showed hypoactivity immediately post-dose, one showed impaired equilibrium, one showed partial closure of the right eye, and one the left eye. In addition in group 8 two females showed increased respiration, two showed labored respiration, and one was gasping. All other animals showed no clinical findings for these clinical symptoms.

No significant changes in body weight were seen in any female in any group in the test, while the males in groups seven and eight showed statistically decreased weight.

Conclusion

As can be seen in the table above, the PEGylated compound VIII is much less toxic than a non-PEGylated counterpart (Compound XLVIII). These data indicate an $LD_{100}$ of the PEGylated compound is on the order of 100 times less lethal than the non-PEGylated compound.

Example 18

Toxicity Study in Humans

The following clinical study could be carried out in order to evaluate the safety and tolerability of purified, PEGylated superoxide dismutase mimetic(s). The mimetic(s) would be administered to subjects with or without central or peripheral pain, and/or inflammation in order to evaluate the safety of PEGylated superoxide dismutase mimetics in humans. In the rat and mousse studies described above the inventors show that PEGylated superoxide dismutase mimetics are safer and less toxic than their non-PEGylated counterparts. This study is a prophetic example describing how a test of the toxicity of PEGylated superoxide dismutase mimetic(s) could be carried out in humans, this example shows how a efficacy test of PEGylated superoxide dismutase mimetic mimetics could be carried, out in human subjects.

The compounds of the present invention may be formulated by known methods for administration to a subject using several routes which include, but are not limited to, parenteral, oral, topical, intradermal, intramuscular, intraperitoneal, intravenous, subcutaneous, intranasal, epidural, and ophthalmic routes. The individual compounds may also be administered in combination with one or more additional compounds of the present invention and/or together with other biologically active or biologically inert agents. Such biologically active or inert agents may be in fluid or mechanical communication with the compound(s) or attached to the compound(s) by Ionic, covalent, Van der Waals, hydrophobic, hydrophilic or other physical forces. Administration may be localized in a subject, but administration may also be systemic.

The primary objective of the study would be to evaluate the safety and tolerability of PEGylated superoxide dismutase mimetic mimetics compared to placebo, in human subjects. Purified, PEGylated superoxide dismutase mimetic could be prepared in a manner similar to the above (Dose Preparation as in Table 18). The PEGylated superoxide dismutase mimetic used herein is not limited and could include any PEGylated superoxide dismutase mimetic including but not limited to PEGylated forms of compounds discussed herein.

The containers containing the PEGylated superoxide dismutase mimetics would be supplied to the study center with each container labeled according to the contents of the container. The Pharmacist/Study Nurse, who prepared the injection, would also maintain the investigational product at the required temperature. The study blind would be maintained by the Pharmacist/Study Nurse.

Placebo vehicle for the study would be supplied in similar or identical containers. The study could be a single center, randomized, double blind, placebo controlled, dose ranging Phase 1 study of three dose levels similar to Table 18 above, or lowered or increased by, for example, about 2, 3, 4, 5, 6, 7, 8, 9, 10, 20, 30, 40, 50, 60 70, 80, 90, or 100 fold. The doses of the purified PEGylated superoxide dismutase mimetic used in this trial would be well below doses known to be toxic to animals. The study would be designed, for example, to include sixteen evaluation subjects. Up to three-fourths would be treated with the compounds above.

Patients would be treated randomly and in double-blind fashion in, for example, four treatment cohorts. Each cohort having a progressively longer interval of administration of study compound, and/or increased dosage of the study compound.

Each subject would have at least 3 study visits: a Screening Day, the Treatment Day, and a Post-Treatment Day. Alternatively the patients would be hospitalized during the entire course of treatment and recovery On the Treatment Day the subject would be randomized, and pre-treatment evaluation performed. This study might include a full physical, for example. Pain scores, blood pressure, and full evaluations would be ongoing during administration. On the Post-Treatment Day, study evaluation would be performed to determine if there were any effects from the administration of the compound.

A determination would be made as to whether purified, PEGylated superoxide dismutase mimetic mimetics are well tolerated and at what dose levels. It is expected based on the animal studies above that a subset PEGylated superoxide dismutase mimetic mimetics will be well tolerated in human subjects.

Example 19

Efficacy Study in Humans

The following prophetic clinical study would evaluate the efficacy of PEGylated superoxide dismutase mimetic mimetics for treatment of central or peripheral pain, and/or inflammation.

The primary objective of the study would be to evaluate the efficacy of PEGylated superoxide dismutase mimetic mimetics compared to placebo, in subjects with central or peripheral pain, and/or inflammation. The experiment could be used to determine a therapeutically effective dosage. The compounds of the present invention may be formulated by known methods for administration to a subject using several routes which include, but are not limited to, parenteral, oral, topical, intradermal, intramuscular, intraperitoneal, intravenous, subcutaneous, intranasal, epidural, and ophthalmic routes. The individual compounds may also be administered in combination with one or more additional compounds of the present invention and/or together with other biologically active or biologically inert agents. Such biologically active or inert agents may be in fluid or mechanical communication with the compounds) or attached to the compound(s) by ionic, covalent, Van der Waste, hydrophobic, hydrophilic or other physical forces. Administration may be localized in a subject, but administration may also be systemic.

Double blind controls and the study itself would be designed as above. Dosing would be well below the toxicity level determined in animal studies.

The study would be designed to include at least twelve evaluation subjects (patients suffering a defined pain: >40 mm on VAS, for example). Six (6) subjects would be treated with PEGylated superoxide dismutase mimetic mimetics end 6 subjects will be treated with placebo vehicle. Patients would be treated randomly and in double-blind fashion. Each subject would have, for example, 3 study visits: a Screening Day, the Treatment Day, and a Post-Treatment Day. On the Treatment Day the subject is randomized, pre-treatment evaluation is performed. The patient is brought into the procedure room, and a VAS pain score is taken (0 mm-no pain, 100 mm-extreme pain). Prior to treatment patient would mark the level of their pain on a 100 mm, non-hatched VAS scale. At 20 minute intervals thereafter they were asked to give a verbal categorical rating of their pain as "a lot better", "a little better", "much the same", "a little worse" or "much worse" and to mark the level of pain on a VAS scale of the same type as used previously. It would be pre-defined that patients with VAS pain scores of 30 mm or less would be categorized as having mild pain, those with scores of 70 mm or more were categorized as having severe pain and those from 31 mm to 69 mm, moderate pain. The minimal clinically significant difference (MCSD) in VAS pain score would be defined as the mean difference between current and preceding scores when the subject reported "a little worse" or "a little better" pain.

Once the patient marks his or her pain on the card, he/she is propped for administration. Once the patient is propped the patient could receive a PEGylated superoxide dismutase mimetic by any appropriate means, for example. The PEGylated superoxide dismutase mimetic used herein is not limited and could include any PEGylated superoxide dismutase mimetic including but not limited to PEGylated forms of compounds discussed herein.

VAS pain scores as well as verbal reports would be taken immediately following administration and for a period afterwards, as well as prior. On the Post-Treatment Day, a study evaluation would be performed Changes in pain scores would also be measured at three weeks following administration. It is expected that PEGylated superoxide dismutase mimetic mimetics will be efficacious in the treatment of diseases that have a superoxide component, including but not limited to central and peripheral pain and inflammation.

Other Embodiments

The detailed description set-forth above is provided to aid those skilled in the art in practicing the present invention. However, the invention described and claimed herein is not to be limited in scope by the specific embodiments herein disclosed because these embodiments are intended as illustration of several aspects of the invention. Any equivalent embodiments are intended to be within the scope of this invention, indeed, various modifications of the invention in addition to those shown and described herein will become apparent to those skilled in the art from the foregoing description which do not depart from the spirit or scope of the present inventive discovery. Such modifications are also intended to fail within the scope of the appended claims.

REFERENCES CITED

All publications, patents, patent applications and other references cited in this application are incorporated herein by reference in their entirety for ail purposes to the same extent as if each individual publication, patent, patent application or other reference was specifically and individually indicated to be incorporated by reference in its entirety for all purposes. Citation of a reference herein shall not be construed as an admission that such is prior art to the present invention.

What is claimed is:

1. A compound comprising
a superoxide dismutase mimetic linked to at least one polyethylene glycol,
wherein
   at least one of said polyethylene glycol comprises seven or more ethylene glycol monomers; and
   the superoxide dismutase mimetic is a pentaaza macrocycle having a formula of $G_A$-$G_B$-$G_C$ wherein (a) $G_A$ has a structure according to formula I:

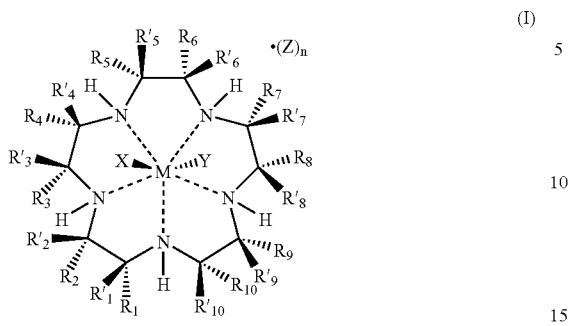

(I)

which comprises:
(i) one or more of $R_1$, $R'_1$, $R_2$, $R'_2$, $R_3$, $R'_3$, $R_4$, $R'_4$, $R_5$, $R'_5$, $R_6$, $R'_6$, $R_7$, $R'_7$, $R_8$, $R'_8$, $R_9$, $R'_9$, $R_{10}$, and $R'_{10}$ are independently:
  ($i^a$) hydrogen; or
  ($i^b$) a bond; or
  ($i^c$) a moiety independently selected from the group consisting of alkenyl, alkenylcycloalkenyl, alkenylcycloalkyl, alkyl, alkylcycloalkenyl, alkylcycloalkyl, alkynyl, aralkyl, aryl, cycloalkenyl, cycloalkyl, cycloalkylalkyl, cycloalkylcycloalkyl, cycloalkenylalkyl, and heterocyclyl; or
  ($i^d$) a moiety independently selected from the group consisting of $-OR_{11}$, $-NR_{11}R_{12}$, $-COR_{11}$, $-CO_2R_{11}$, $-CONR_{11}R_{12}$, $-SR_{11}$, $-SOR_{11}$, $-SO_2R_{11}$, $-SO_2NR_{11}R_{12}$, $-N(OR_{11})(R_{12})$, $-P(O)(OR_{11})(OR_{12})$, $-P(O)(OR_{11})(R_{12})$, $-OP(O)(OR_{11})(OR_{12})$, $R_{11}NC(O)R_{12}$, $R_{11}NC(O)R_{12}$ and substituents attached to the α-carbon of α-amino acids, wherein $R_{11}$ and $R_{12}$ are independently hydrogen or alkyl; or
(ii) one or more of $R_1$ or $R'_1$ and $R_2$ or $R'_2$, $R_3$ or $R'_3$ and $R_4$ or $R'_4$, $R_5$ or $R'_5$ and $R_6$ or $R'_6$, $R_7$ or $R'_7$ and $R_8$ or $R'_8$, and $R_9$ or $R'_9$ and $R_{10}$ or $R'_{10}$ together with the carbon atoms to which they are attached independently form a cycle or heterocycle which
  ($ii^a$) is substituted or unsubstituted;
  ($ii^b$) saturated, partially saturated or unsaturated; and
  ($ii^c$) comprise 3 to 20 carbon atoms; and any of $R_1$, $R'_1$, $R_2$, $R'_2$, $R_3$, $R'_3$, $R_4$, $R'_4$, $R_5$, $R'_5$, $R_6$, $R'_6$, $R_7$, $R'_7$, $R_8$, $R'_8$, $R_9$, $R'_9$, $R_{10}$, and $R'_{10}$ not forming said cycle or heterocycle is defined as above; or
(iii) one or more of $R_1$ and $R'_1$, $R_2$ and $R'_2$, $R_3$ and $R'_3$, $R_4$ and $R'_4$, $R_5$ and $R'_5$, $R_6$ and $R'_6$, $R_7$ and $R'_7$, $R_8$ and $R'_8$, $R_9$ and $R'_9$, and $R_{10}$ and $R'_{10}$, together with the carbon atom to which they are attached independently form a cycle or heterocycle which
  ($iii^a$) is substituted or unsubstituted;
  ($iii^b$) saturated, partially saturated or unsaturated; and
  ($iii^c$) comprise 3 to 20 carbon atoms; and any of $R_1$, $R'_1$, $R_2$, $R'_2$, $R_3$, $R'_3$, $R_4$, $R'_4$, $R_5$, $R'_5$, $R_6$, $R'_6$, $R_7$, $R'_7$, $R_8$, $R'_8$, $R_9$, $R'_9$, $R_{10}$, and $R'_{10}$ not forming said cycle or heterocycle is defined as above; or
(iv) one or more of $R_{10}$ or $R'_{10}$ and $R_1$ or $R'_1$, $R_2$ or $R'_2$ and $R_3$ or $R'_3$, $R_4$ or $R'_4$ and $R_5$ or $R'_5$, $R_6$ or $R'_6$ and $R_7$ or $R'_7$, or $R_8$ or $R'_8$ and $R_9$ or $R'_9$ together with the carbon atoms to which they are attached independently form a nitrogen-containing heterocycle which
  ($iv^a$) is substituted or unsubstituted;
  ($iv^b$) is saturated, partially saturated or unsaturated, in which case the hydrogen attached to the nitrogen which is both part of the unsaturated heterocycle and the pentaaza macrocycle and the R groups attached to the carbon atoms which are both part of the heterocycle and the macrocycle are absent; and
  ($iv^c$) comprises 3 to 20 carbon atoms; and any of $R_1$, $R'_1$, $R_2$, $R'_2$, $R_3$, $R'_3$, $R_4$, $R'_4$, $R_5$, $R'_5$, $R_6$, $R'_6$, $R_7$, $R'_7$, $R_8$, $R'_8$, $R_9$, $R'_9$, $R_{10}$, and $R'_{10}$ not forming said heterocycle are defined as above; or
(v) one or more of $R_1$, $R'_1$, $R_2$, $R'_2$, $R_3$, $R'_3$, $R_4$, $R'_4$, $R_5$, $R'_5$, $R_6$, $R'_6$, $R_7$, $R'_7$, $R_8$, $R'_8$, $R_9$, $R'_9$, $R_{10}$, and $R'_{10}$, together with a different one of $R_1$, $R'_1$, $R_2$, $R'_2$, $R_3$, $R'_3$, $R_4$, $R'_4$, $R_5$, $R'_5$, $R_6$, $R'_6$, $R_7$, $R'_7$, $R_8$, $R'_8$, $R_9$, $R'_9$, $R_{10}$, and $R'_{10}$, which is attached to an atom in the pentaaza macrocycle is bound by a strap to form a cycle or heterocycle, said strap represented by the formula:

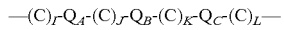

wherein
C is saturated, partially saturated or unsaturated;
I, J, K and L are independently integers from 0 to 10;
$Q_A$, $Q_B$ and $Q_C$ are independently selected from the group consisting of alkenyl, alkenylcycloalkenyl, alkenylcycloalkyl, alkyl, alkylcycloalkenyl, alkylcycloalkyl, alkynyl, aralkyl, aryl, cycloalkenyl, cycloalkyl, cycloalkylalkyl, cycloalkylcycloalkyl, cycloalkenylalkyl, and heterocyclyl, wherein said heterocyclyl is unsubstituted or substituted with aza, amide, ammonium, oxa, this, sulfonyl, sulfinyl, sulfonamide, phosphoryl, phosphinyl, phosphino, phosphonium, keto, ester, alcohol, carbamate, urea, thiocarbonyl, borates, boranes, boraza, silyl, siloxy, silaza, halogens and any combination thereof; and
any of $R_1$, $R'_1$, $R_2$, $R'_2$, $R_3$, $R'_3$, $R_4$, $R'_4$, $R_5$, $R'_5$, $R_6$, $R'_6$, $R_7$, $R'_7$, $R_8$, $R'_8$, $R_9$, $R'_9$, $R_{10}$, and $R'_{10}$ not forming said cycle or heterocycle are defined as above; or
(vi) combinations of any of (i) through (v) above; and wherein
M is a transition metal;
X, Y and Z are independently selected from the group consisting of halide, oxo, aquo, hydroxo, alcohol, phenol, dioxygen, peroxo, hydroperoxo, alkylperoxo, arylperoxo, ammonia, alkylamino, arylamino, heterocycloalkyl amino, heterocycloaryl amino, amine oxides, hydrazine, alkyl hydrazine, aryl hydrazine, nitric oxide, cyanide, cyanate, thiocyanate, isocyanate, isothiocyanate, alkyl nitrile, aryl nitrile, alkyl isonitrile, aryl isonitrile, nitrate, nitrite, azido, alkyl sulfonic acid, aryl sulfonic acid, alkyl sulfoxide, aryl sulfoxide, alkyl aryl sulfoxide, alkyl sulfenic acid, aryl sulfenic acid, alkyl sulfinic acid, aryl sulfinic acid, alkyl thiol carboxylic acid, aryl thiol carboxylic acid, alkyl thiol thiocarboxylic acid, aryl thiol thiocarboxylic acid, alkyl carboxylic acid, aryl carboxylic acid, urea, alkyl urea, aryl urea, alkyl aryl urea, thiourea, alkyl thiourea, aryl thiourea, alkyl aryl thiourea, sulfate, sulfite, bisulfate, bisulfite, thiosulfate, thiosulfite, hydrosulfite, alkyl phosphine, aryl phosphine, alkyl phosphine oxide, aryl phosphine oxide, alkyl aryl phosphine oxide, alkyl phosphine sulfide, aryl phosphine sulfide, alkyl aryl phosphine sulfide, alkyl phosphonic acid, aryl phosphonic acid, alkyl phosphinic acid, aryl phosphinic acid, alkyl phosphinous acid, aryl phosphinous acid, phosphate, thiophosphate, phosphite, pyrophosphite, triphosphate, hydrogen phosphate, dihydrogen phosphate, alkyl guanidino, aryl guanidino, alkyl aryl guanidino, alkyl carbamate, aryl carbamate, alkyl aryl carbamate, alkyl thiocarbamate, aryl thiocarbamate, alkylaryl thiocarbamate, alkyl dithiocarbamate, aryl dithiocarbamate, alkylaryl dithiocarbamate, bicarbonate, carbonate, perchlorate, chlorate, chlorite, hypochlorite, perbromate, bromate, bromite, hypobromite, tetrahalomanganate, tetrafluoroborate, hexafluoroantimonate, hypophosphite, iodate, periodate, metaborate, tetraaryl borate, tetra alkyl borate, tartrate, salicylate, succinate, citrate, ascorbate, saccharinate, amino acid, hydroxamic acid, thiotosylate, and anions of ion exchange resins, or the corresponding anions thereof; or X, Y and Z are independently selected from the group consisting of charge—neutralizing anions which are derived from any monodentate or polydentate coordinating ligand and a ligand system and the corresponding anion thereof; or X, Y and Z are independently attached to one or more of $R_1$, $R'_1$, $R_2$, $R'_2$, $R_3$, $R'_3$, $R_4$, $R'_4$, $R_5$, $R'_5$, $R_6$, $R'_6$, $R_7$, $R'_7$, $R_8$, $R'_8$, $R_9$, $R'_9$, $R_{10}$, and $R'_{10}$; and n is an integer from 0 to 3; and at least one of said bond of ($i^b$), said moiety of ($i^c$), said moiety of ($i^d$), said cycle or heterocycle of (ii), said cycle or heterocycle of (iii), said heterocycle of (iv) or said cycle or heterocycle of (v) independently forms a link from $G_A$ to $G_B$; and (b) $G_B$ is a bond or a linking moiety, wherein said linking moiety comprises an atom selected from the group consisting of S, O, N, P, C and any combination thereof; and (c) $G_C$ is a moiety having formula —$(OCH_2CH_2)_f$—$R_{13}$, —$(CH_2CH_2O)_f$—$R_{13}$, or –$CH_3O$—$(CH_2CH_2O)_f$—$R_{13}$, or combinations thereof, wherein f is an integer from 7 to about 1,000 and $R_{13}$ is a bond or is selected from the group consisting of H, alkenyl, alkenylcycloalkenyl, alkenylcycloalkyl, alkyl, alkylcycloalkenyl, alkylcycloalkyl, alkynyl, aralkyl, aryl, cycloalkenyl, cycloalkyl, cycloalkylalkyl, cycloalkylcycloalkyl, cycloalkenylalkyl, heterocyclyl, —$OR_{11}$, —$NR_{11}R_{12}$, —$COR_{11}$, —$CO_2R_{11}$, —$CONR_{11}R_{12}$, —$SR_{11}$, —$SOR_{11}$, —$SO_2R_{11}$, —$SO_2NR_{11}R_{12}$, —$N(OR_{11})(R_{12})$, —$P(O)(OR_{11})(OR_{12})$, —$P(O)(OR_{11})(R_{12})$, —$OP(O)(OR_{11})(OR_{12})$, $R_{14}$—$(CH_2)_g$—H, $(CH_2)_g$—H, $G_A$, $(CH_2)_g$—$R_{14}$-$G_A$, and O—C—ONH$(CH_2)_g$—$R_{14}$-$G_A$, wherein $G_A$, $R_{11}$ and $R_{12}$ are as defined above, g is an integer from 0 to about 500, and $R_{14}$ is selected from the group consisting of S, N, O, P, and C.

2. A compound according to claim 1, wherein $G_A$ is of Formula II:

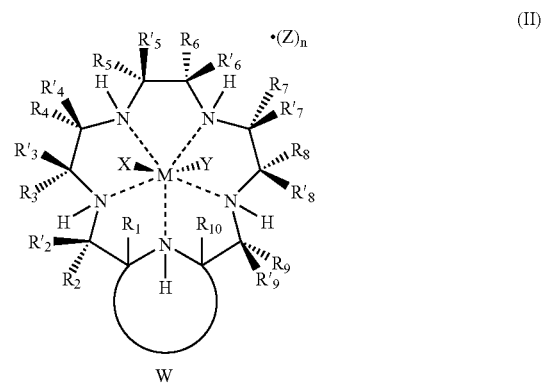

wherein a nitrogen of the pentaaza macrocycle and two adjacent carbon atoms to which the nitrogen is attached independently form a nitrogen—containing heterocycle W which (a) is substituted or unsubstituted;

(b) is saturated, partially saturated or unsaturated, in which case the hydrogen attached to the nitrogen which is both part of the unsaturated heterocycle and the pentaaza macrocycle and the R groups attached to the carbon atoms which are both part of the heterocycle and the macrocycle are absent; and (c) comprises 2 to 20 carbon atoms.

3. A compound according to claim 2, wherein one or more of $R_1$, $R_2$, $R'_2$, $R_3$, $R'_3$, $R_4$, $R'_4$, $R_5$, $R'_5$, $R_6$, $R'_6$, $R_7$, $R'_7$, $R_8$, $R'_8$, $R_9$, $R'_9$, and $R_{10}$ together with an atom of the heterocycle W are independently bound by a strap to form a cycle or heterocycle, said strap represented by the formula:

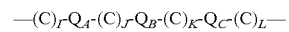

wherein

C is saturated, partially saturated or unsaturated;

I, J, K and L are independently integers from 0 to 10; and $Q_A$, $Q_B$ and $Q_C$ are independently selected from the group consisting of alkenyl, alkenylcycloalkenyl, alkenylcycloalkyl, alkyl, alkylcycloalkenyl, alkylcycloalkyl, alkynyl, aralkyl, aryl, cycloalkenyl, cycloalkyl, cycloalkylalkyl, cycloalkylcycloalkyl, cycloalkenylalkyl, and heterocyclyl, wherein said heterocyclyl is unsubstituted or substituted with aza, amide, ammonium, oxa, this, sulfonyl, sulfinyl, sulfonamide, phosphoryl, phosphinyl, phosphino, phosphonium, keto, ester, alcohol, carbamate, urea, thiocarbonyl, borates, boranes, boraza, silyl, siloxy, silaza, halogens and any combination thereof.

4. A compound according to claim 2, wherein $G_A$ is of Formula III:

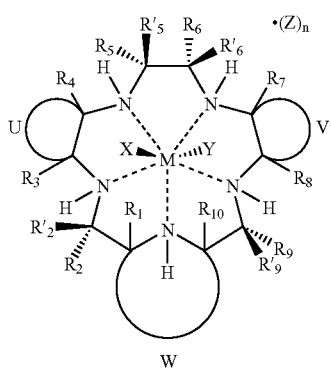

(III)

wherein two sets of two adjacent carbon atoms of the macrocycle independently form cycles or heterocycles U and V which
(a) are substituted or unsubstituted,
(b) are saturated, partially saturated or unsaturated, and
(c) comprise 3 to 20 carbon atoms.

5. A compound according to claim 4, wherein one or more of $R_1$, $R_2$, $R'_2$, $R_3$, $R_4$, $R_5$, $R'_5$, $R_6$, $R'_6$, $R_7$, $R_8$, $R_9$, $R'_9$, and $R_{10}$ together with an atom of the heterocycle W, cycle or heterocycle U, and cycle or heterocycle V are independently bound by a strap to form a cycle or heterocycle, said strap represented by the formula:

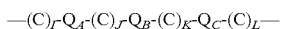

wherein

C is saturated, partially saturated or unsaturated;

I, J, K and L are independently integers from 0 to 10; and $Q_A$, $Q_B$ and $Q_C$ are independently selected from the group consisting of alkenyl, alkenylcycloalkenyl, alkenylcycloalkyl, alkyl, alkylcycloalkenyl, alkylcycloalkyl, alkynyl, aralkyl, aryl, cycloalkenyl, cycloalkyl, cycloalkylalkyl, cycloalkylcycloalkyl, cycloalkenylalkyl, and heterocyclyl, wherein said heterocyclyl is unsubstituted or substituted with aza, amide, ammonium, oxa, this, sulfonyl, sulfinyl, sulfonamide, phosphoryl, phosphinyl, phosphino, phosphonium, keto, ester, alcohol, carbamate, urea, thiocarbonyl, borates, boranes, boraza, silyl, siloxy, silaza, halogens and any combination thereof.

6. A compound according to claim 1, wherein $G_B$ is a linking moiety having a formula selected from the group consisting of:

—O—CO—NH—, —NH—,
—O—CO—CH$_2$—CH$_2$—CO—NH—,
—O—CH$_2$—CO—NH—NH—CO—,

-continued

—O—CO—O—, 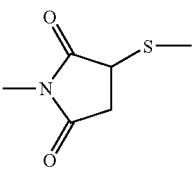,

—S—S—, —S—,

—S—CH$_2$—CH$_2$—NH—CO—O—,

—S—CH$_2$—CH$_2$—,

—O—CO—NH—CH$_2$—CH$_2$S—,

—S—CH$_2$—CH$_2$—NH—CO—CH$_2$—CH$_2$—,

—S—CH$_2$—CH$_2$—NH—CH$_2$—CH$_2$—CH$_2$—CH$_2$—,

—CO—NH—, 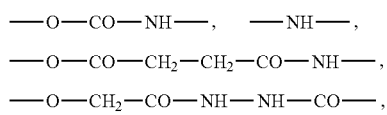

—O—,

—O—CO—CH$_2$—CH$_2$—CH$_2$—CO—NH—,

—O—CH$_2$—CH(OH)—CH$_2$—O—,

—NH—CO—O—, —SO$_2$—CH$_2$—CH$_2$—S—,

—NH—CO—CH$_2$—S—, —CH$_2$—CH$_2$—S—,

—CO—NH—CH$_2$—CH$_2$—S—,

—S—CH$_2$—CH$_2$—NH—CO—,

—S—CH$_2$—CH$_2$NH—CO—NH—CH$_2$—CH$_2$—,

—S—CH$_2$—CH$_2$—NH—CO—CH$_2$—CH$_2$—CH$_2$—O—, and

—S—CH$_2$—CH$_2$—NH—CO.

7. A compound according to claim 1, wherein M is Mn.

8. A compound according to claim 2, wherein M is Mn.

9. A compound according to claim 4, wherein M is Mn.

10. A compound according to claim 1, wherein M is selected from the group consisting of Fe, Ni, Cu and V.

11. A compound according to claim 2, wherein M is selected from the group consisting of Fe, Ni, Cu and V.

12. A compound according to claim 4, wherein M is selected from the group consisting of Fe, Ni, Cu and V.

13. A compound of claim 1, wherein $G_B$ is a moiety independently selected from the group consisting of —OR$_{11}$, —NR$_{11}$R$_{12}$, —COR$_{11}$, —CO$_2$R$_{11}$, —CONR$_{11}$R$_{12}$, —SR$_{11}$, —SOR$_{11}$, —SO$_2$R$_{11}$, —SO$_2$NR$_{11}$R$_{12}$, —N(OR$_{11}$)(R$_{12}$), —P(O)(OR$_{11}$)(OR$_{12}$), —P(O)(OR$_{11}$)(R$_{12}$), —OP(O)(OR$_{11}$)(OR$_{12}$), $R_{11}$ NC(O)R$_{12}$, $R_{11}$ NC(O)R$_{12}$ and substituents attached to the α-carbon of α-amino acids, wherein $R_{11}$ and $R_{12}$ are independently hydrogen or alkyl.

14. A compound according to claim 1, having a formula selected from the group consisting of IVa, IVb, IVc, IVd, IVe, IVf, IVg, and IVh:

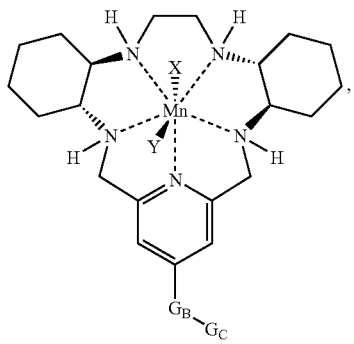
(IVa)

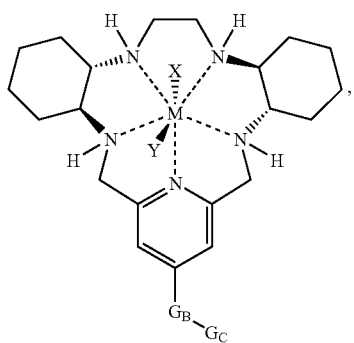
(IVb)

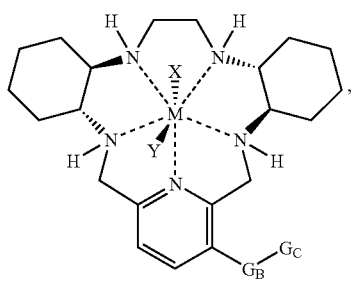
(IVc)

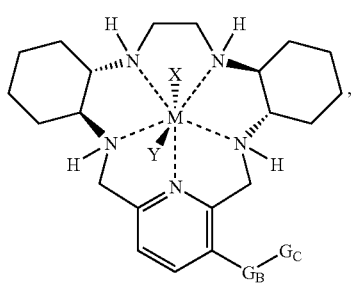
(IVd)

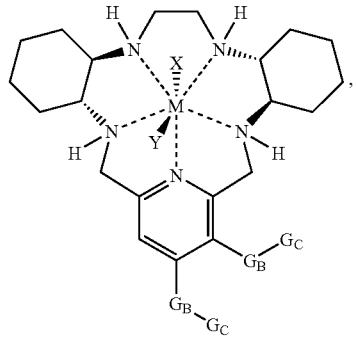
(IVe)

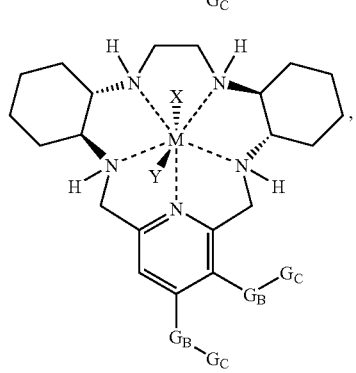
(IVf)

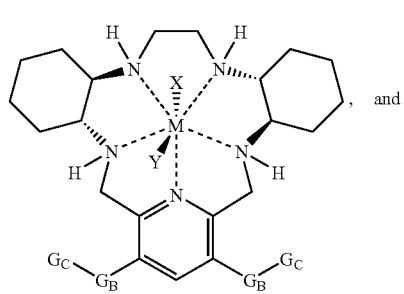
(IVg) and

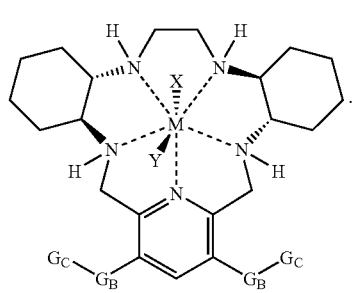
(IVh)

15. A compound according to claim 14, wherein $G_C$ of IVa, IVb, IVc, and IVd comprises from 7 to about 1,000 ethylene glycol monomers.

16. A compound according to claim 14, wherein $G_C$ of IVa, IVb, IVc, and IVd comprises from about 10 to about 500 ethylene glycol monomers.

17. A compound according to claim 14, wherein $G_C$ of IVa, IVb, IVc, and IVd comprises from about 15 to about 250 ethylene glycol monomers.

18. A compound according to claim 14, wherein $G_C$ of IVa, IVb, IVc, and IVd comprises from about 20 to about 100 ethylene glycol monomers.

19. A compound according to claim 14, wherein $G_C$ of IVa, IVb, IVc, and IVd comprises from about 25 to about 50 ethylene glycol monomers.

20. A compound according to claim 14, wherein each $G_C$ of IVe, IVf, IVg, and IVh independently comprises from 7 to about 1,000 ethylene glycol monomers.

21. A compound according to claim 14, wherein each $G_C$ of IVe, IVf, IVg, and IVh independently comprises from about 10 to about 500 ethylene glycol monomers.

22. A compound according to claim 14, wherein each $G_C$ of IVe, IVf, IVg, and IVh independently comprises from about 15 to about 250 ethylene glycol monomers.

23. A compound according to claim 14, wherein each $G_C$ of IVe, IVf, IVg, and IVh independently comprises from about 20 to about 100 ethylene glycol monomers.

24. A compound according to claim 14, wherein each $G_C$ of IVe, IVf, IVg, and IVh independently comprises from about 25 to about 50 ethylene glycol monomers.

25. A compound according to claim 14, wherein M is Mn.

26. A compound according to claim 14, wherein M is selected from the group consisting of Fe, Ni, Cu and V.

27. A compound according to claim 1, wherein $G_A$ is a pentaaza macrocycle having a formula selected from the group consisting of Va, Vb, Vc and Vd:

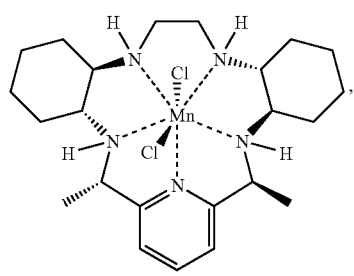
(Va)

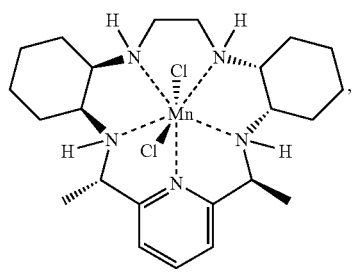
(Vb)

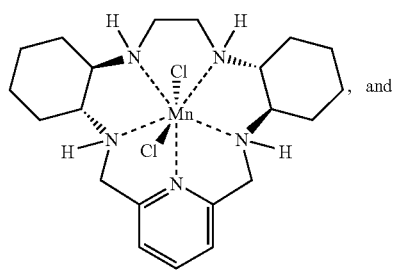
(Vc), and

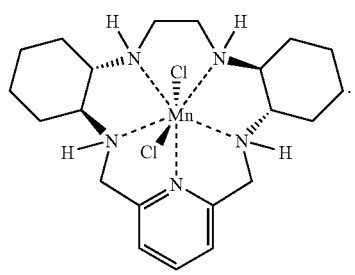
(Vd).

28. A compound according to claim 1, selected from the group consisting of:

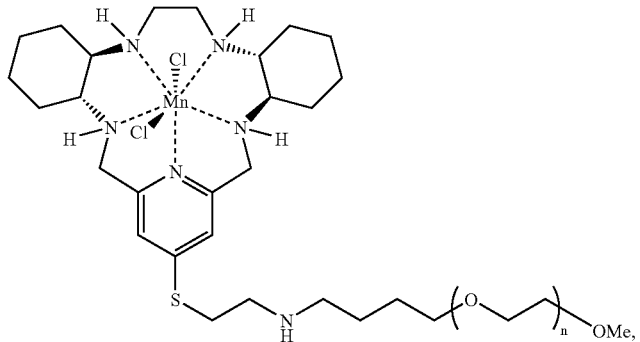

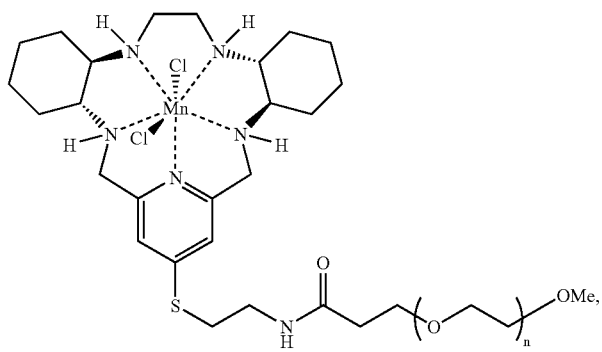

123
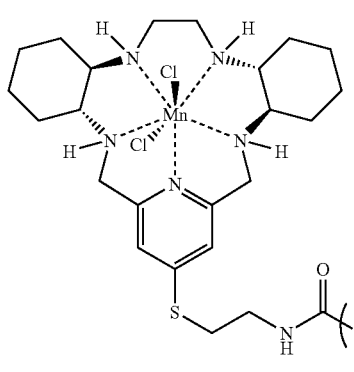
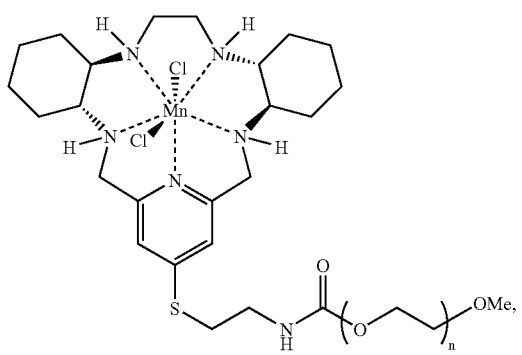
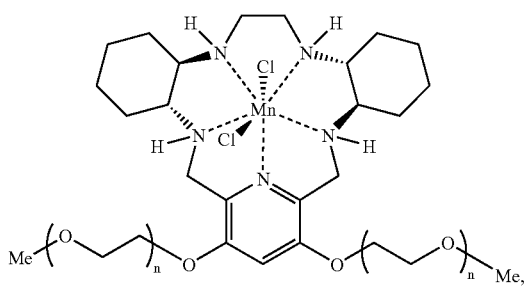
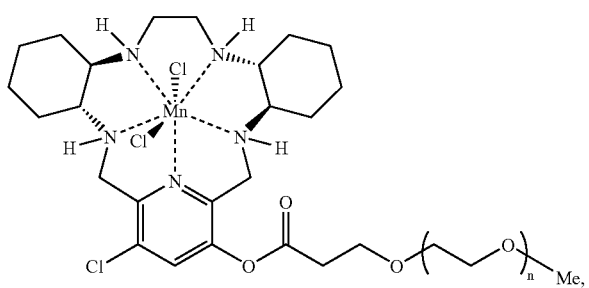
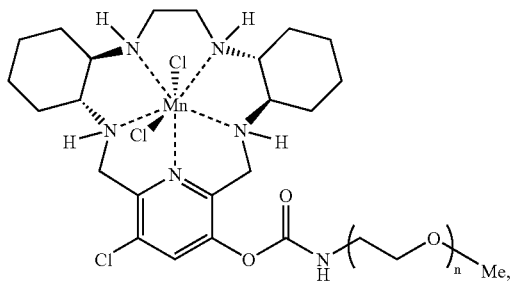
124
-continued
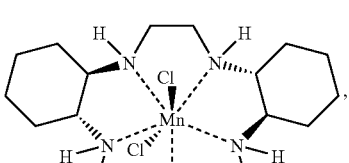
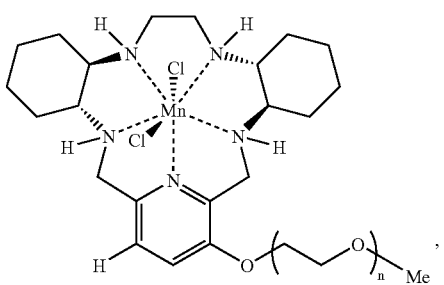
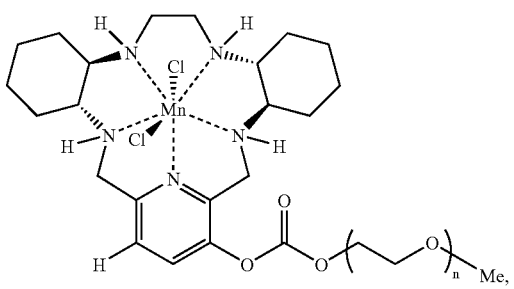
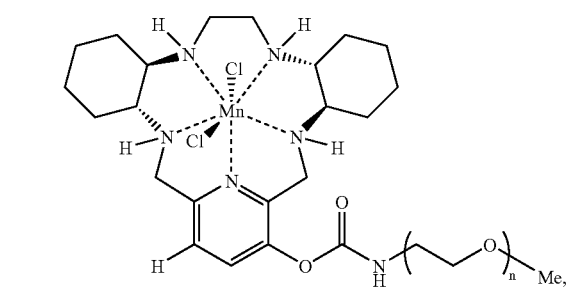
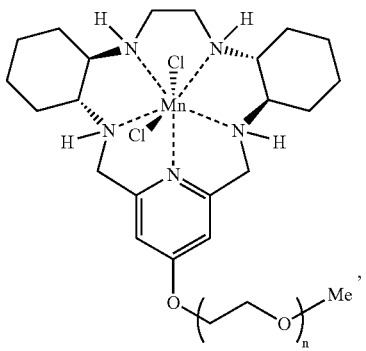

125 126
-continued
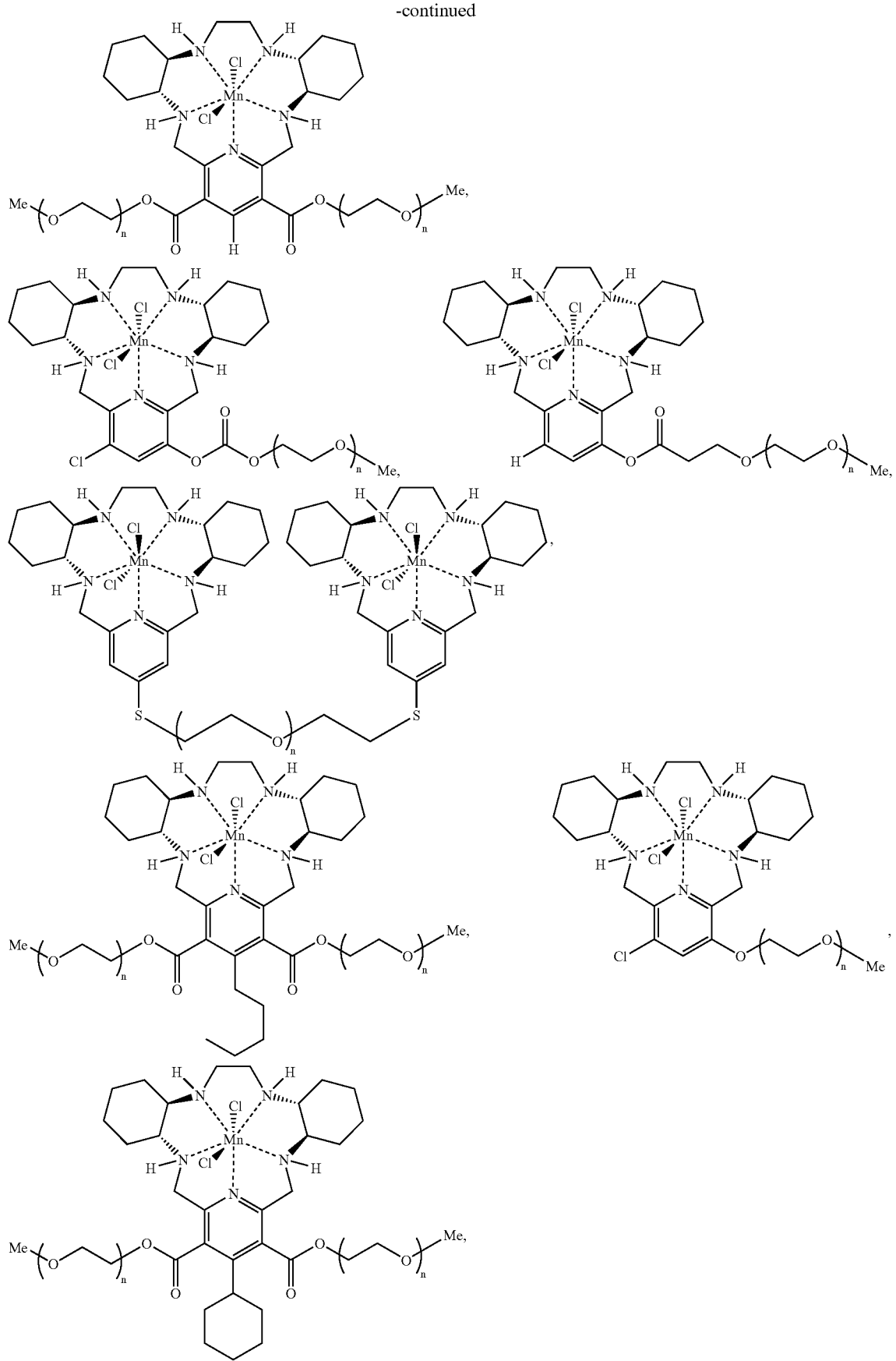

-continued
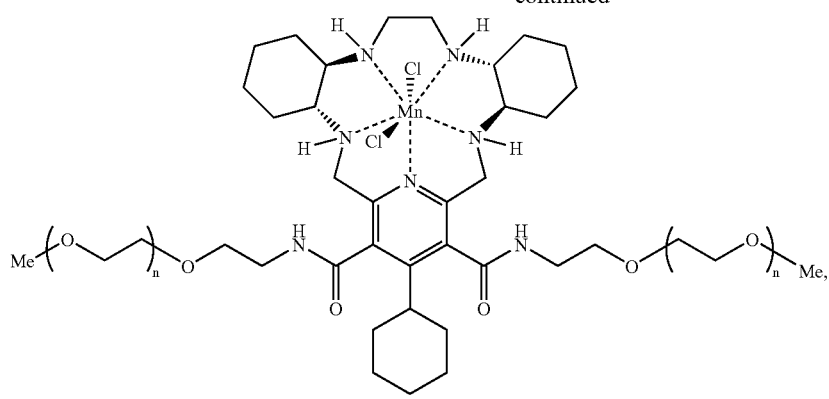
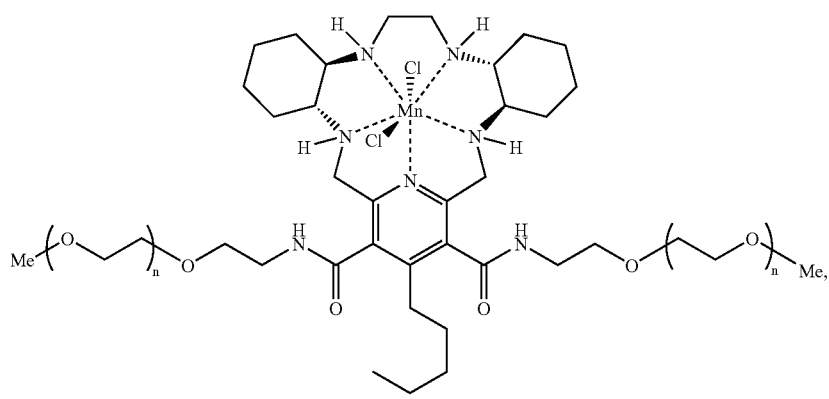
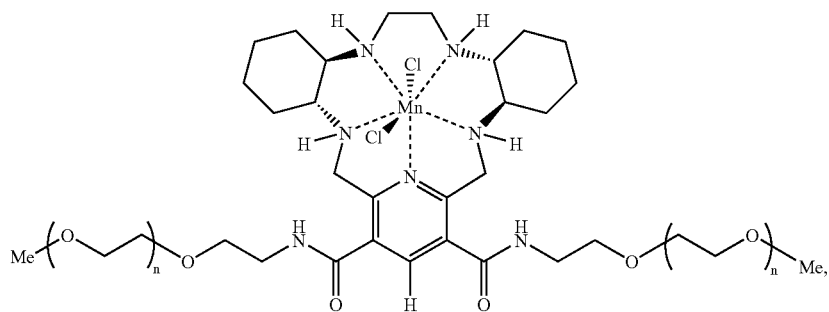
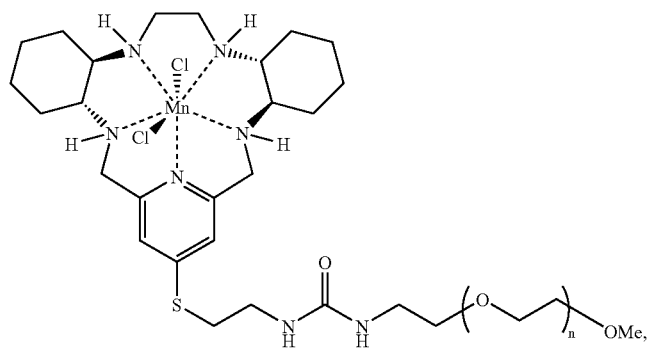

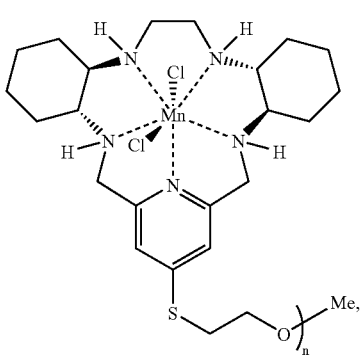

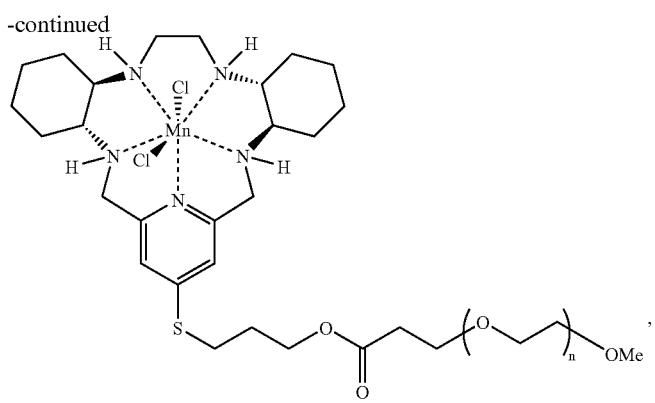

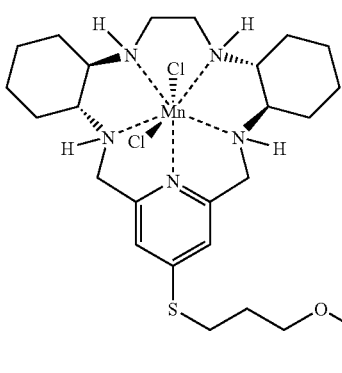

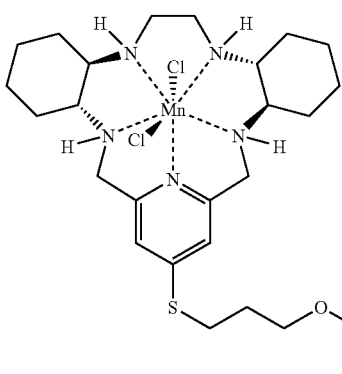

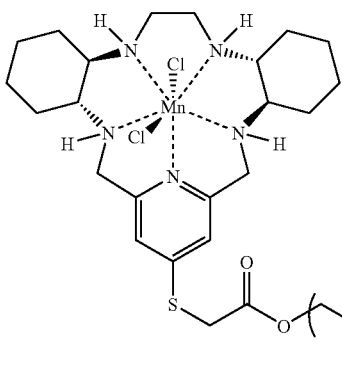

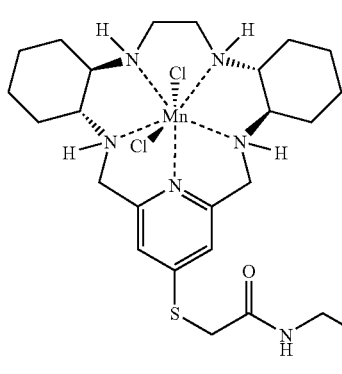

wherein n is an integer from about 7 to about 1,000.

29. A compound according to claim 28, wherein n is an integer from about 10 to about 500.

30. A compound according to claim 28, wherein n is an integer from about 15 to about 250.

31. A compound according to claim 28, wherein n is an integer from about 20 to about 100.

32. A compound according to claim 28, wherein n is an integer from about 25 to about 50.

33. A compound according to claim 28, wherein n is about 23.

34. A compound according to claim 28, wherein n is about 45.

35. A compound according to claim 28, wherein n is about 114.

36. A compound according to claim 28, wherein n is about 455.

37. A compound according to claim 28, wherein the polyethylene glycol has a molecular weight from about 200 Da to about 44 kDa.

38. A compound according to claim 28, wherein the polyethylene glycol has a molecular weight from about 2500 Da to about 40 kDa.

39. A compound according to claim 28, wherein the polyethylene glycol has a molecular weight from about 1 kDa to about 35 kDa.

40. A compound according to claim 28, wherein the polyethylene glycol has a molecular weight from about 5 kDa to about 25 kDa.

41. A compound according to claim 28, wherein the polyethylene glycol has a molecular weight from about 800 Da to about 1200 Da.

42. A compound according to claim 28, wherein the polyethylene glycol has a molecular weight from about 1800 Da to about 2200 Da.

43. A compound according to claim 28, wherein the polyethylene glycol has a molecular weight from about 4800 Da to about 5200 Da.

44. A compound according to claim 28, wherein the polyethylene glycol has a molecular weight from about 9800 Da to about 10,200 Da.

45. A compound according to claim 28, wherein the polyethylene glycol has a molecular weight from about 1900 Da to about 2100 Da.

46. A compound according to claim 1, having a formula:

[chemical structure]

wherein N is between about 7 and 1,000.

47. A compound according to claim 46, wherein n is about 23.

48. A compound according to claim 46, wherein n is about 45.

49. A compound according to claim 46, wherein n is about 114.

50. A compound according to claim 46, wherein n is about 455.

51. A compound according to claim 46, wherein the polyethylene glycol has a molecular weight from about 300 Da to about 44 kDa.

52. A compound according to claim 46, wherein the polyethylene glycol has a molecular weight from about 2500 Da to about 40 kDa.

53. A compound according to claim 46, wherein the polyethylene glycol has a molecular weight from about 1 kDa to about 35 kDa.

54. A compound according to claim 46, wherein the polyethylene glycol has a molecular weight from about 5 kDa to about 25 kDa.

55. A compound according to claim 46, wherein the polyethylene glycol has a molecular weight from about 800 Da to about 1200 Da.

56. A compound according to claim 46, wherein the polyethylene glycol has a molecular weight from about 1800 Da to about 2200 Da.

57. A compound according to claim 46, wherein the polyethylene glycol has a molecular weight from about 4800 Da to about 5200 Da.

58. A compound according to claim 46, wherein the polyethylene glycol has a molecular weight from about 9800 Da to about 10,200 Da.

59. A compound according to claim 46, wherein the polyethylene glycol has a molecular weight from about 1800 to about 2200 Da.

60. A compound according to claim 1, having a formula:

[chemical structure with OMe and subscript 45]

61. A compound according to claim 1, having a formula:

$$G_A\text{-}(G_B\text{-}G_C)_h$$

comprising one A moiety having a plurality of $G_B$-$G_C$ moieties attached thereto, wherein $G_A$, $G_B$ and $G_C$ are independently as defined above, and h is an integer from 1 to about 1,000.

62. A compound according to claim 61, further comprising one or more $G_A$ or $G_C$ moieties attached to each $G_B$ moiety, said compound having a formula:

$$G_A\text{-}(G_B\text{-}(P)_d)_m$$

wherein each P is independently $G_C$ or $G_A$, d is an integer from 1 to about 100, and m is an integer from 1 to about 20.

63. A compound according to claim 61, further comprising at least one $G_B$-$G_A$ moiety attached to one or more of said $G_C$ moiety, and having a formula:

$$G_A\text{-}(G_B\text{-}G_C\text{-}(G_B\text{-}G_A)_m)_p$$

wherein m is an integer from 1 to about 1,000 and p is an integer from 1 to about 1,000.

64. A compound according to claim 61, further comprising at least one $G_B$-$G_A$ moiety attached to one or more of said $G_C$ moiety, and having a formula:

$$(G_B\text{-}G_C)_e\text{-}(G_B\text{-}G_A)_n)_p$$

wherein n is an integer from 1 to about 1,000, p is an integer from 1 to about 100 and e is an integer from 1 to about 1,000.

65. A compound according to claim 61, further comprising at least one $G_B$-$G_C$ moiety attached to one or more $G_C$ moiety.

66. A compound according to claim 62, further comprising at least one $G_B$-$G_C$ moiety attached to one or more $G_C$ moiety.

67. A compound according to claim 63, further comprising at least one $G_B$-$G_C$ moiety attached to one or more $G_C$ moiety.

68. A compound according to claim 64, further comprising at least one $G_B$-$G_C$ moiety attached to one or more $G_C$ moiety.

69. A compound according to claim 65, wherein at least one $G_B$-$G_A$ moiety is attached to one or more $G_C$ moiety.

70. A compound according to claim 61, further comprising at least one $G_B$-$G_C$ moiety attached to one or more $G_A$ moiety.

71. A compound according to claim 62, further comprising at least one $G_B$-$G_C$ moiety attached to one or more $G_A$ moiety.

72. A compound according to claim 63, further comprising at least one $G_B$-$G_C$ moiety attached to one or more $G_A$ moiety.

73. A compound according to claim 64, further comprising at least one $G_B$-$G_C$ moiety attached to one or more $G_A$ moiety.

74. A compound according to claim 1, wherein $G_B$ is a multi-arm linking moiety linking at least one $G_A$ moiety and at least one $G_C$ moiety.

75. A compound according to claim 74, wherein $G_B$ is a pentaerythritol based multi-arm linking moiety linking from 1 to 4 $G_A$ and $G_C$ moieties.

76. A compound according to claim 74, wherein $G_B$ is a sorbitol-based multi-arm linking moiety linking from 1 to 6 $G_A$ and $G_C$ moieties.

77. A compound comprising $G_A$ linked to $G_B$ wherein $G_A$ is as defined in claim 1 and $G_B$ is selected from the group consisting of:

—O—CO—NH—, —NH—,

—O—CO—CH₂—CH₂—CO—NH—,

—O—CH₂—CO—NH—NH—CO—,

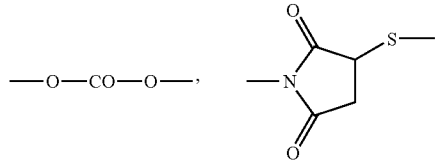,

—S—S—, —S—,

—S—CH₂—CH₂—NH—CO—O—,

—S—CH₂—CH₂—,

—O—CO—NH—CH₂—CH₂S—,

—S—CH₂—CH₂—NH—CO—CH₂—CH₂—,

—S—CH₂—CH₂—NH—CH₂—CH₂—CH₂—CH₂—,

—CO—NH—, 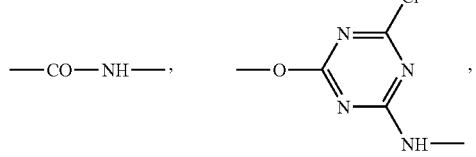,

—O—,

—O—CO—CH₂—CH₂—CH₂—CO—NH—,

—O—CH₂—CH(OH)—CH₂—O—,

—NH—CO—O—, —SO₂—CH₂—CH₂—S—,

—NH—CO—CH₂—S—, —CH₂—CH₂—S—,

—CO—NH—CH₂—CH₂—S—,

—S—CH₂—CH₂NH—CO—,

—S—CH₂—CH₂NH—CO—NH—CH₂—CH₂—,

—S—CH₂—CH₂—NH—CO—CH₂—CH₂—CH₂—O—, and

—S—CH₂—CH₂—NH—CO.

78. A mixture comprising:

$G_A$, $G_B$, and Gc, wherein $G_A$ has a structure according to formula I as defined in claim 1;

$G_B$ is a bond or a linking moiety as defined in claim 1;

$G_C$ is a moiety as defined in claim 1; and $G_A$ is a reaction product of an addition reaction, elimination reaction, replacement reaction, or any combination thereof of at least one atom of a pentaaza macrocycle selected from the group consisting of:

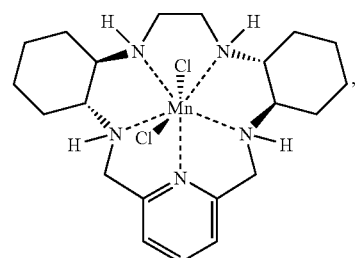,

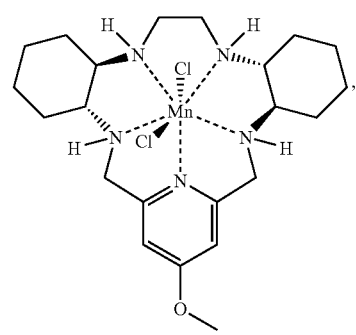,

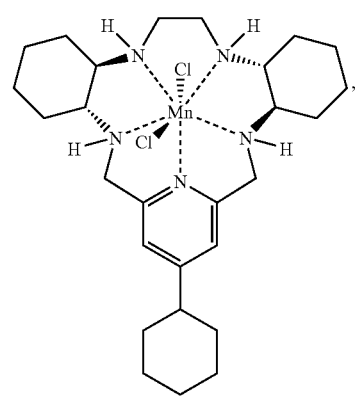,

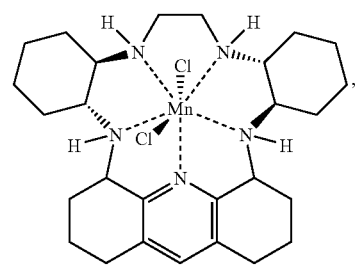

135
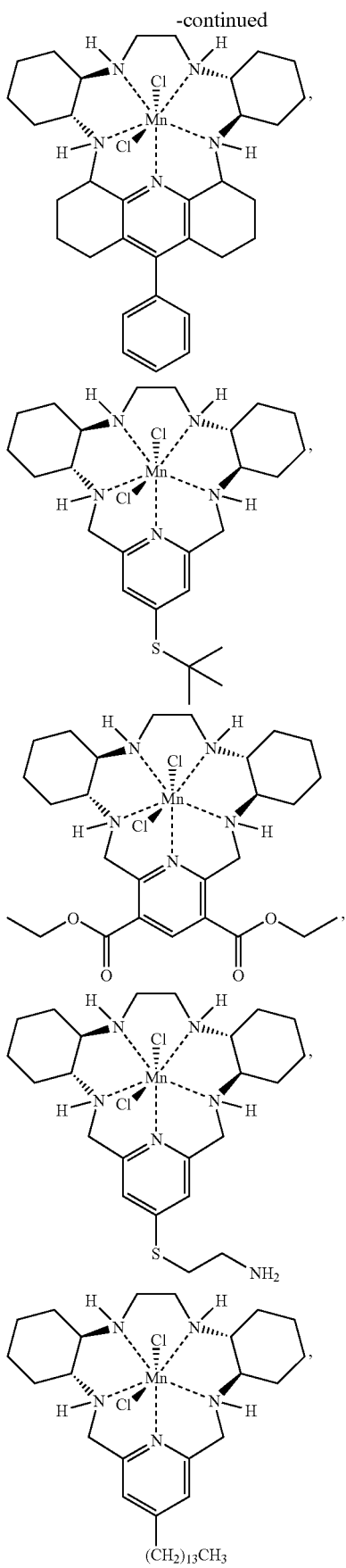
136
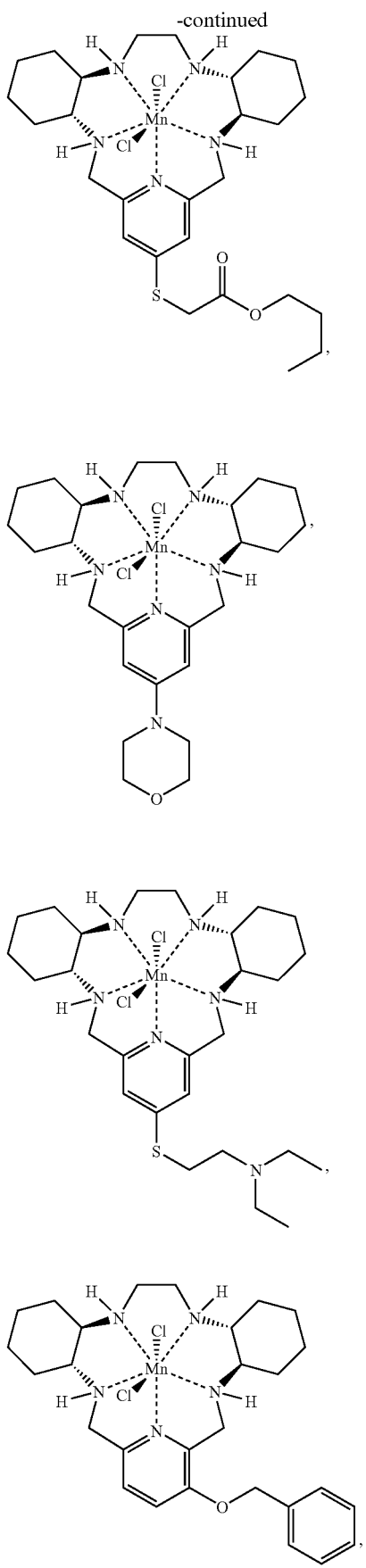

137
-continued
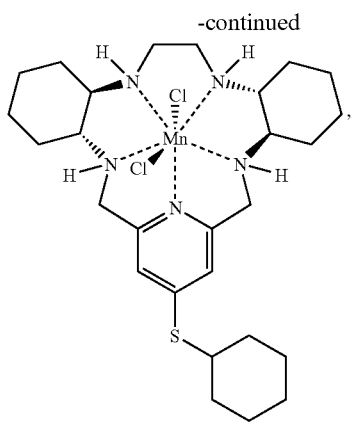
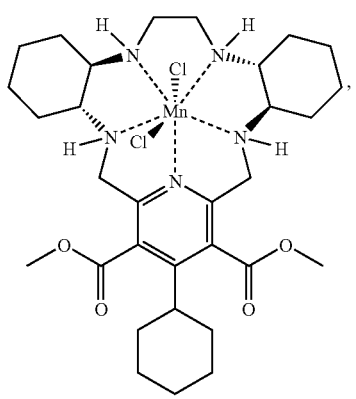
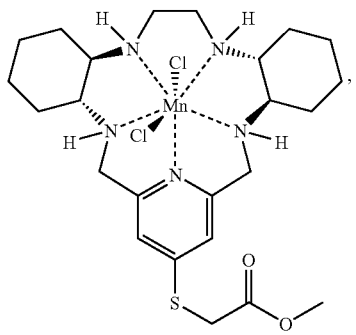
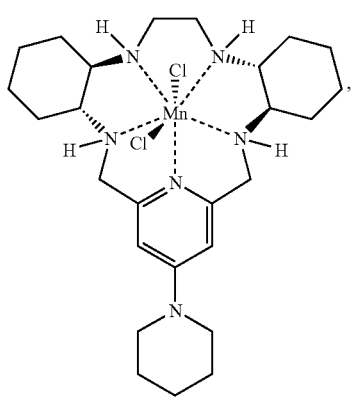
138
-continued
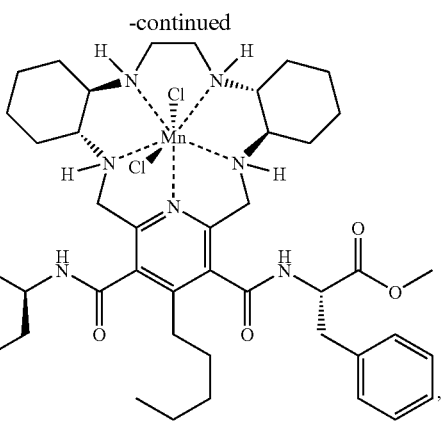
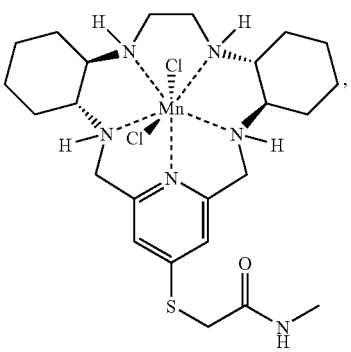
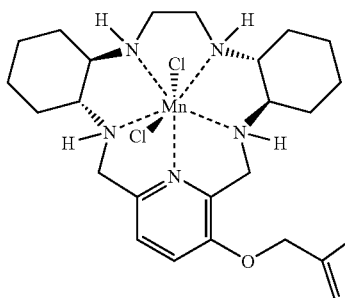
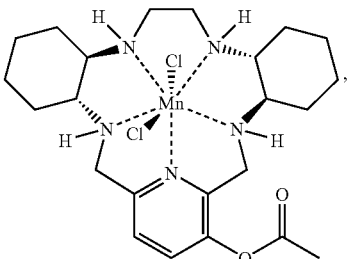
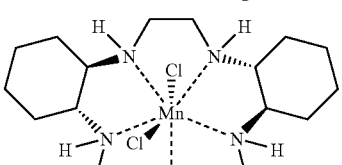
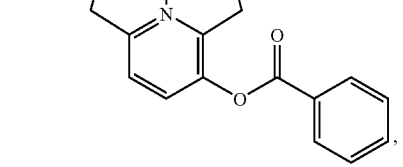

139
-continued
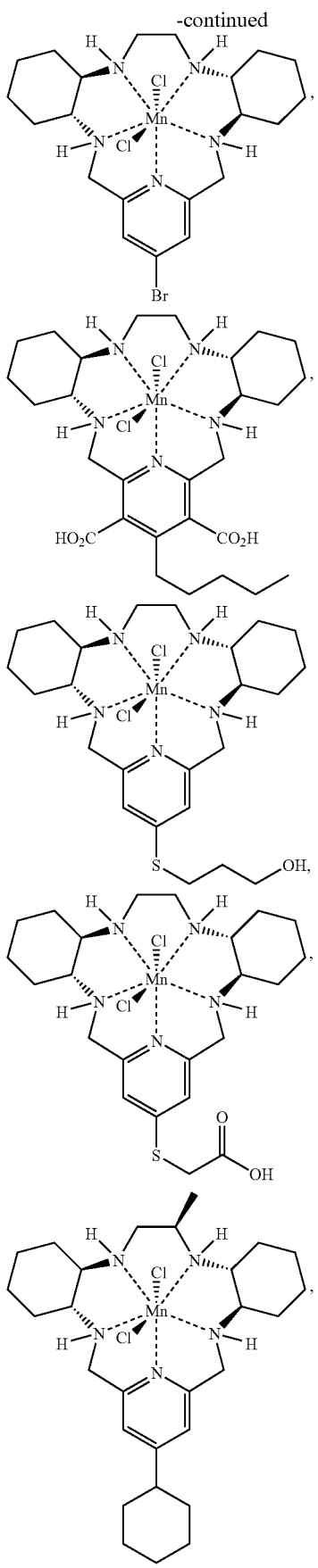
140
-continued
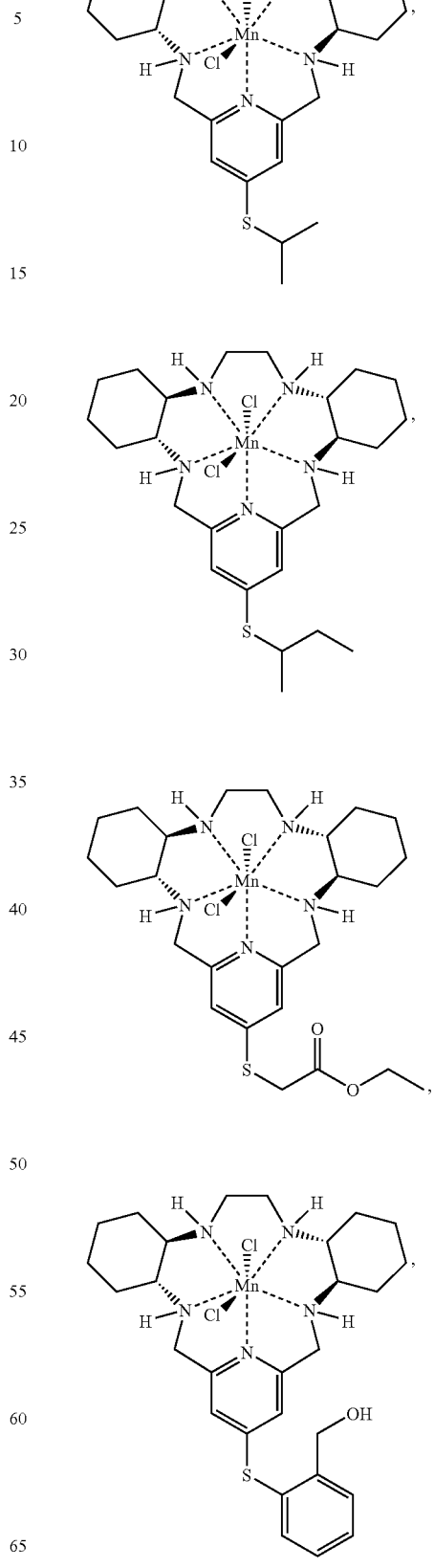

141
-continued
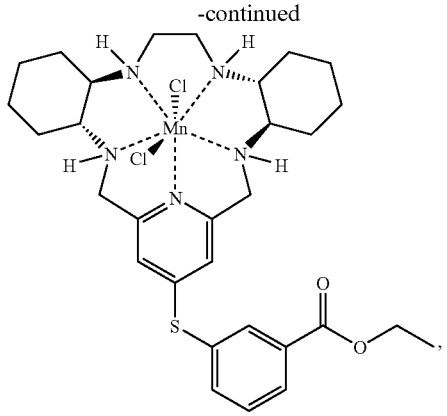
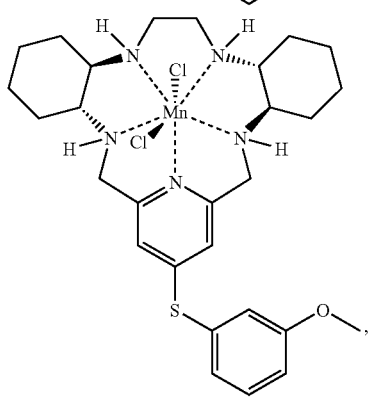
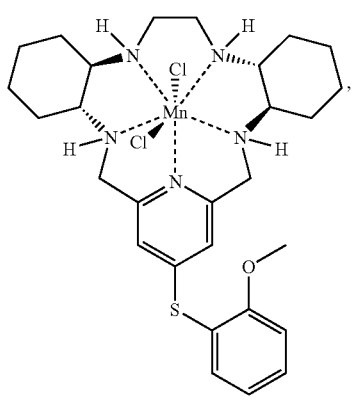
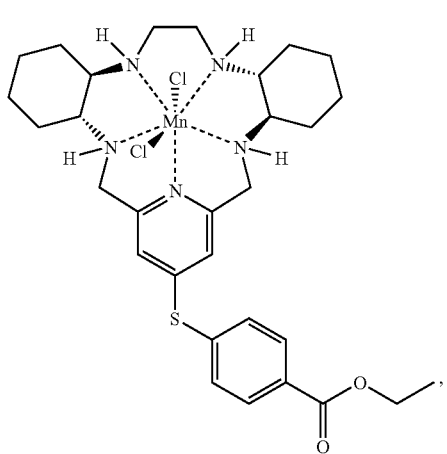
142
-continued
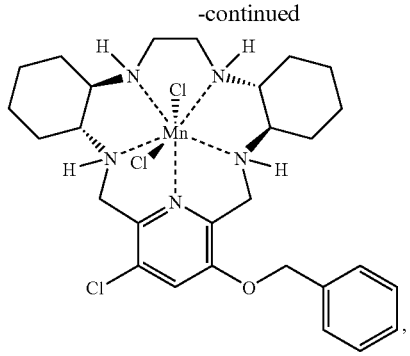
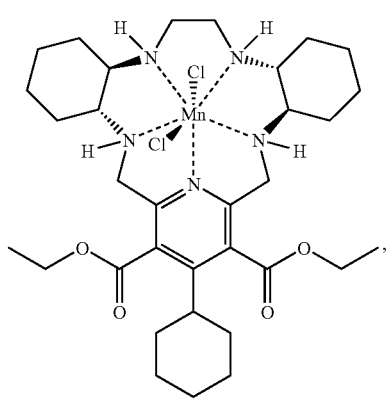
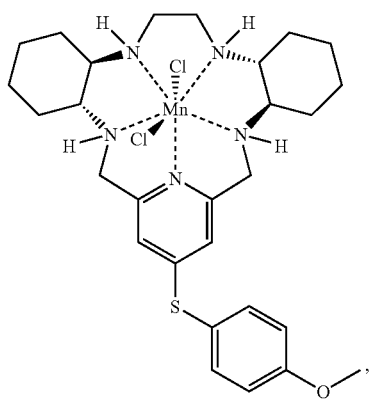
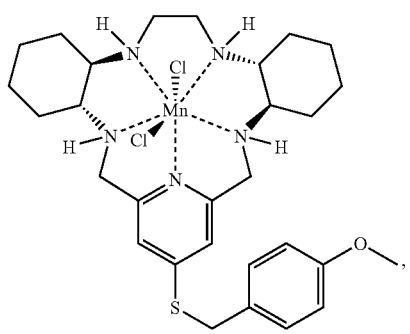

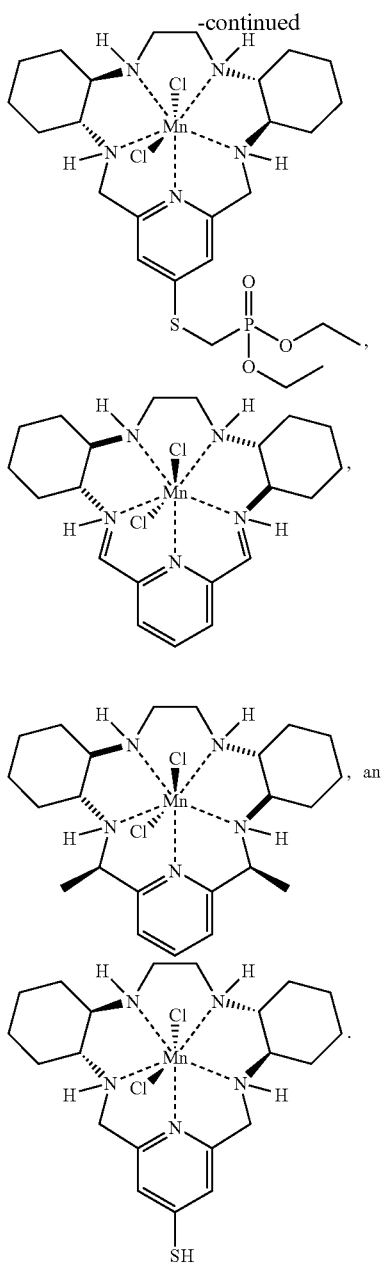

79. A mixture comprising:

$G_A$, $G_B$, and Gc, wherein $G_A$ has a structure according to formula I as defined in claim 1;

$G_B$ is a bond or a linking moiety as defined in claim 1;

$G_C$ is a moiety as defined in claim 1; and $G_A$ is a reaction product of an addition reaction, elimination reaction, replacement reaction, or any combination thereof, of at least one atom of a pentaaza macrocycle comprising a halogen.

80. A mixture according to claim 79, wherein $G_A$ is a reaction product of an addition, elimination, or replacement reaction or any combination thereof, of at least one atom of a pentaaza macrocycle selected from the group consisting of:

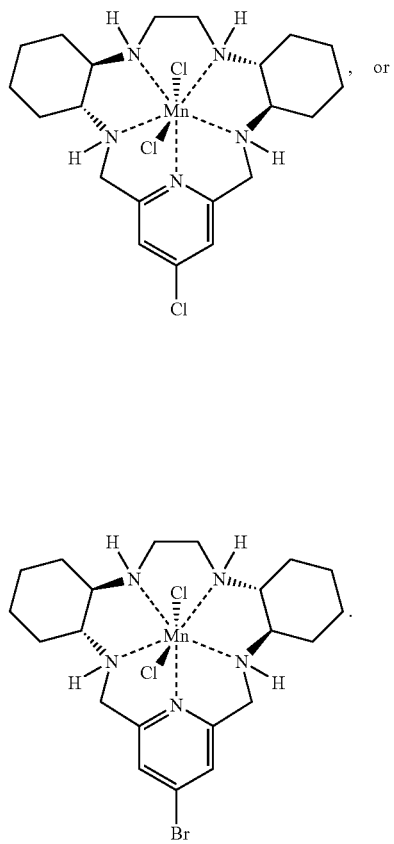

81. A mixture comprising:

$G_A$, $G_B$, and Gc, wherein $G_A$ has a structure according to formula I as defined in claim 1;

$G_B$ is a bond or a linking moiety as defined in claim 1;

$G_C$ is a moiety as defined in claim 1; and $G_A$ is a reaction product of an addition reaction, elimination reaction, replacement reaction, or any combination thereof, of at least one atom of a pentaaza macrocycle comprising a carbonyl.

82. A mixture of claim 81, wherein the pentaaza macrocycle is of the formula:

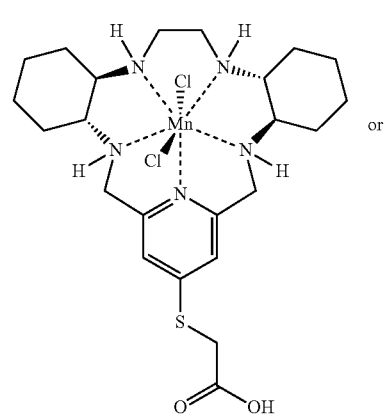

-continued

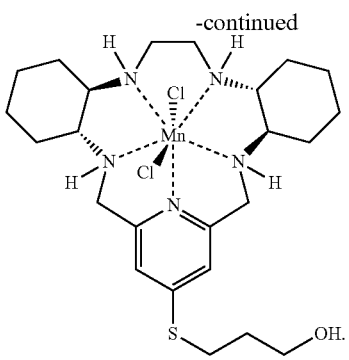

83. A method for preparing a compound of claim 1, the method comprising reacting a compound comprising a polyethylene glycol with a compound comprising a superoxide dismutase mimetic.

84. A method according to claim 83, wherein the polyethylene glycol is selected from the group consisting of
  (a) a monomethoxy polyethylene glycol succinimidyl propionic acid (mPEG-SPA),
  (b) a monomethoxy polyethylene glycol isocyanate (mPEG-isocyanate),
  (c) a monomethoxy polyethylene glycol benzotriazole carbonate (mPEG-BTC),
  (d) a bifunctional polyethylene glycol benzotriazole carbonate (BTC-POLYETHYLENE GLYCOL-BTC),
  (e) a monomethoxy polyethylene glycol N,N'-carbonyldiimidazole (mPEG-CDI)
  (f) a monomethoxy polyethylene glycol N-hydroxysuccinimidyl ester (mPEG-NHS),
  (g) monomethoxy polyethylene glycol thiol (m-PEG-SH), and
  (h) monomethoxy polyethylene glycol butyraldehyde (mPEG-butyrALD).

85. A method according to claim 83, further comprising reacting the polyethylene glycol with the superoxide dismutase mimetic in an organic solvent.

86. A method according to claim 85, wherein the organic solvent is $CH_2Cl_2$ or a dipolar aprotic solvent.

87. A method according to claim 86, wherein the dipolar aprotic solvent is selected from the group consisting of DMF or DMSO.

88. A method according to claim 83, wherein said reaction comprises an hydroxyl PEGylation reaction selected from the group consisting of:

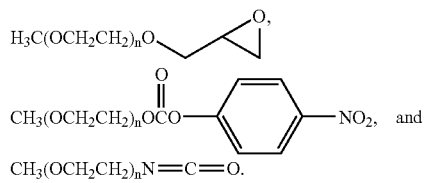

89. A method according to claim 88, wherein the superoxide dismutase mimetic is of the following formula:

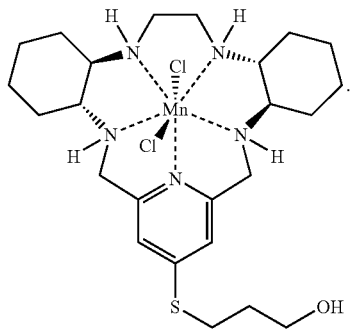

90. A method according to claim 83, wherein said reaction comprises a thiol PEGylation reaction wherein the polyethylene glycol is selected from the group consisting of:

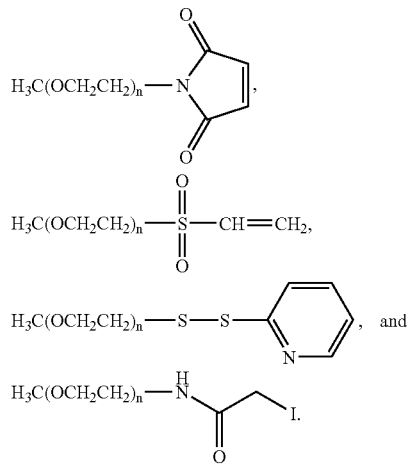

91. A method according to claim 90, wherein the superoxide dismutase mimetic is of the formula:

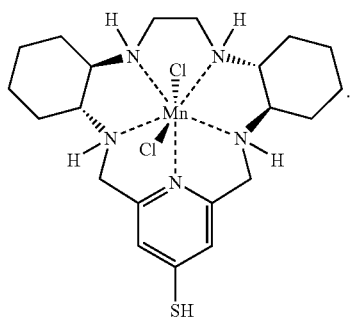

92. A method according to claim 83, wherein the polyethylene glycol is a monomethoxy polyethylene glycol.

* * * * *

UNITED STATES PATENT AND TRADEMARK OFFICE
CERTIFICATE OF CORRECTION

PATENT NO. : 8,217,166 B2  
APPLICATION NO. : 11/766221  
DATED : July 10, 2012  
INVENTOR(S) : Daniela Salvemini et al.

It is certified that error appears in the above-identified patent and that said Letters Patent is hereby corrected as shown below:

Title Page should read

(22) PCT Filed:      Dec. 21, 2005

(86) PCT No.:        PCT/US05/46825
    § 371(c)(1),
    (2), (4) Date:   Dec. 21, 2005

(87) PCT Pub. No.:   WO 2006/069362
    PCT Pub. Date:   Jun. 29, 2006

Related U.S. Application Data
(60) Provisional application No. 60/638,173, filed on Dec. 21, 2004 and Provisional application No. 60/677,999, filed on May 5, 2005.

Signed and Sealed this
Twenty-third Day of April, 2013

Teresa Stanek Rea
*Acting Director of the United States Patent and Trademark Office*